United States Patent
Connor et al.

(10) Patent No.: US 6,268,387 B1
(45) Date of Patent: Jul. 31, 2001

(54) THIOUREA AND BENZAMIDE COMPOUNDS, COMPOSITIONS AND METHODS OF TREATING OR PREVENTING INFLAMMATORY DISEASES AND ATHEROSCLEROSIS

(75) Inventors: David Thomas Connor; William Howard Roark; Karen Elaine Sexton; Roderick Joseph Sorenson, all of Ann Arbor, MI (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 09/529,135
(22) PCT Filed: Nov. 20, 1998
(86) PCT No.: PCT/US98/24688
§ 371 Date: Apr. 5, 2000
§ 102(e) Date: Apr. 5, 2000
(87) PCT Pub. No.: WO99/32433
PCT Pub. Date: Jul. 1, 1999

Related U.S. Application Data
(60) Provisional application No. 60/068,604, filed on Dec. 23, 1997.

(51) Int. Cl.[7] .......... A61K 31/44; A61K 31/17; C07D 335/00; C07D 24/72
(52) U.S. Cl. .......... 514/352; 514/586; 514/587; 546/309; 564/26; 564/27
(58) Field of Search .................. 514/352, 586, 514/587; 546/309; 564/26, 27

(56) References Cited

U.S. PATENT DOCUMENTS

| | | |
|---|---|---|
| 4,990,660 | 2/1991 | Neumann et al. . |
| 5,041,545 | 8/1991 | Myers . |
| 5,049,496 | 9/1991 | Mobley et al. . |
| 5,102,443 | 4/1992 | Kehne et al. . |
| 5,177,246 | 1/1993 | Pitteloud . |
| 5,457,122 | * 10/1995 | Konno . |
| 5,627,077 | 5/1997 | Dyllick-Brenzinger et al. . |

FOREIGN PATENT DOCUMENTS

| | | |
|---|---|---|
| 373028 | * 12/1963 | (CH) . |
| 0588060 | 3/1994 | (EP) . |
| 9209577 | 6/1992 | (WO) . |
| 9515690 | 6/1995 | (WO) . |

OTHER PUBLICATIONS

Ogata, J. Med. Chen, 29, pp417–423, 1986.*
Macrophage–medicated 15–Lipoxygenase Expression Protects against Atherosclerosis Development, Shen, Jianhe, et al., J. Clin. Invest., vol. 98, No.10, Nov. 1996, pp. 2201–2208.

* cited by examiner

Primary Examiner—D. Margaret Seaman
(74) Attorney, Agent, or Firm—Charles W. Ashbrook

(57) ABSTRACT

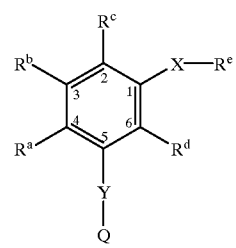

The present invention provides compounds of formula (I). The present invention also provides methods of treating or preventing inflammation or atherosclerosis, and a pharmaceutical composition that contains a compound of formula (I).

21 Claims, No Drawings

THIOUREA AND BENZAMIDE COMPOUNDS, COMPOSITIONS AND METHODS OF TREATING OR PREVENTING INFLAMMATORY DISEASES AND ATHEROSCLEROSIS

This application is a 371 of PCT/US98/246888 filed Nov. 20, 1998, which claims benefit to U.S. provisional application No. 60/068,604 filed Dec. 23, 1997.

FIELD OF THE INVENTION

The present invention relates to compounds that can be used to treat or prevent inflammatory diseases or atherosclerosis. The present invention also relates to pharmaceutical compositions that can be used to prevent or treat inflammatory diseases or atherosclerosis, and to methods of treating and preventing inflammatory diseases or atherosclerosis. In particular, the compounds of the present invention are inhibitors of the enzyme 15-lipoxygenase and are inhibitors of monocyte chemotaxis.

BACKGROUND OF THE INVENTION

Atherosclerosis is a multifactorial disease characterized by excessive intracellular lipid deposition in macrophages, leading to the formation of foam cells. The accumulation of lipid-loaded foam cells in the subendothelial space leads to formation of fatty streaks, which are the early atherosclerotic lesions. Oxidative modifications of lipids, specifically low-density lipoprotein, has been implicated as a major process in foam-cell formation.

Lipoxygenases are nonheme iron-containing enzymes that catalyze the oxygenation of certain polyunsaturated fatty acids such as lipoproteins. Several different lipoxygenase enzymes are known, each having a characteristic oxidation action. One specific lipoxygenase, namely 15-lipoxygenase (15-LO), has been detected in atherosclerotic lesions in mammals, specifically rabbit and man. The enzyme, in addition to its role in oxidative modification of lipoproteins, is important in the inflammatory reaction in the atherosclerotic lesion. Indeed, 15-LO has been shown to be induced in human monocytes by the cytokine IL-4, which is known to be implicated in the inflammatory process.

Inhibitors of 15-LO are especially useful to prevent and treat inflammatory diseases such as asthma, psoriasis, arthritis, and atherosclerosis. While there are several lipoxygenase enzymes, specific inhibition of 15-LO is important in the inflammatory and atherosclerosis process. A characteristic feature of atherosclerosis is the accumulation of cholesterol ester engorged foam cells. Foam cells are derived from circulating monocytes that invade artery walls in response to hypercholesterolemia, and mature into tissue macrophages. The enzyme 15-LO has been implicated in inflammatory disorders and in the origin and recruitment of foam cells (See Harats, et al., *Trends Cardiovasc. Med.,* 1995;5(1):29–36). This enzyme is capable of oxidizing esterified polyenoic fatty acids, such as those found in phospholipids. Treatment of experimental animals with antioxidants which reduced hydroperoxides produced by 15-LO has been shown to retard the progression of atherosclerotic lesions. For example, Sendobry, et al., *British Journal of Pharmacology,* 1997;120:1199–1206 show suppression of atherogenesis in rabbits fed a high-fat diet and treated with a 15-LO inhibitor.

SUMMARY OF THE INVENTION

The present invention provides compounds having the Formula I

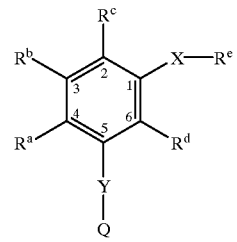

wherein X is

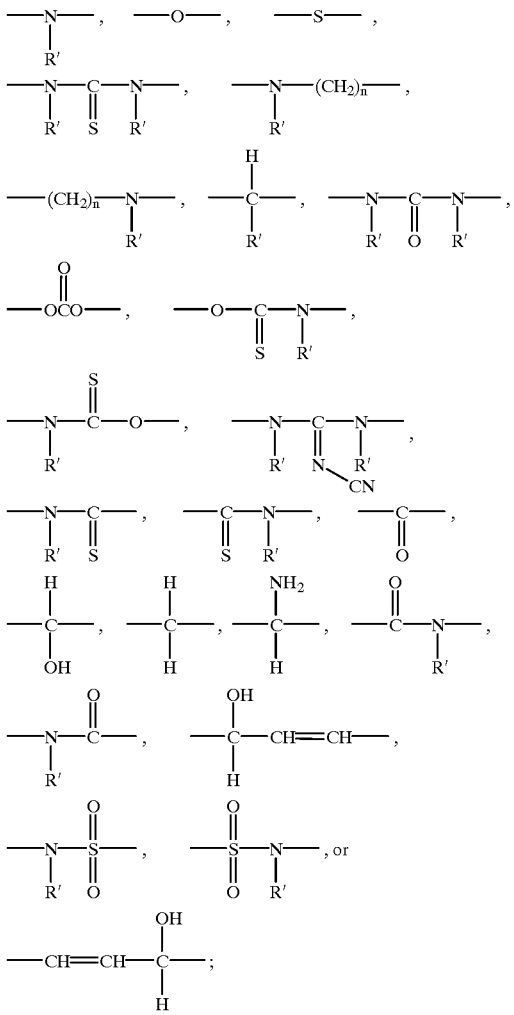

each n is independently 0 to 3;
Y is

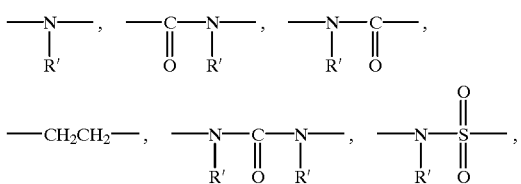

-continued $$-\overset{O}{\underset{O}{\overset{\|}{S}}}-\underset{R'}{N}-, \quad -\underset{R'}{N}-(CH_2)_{\overline{n}}-,$$

$$-\underset{R'}{N}-\overset{S}{\underset{\|}{C}}-\underset{R'}{N}-\overset{O}{\underset{\|}{C}}-, \quad -(CH_2)_{\overline{n}}-\underset{R'}{N}-,$$

$$-\overset{S}{\underset{\|}{C}}-\underset{R'}{N}-, \quad -\underset{R'}{N}-\overset{S}{\underset{\|}{C}}-,$$

$$-\overset{O}{\underset{\|}{C}}-\underset{R'}{N}-\overset{S}{\underset{\|}{C}}-\underset{R'}{N}-, \quad -\overset{O}{\underset{\|}{C}}-(CH_2)_{\overline{n}}-,$$

$$-(CH_2)_{\overline{n}}-\overset{OH}{\underset{O}{\overset{|}{C}}}-, \quad -\overset{OH}{\underset{H}{\overset{|}{C}}}-(CH_2)_n,$$

$$-(CH_2)_{\overline{n}}-\overset{OH}{\underset{H}{\overset{|}{C}}}-, \quad -\overset{OH}{\underset{H}{\overset{|}{C}}}-\overset{OH}{\underset{H}{\overset{|}{C}}}-, \quad -S-(CH_2)_n,$$

$$-(CH_2)_{\overline{n}}-S-, \quad -\overset{O}{\underset{\|}{C}}-O-, \quad -O-\overset{O}{\underset{\|}{C}}-,$$

$$-\overset{O}{\underset{\|}{C}}OCH_2-, \quad -CH_2O\overset{O}{\underset{\|}{C}}-, \quad -\overset{O}{\underset{\|}{S}}-(CH_2)_{\overline{n}}-,$$

$$(CH_2)_n-\overset{O\uparrow}{\underset{\|}{S}}-, \quad -SO_2-(CH_2)_{\overline{n}}-, \text{ or}$$

$$-(CH_2)_{\overline{n}}-SO_2-;$$

Q is $C_1$–$C_6$ alkyl,

[structure: phenyl ring with substituents $R^2$, $R^3$, $R^4$, $R^5$, $R^1$]

heteroaryl, substituted heteroaryl, —NR'R', or cycloalkyl; each R' is independently hydrogen or $C_1$–$C_6$ alkyl;

$R^e$ is

[structure: phenyl ring with substituents $R^9$, $R^8$, $R^7$]

$C_1$–$C_{18}$ alkyl, heteroaryl, substituted heteroaryl, naphthyl, benzyl, or dansyl;

each of $R^1, R^2, R^3, R^4, R^5, R^7, R^8, R^9, R^a, R^b, R^c,$ and $R^d$ are independently hydrogen, —$OC_1$–$C_6$ alkyl, —$SC_1$–$C_6$ alkyl, halogen, $C_1$–$C_6$ alkyl, —OH, —$CF_3$, —$NO_2$, —CN, —$CO_2$H, —$OCF_3$, —$CO_2C_1$–$C_6$ alkyl, —$SO_3$H, —$SO_3$-alkali metal —$NH_2$, —$NHC_1$–$C_6$ alkyl, $$-N(\overset{O}{\underset{\|}{C}}C_1\text{–}C_6\text{alkyl})_2, \quad -O\overset{O}{\underset{\|}{C}}C_1\text{–}C_6\text{alkyl},$$

—$CO_2C_1$–$C_6$ alkyl, —$SO_3$H, —$SO_3$ alkali metal, —CN, —$CH_2$-halogen,

[structures: $-CH_2-CH_2-$ with $-O-$ groups; oxazoline ring with $CH_3, CH_3$]

heteroaryl, substituted heteroaryl, aryl, substituted aryl, cycloalkyl, substituted cycloalkyl, heterocycloalkyl, substituted heterocycloalkyl, benzoyl, $$\overset{O}{\underset{\|}{C}}C_1\text{–}C_6\text{alkyl}, \quad -O\overset{O}{\underset{\|}{C}}H, \quad -O\overset{O}{\underset{\|}{C}}C_1\text{–}C_6\text{alkyl},$$

—$SO_3$H, —$SO_3$NR'R', —CHO, —$SO_2NH_2$, or —NR'R'; or the pharmaceutically acceptable salts thereof, provided that when Y is $$-\overset{O}{\underset{\|}{C}}O-,$$

Q is not $C_1$–$C_6$ alkyl; further provided that when X is $$-\overset{O}{\underset{\|}{C}}NH-$$

and

Y is —NH, $R^b$ is not —OH; further provided that when X and Y are $$-NH\overset{O}{\underset{\|}{C}}-,$$

$R^e$ and Q are not unsubstituted phenyl; further provided that when Y is $$-NH\overset{O}{\underset{\|}{C}}-,$$

and X is $$-NH\overset{O}{\underset{\|}{C}}O-,$$

$R^e$ and Q are not both aryl; further provided that when Y is —$SO_2NH$— or —$SO_2NC_1$–$C_6$ alkyl and X is

Q and R$^e$ are not both unsubstituted phenyl; further provided that when Y is

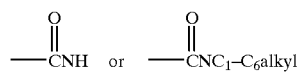

and X is

R$^e$ is unsubstituted phenyl di- or tri-substituted phenyl; further provided that when Y is

Q is not unsubstituted aryl.

In a preferred embodiment of the compounds of Formula I, X is

In another preferred embodiment of the compounds of Formula I, R' is hydrogen or methyl.

In another preferred embodiment of the compounds of Formula I, X is —O—.

In another preferred embodiment of the compounds of Formula I, X is $$-\underset{R'}{N}-\underset{S}{\overset{\|}{C}}-\underset{R'}{N}-.$$

In another preferred embodiment of the compounds of Formula I, R' is hydrogen.

In another preferred embodiment of the compounds of Formula I, R$^c$ is —OCH$_3$, hydrogen —OCH$_2$CH$_3$, halogen, —S-methyl, or —OCF$_3$.

In another preferred embodiment of the compounds of Formula I, Y is

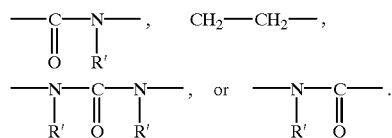

In another preferred embodiment of the compounds of Formula I, X is

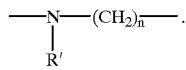

In another preferred embodiment of the compounds of Formula I, Y is

In another preferred embodiment of the compounds of Formula I, R$^c$ is hydrogen, hydroxy, —OC$_1$–C$_6$ alkyl, halogen, C$_1$–C$_6$ alkyl, —SC$_1$–C$_6$ alkyl, —CF$_3$, or —OCF$_3$.

Also provided is a method of treating or preventing atherosclerosis, the method comprising administering to a patient having atherosclerosis or at risk of having atherosclerosis a therapeutically effective amount of a compound of Formula I

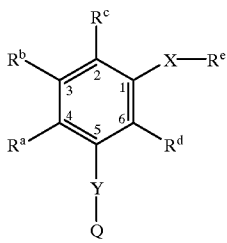

wherein X is

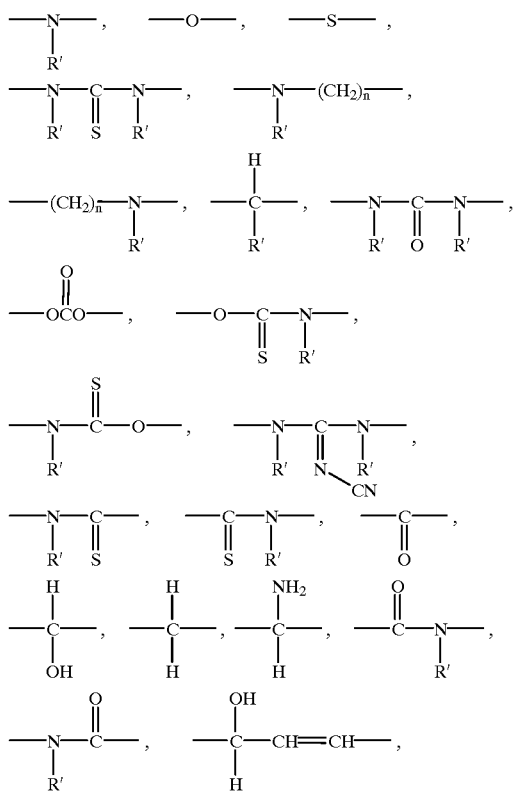

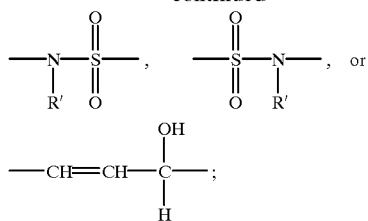

each n is independently 0 to 3;
Y is

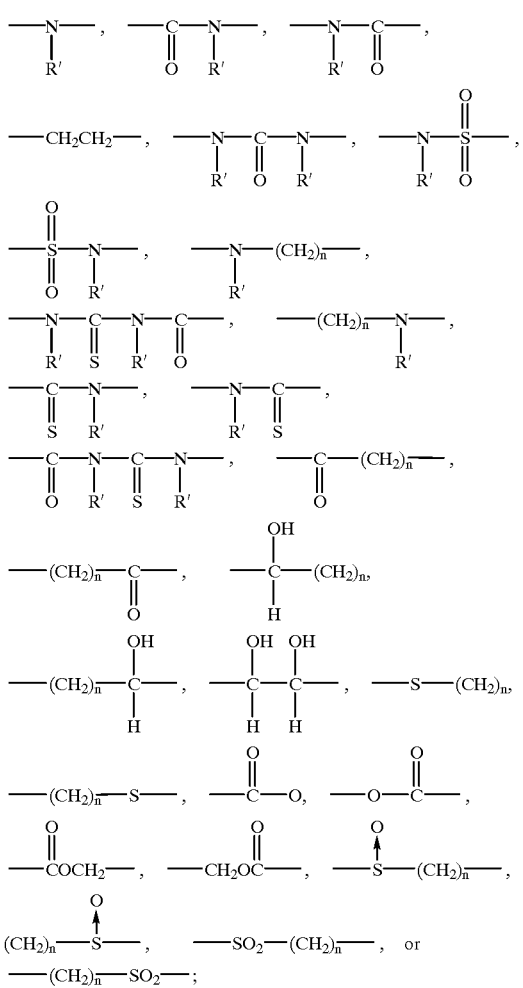

Q is $C_1$–$C_6$ alkyl,

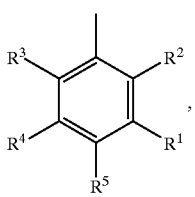

heteroaryl, substituted heteroaryl, —NR'R', or cycloalkyl;
each R' is independently hydrogen or $C_1$–$C_6$ alkyl;

$R^e$ is

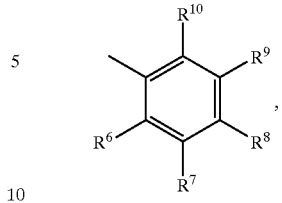

$C_1$–$C_{18}$ alkyl, heteroaryl, substituted heteroaryl, naphthyl, benzyl, or dansyl;

each of $R^1$, $R^2$, $R^3$, $R^4$, $R^5$, $R^7$, $R^8$, $R^9$, $R^{10}$, $R^a$, $R^b$, $R^c$, and $R^d$ are independently hydrogen —$OC_1$–$C_6$ alkyl, —$SC_1$–$C_6$ alkyl, halogen, $C_1$–$C_6$ alkyl, —OH, —$CF_3$, —$NO_2$, —CN, —$CO_2H$, —$OCF_3$, —$CO_2C_1$–$C_6$ alkyl, —$SO_3H$, —$SO_3$-alkali metal. —$NH_2$, —$NHC_1$–$C_6$ alkyl,

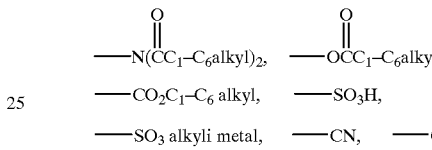

—$CO_2C_1$—$C_6$ alkyl, —$SO_3H$, —$SO_3$ alkali metal, —CN, —$CH_2$—halogen,

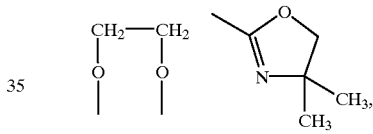

heteroaryl, substituted heteroaryl, aryl, substituted aryl, cycloalkyl, substituted cycloalkyl, heterocycloalkyl, substituted heterocycloalkyl, benzoyl,

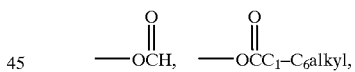

—$SO_3H$, —$SO_3NR'R'$, —CHO, —$SO_2NH_2$, or —NR'R', or the pharmaceutically acceptable salts thereof.

Also provided is a method of treating or preventing inflammation, the method comprising administering to a patient having inflammation or at risk of having inflammation a therapeutically effective amount of a compound of Formula I

I

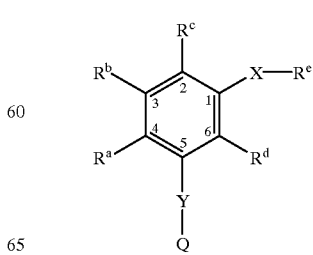

wherein X is

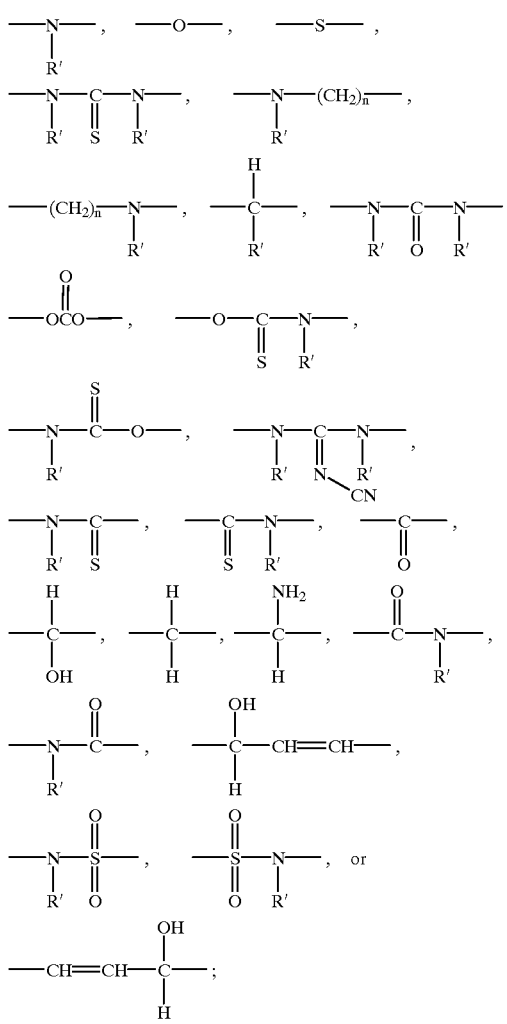

each n is independently 0 to 3;
Y is

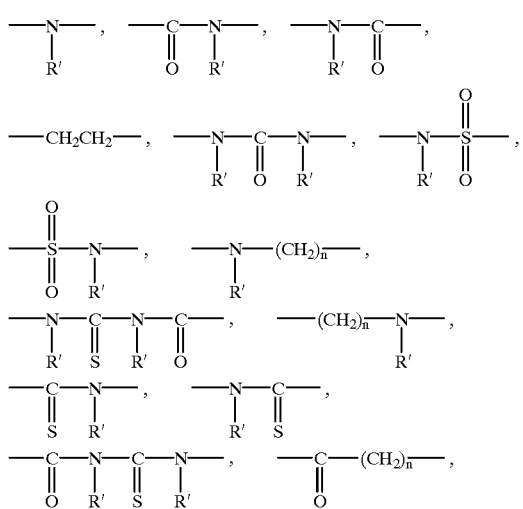

—SO$_2$—(CH$_2$)$_n$—, or —(CH$_2$)$_n$—SO$_2$—;

Q is C$_1$–C$_6$ alkyl,

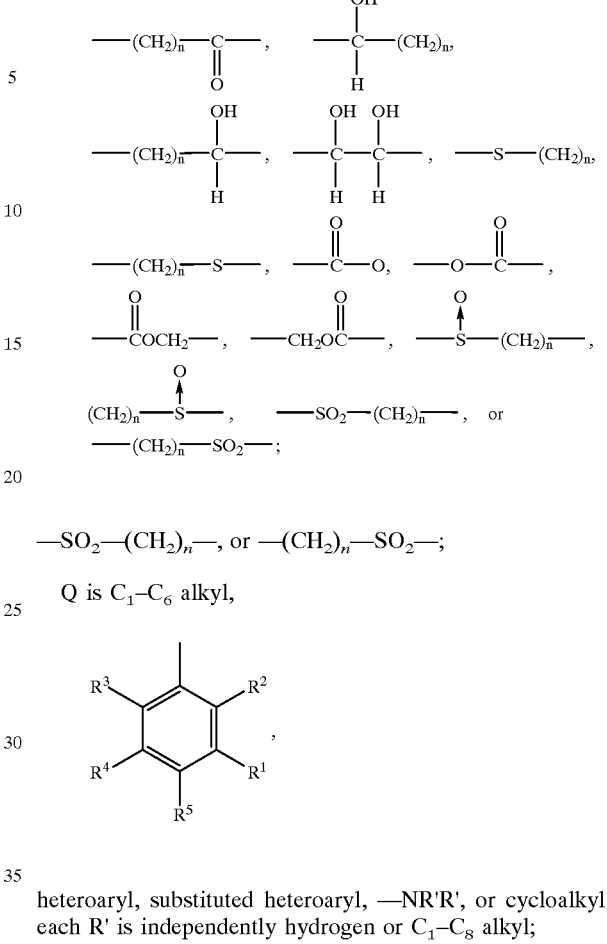

heteroaryl, substituted heteroaryl, —NR'R', or cycloalkyl;
each R' is independently hydrogen or C$_1$–C$_8$ alkyl;

R$^e$ is

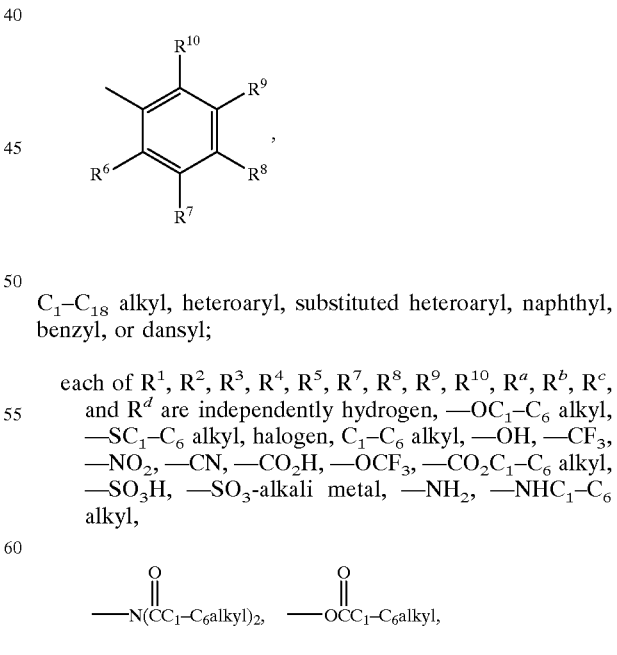

C$_1$–C$_{18}$ alkyl, heteroaryl, substituted heteroaryl, naphthyl, benzyl, or dansyl;

each of R$^1$, R$^2$, R$^3$, R$^4$, R$^5$, R$^7$, R$^8$, R$^9$, R$^{10}$, R$^a$, R$^b$, R$^c$, and R$^d$ are independently hydrogen, —OC$_1$–C$_6$ alkyl, —SC$_1$–C$_6$ alkyl, halogen, C$_1$–C$_6$ alkyl, —OH, —CF$_3$, —NO$_2$, —CN, —CO$_2$H, —OCF$_3$, —CO$_2$C$_1$–C$_6$ alkyl, —SO$_3$H, —SO$_3$-alkali metal, —NH$_2$, —NHC$_1$–C$_6$ alkyl, —N(CC$_1$–C$_6$alkyl)$_2$, —OCC$_1$–C$_6$alkyl, —CO$_2$C$_1$–C$_6$ alkyl, —SO$_3$H, —SO$_3$ alkali metal, —CN, —CH$_2$-halogen,

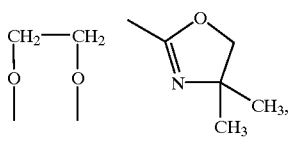

heteroaryl, substituted heteroaryl, aryl, substituted aryl, cycloalkyl, substituted cycloalkyl, heterocycloalkyl, substituted heterocycloalkyl, benzoyl,

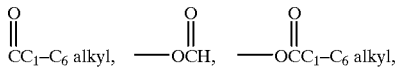

—SO$_3$H, —SO$_3$NR'R', —CHO, —SO$_2$NH$_2$, or —NR'R', or the pharmaceutically acceptable salts thereof.

The present invention provides a pharmaceutically acceptable composition comprising a compound of Formula I.

Also provided is a method of inhibiting 15-lipoxygenase, the method comprising administering to a patient in need of 15-lipoxygenase inhibition a 15-lipoxygenase inhibiting amount of a compound of Formula I

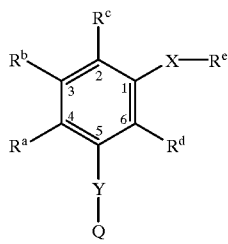

I wherein X is

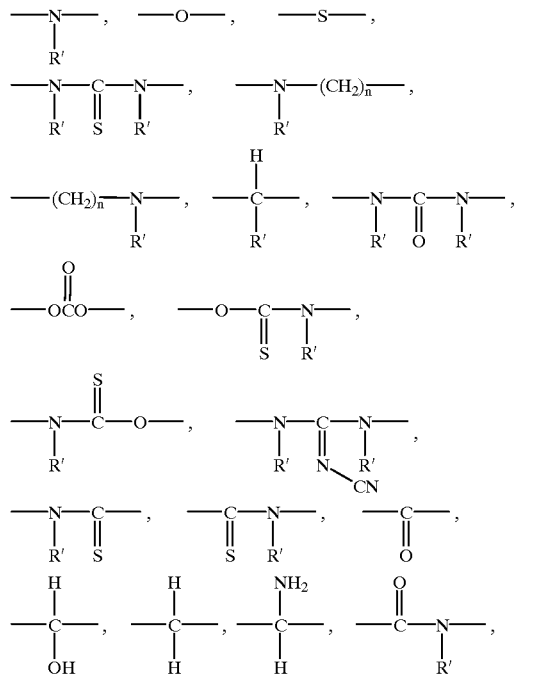

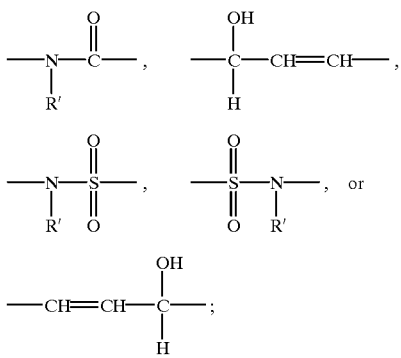

each n is independently 0 to 3;

Y is

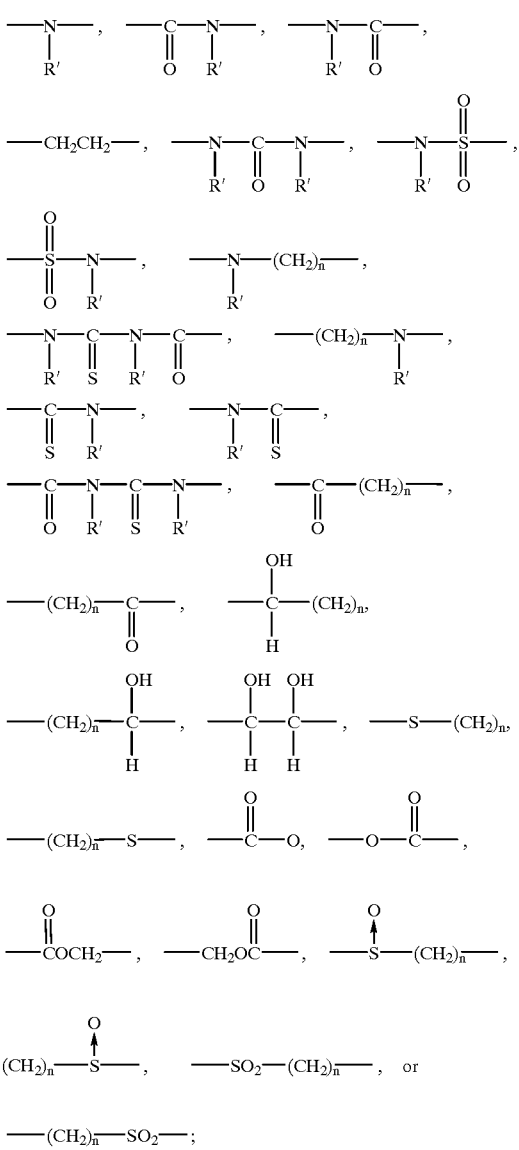

Q is $C_1$–$C_6$ alkyl,

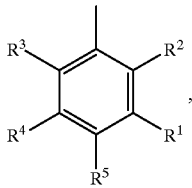

heteroaryl, substituted heteroaryl, —NR'R', or cycloalkyl;

each R' is independently hydrogen or $C_1$–$C_6$ alkyl;

$R^e$ is

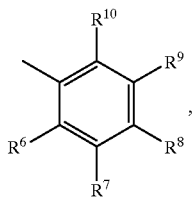

$C_1$–$C_{18}$ alkyl, heteroaryl, substituted heteroaryl, naphthyl, benzyl, or dansyl;

each of $R^1$, $R^2$, $R^3$, $R^4$, $R^5$, $R^6$, $R^7$, $R^8$, $R^9$, $R^{10}$, $R^a$, $R^b$, $R^c$, and $R^d$ are independently hydrogen, —O$C_1$–$C_6$ alkyl, —S$C_1$–$C_6$ alkyl, halogen, $C_1$–$C_6$ alkyl, —OH, —$CF_3$, —$NO_2$, —CN, —$CO_2$H, —$OCF_3$, —$CO_2C_1$–$C_6$ alkyl,

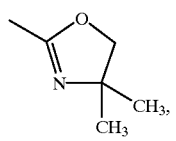

heteroaryl, substituted heteroaryl, aryl, substituted aryl, cycloalkyl, substituted cycloalkyl, heterocycloalkyl, substituted heterocycloalkyl, benzoyl,

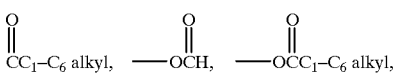

—$SO_3$H, —$SO_3$NR'R', —CHO, —$SO_2NH_2$, or —NR'R', or the pharmaceutically acceptable salts thereof.

Also provided is a method of inhibiting the chemotaxis of monocytes, the method comprising administering to a patient in need of inhibition of chemotaxis of monocytes, a monocyte chemotaxis inhibiting amount of a compound of Formula I

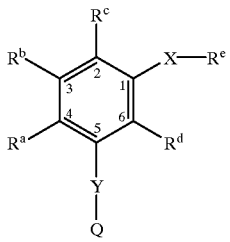

wherein X is

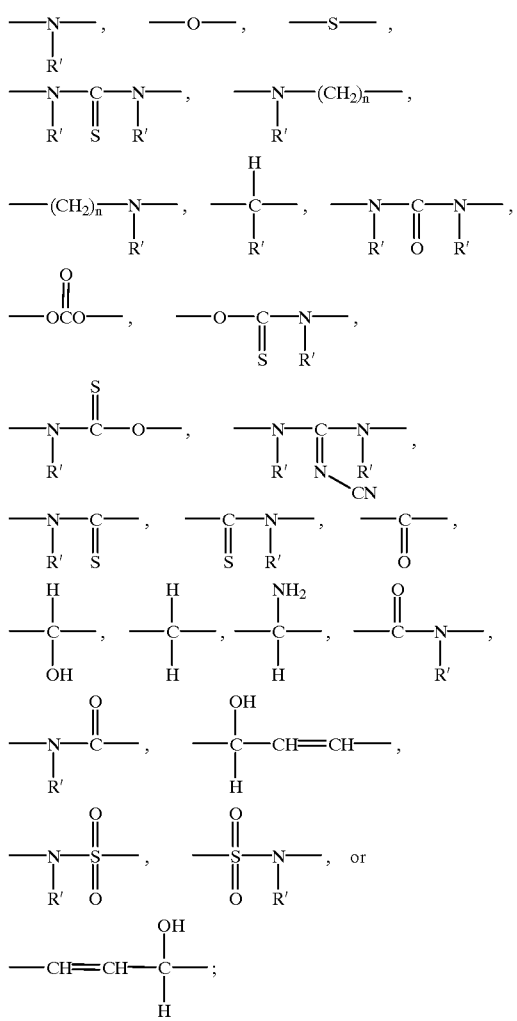

each n is independently 0 to 3;

Y is

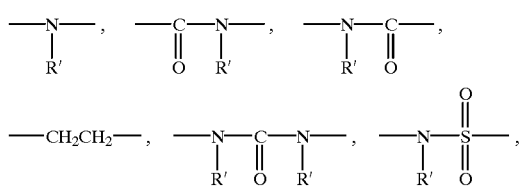

-continued

[chemical structures: various substituent groups including —S(O)₂—N(R')—, —N(R')—(CH₂)ₙ—, —N(R')—C(S)—N(R')—C(O)—, —(CH₂)ₙ—N(R')—, —C(S)—N(R')—, —N(R')—C(S)—, —C(O)—N(R')—C(S)—N(R')—, —C(O)—(CH₂)ₙ—, —(CH₂)ₙ—C(OH)—, —C(OH)(H)—(CH₂)ₙ—, —(CH₂)ₙ—C(OH)(H)—, —C(OH)(H)—C(OH)(H)—, —S—(CH₂)ₙ—, —(CH₂)ₙ—S—, —C(O)—O—, —O—C(O)—, —C(O)CH₂—, —CH₂OC(O)—, —S(O)—(CH₂)ₙ—, (CH₂)ₙ—S(O)—, —SO₂—(CH₂)ₙ—, or —(CH₂)ₙ—SO₂—;]

Q is $C_1$–$C_6$ alkyl,

[phenyl ring with substituents $R^1$, $R^2$, $R^3$, $R^4$, $R^5$ and methyl], heteroaryl, substituted heteroaryl, —NR'R', or cycloalkyl;
each R' is independently hydrogen or $C_1$–$C_6$ alkyl;
$R^e$ is

[phenyl ring with substituents $R^6$, $R^7$, $R^8$, $R^9$, $R^{10}$ and methyl], $C_1$–$C_{18}$ alkyl, heteroaryl, substituted heteroaryl, naphthyl, benzyl, or dansyl;

each of $R^1$, $R^2$, $R^3$, $R^4$, $R^5$, $R^7$, $R^8$, $R^9$, $R^{10}$, $R^a$, $R^b$, $R^c$, and $R^d$ are independently hydrogen, —O$C_1$–$C_6$ alkyl, —S$C_1$–$C_6$ alkyl, halogen, $C_1$–$C_6$ alkyl, —OH, —CF₃, —NO₂, —CN, —CO₂H, —OCF₃, —CO₂$C_1$–$C_6$ alkyl, —SO₃H, —SO₃-alkali metal, —NH₂, —NH$C_1$–$C_6$ alkyl, —N(C(O)$C_1$–$C_6$alkyl)₂, —OC(O)$C_1$–$C_6$alkyl,
—CO₂$C_1$–$C_6$ alkyl, —SO₃H, —SO₃ alkali metal, —CN, —CH₂-halogen,

[structures: —CH₂—O—CH₂—O— (dioxolane), and 2-substituted 4,4-dimethyl-oxazoline], heteroaryl, substituted heteroaryl, aryl, substituted aryl, cycloalkyl, substituted cycloalkyl, heterocycloalkyl, substituted heterocycloalkyl, benzoyl, —C(O)$C_1$–$C_6$alkyl, —OC(O)H, —OC(O)$C_1$–$C_6$alkyl, —SO₃H, —SO₃NR'R', —CHO, —SO₂NH₂, or —NR'R', and the pharmaceutically acceptable salts thereof.

Also provided by the present invention are compounds having the Formula II

II

[structure: benzene ring with B substituent, NH–$R^e$ group, and Y–Q group]

wherein
$R^e$ is phenyl, pyridyl, or substituted phenyl having 1 to 5 substituents selected from halogen, $C_1$–$C_6$ alkyl, O$C_1$–$C_6$ alkyl, —CF₃, or —OH;
B is hydrogen, O$C_1$–$C_6$ alkyl, halogen, $C_1$–$C_6$ alkyl, —S$C_1$–$C_6$ alkyl, —OCF₃, or —OH;

Y is —C(O)NH— or —NHC(O)—;

Q is phenyl, pyridyl, or substituted phenyl having from 1 to 5 substituents selected from halogen, —O$C_1$–$C_6$ alkyl, oxazolinyl, —CF₃, NO₂, —C(O)O$C_1$–$C_6$alkyl, or —$C_1$–$C_6$ alkyl, or the pharmaceutically acceptable salts thereof.

In a preferred embodiment of the compounds of Formula II, B is —OCH₃ or —OCF₃.

In a preferred embodiment of the compounds of Formula II, $R^e$ is substituted phenyl.

In a preferred embodiment of the compounds of Formula II,

Y is .

In a preferred embodiment of the compounds of Formula II, B is —OCH$_3$, or —OCF$_3$; R$^e$ is substituted phenyl and Y is

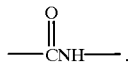.

Also provided are compounds having the Formula III

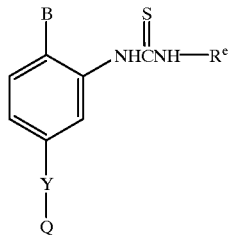

III wherein

R$^e$ is pyridyl, or phenyl that is substituted with from 1 to 5 substituents selected from halogen, —CF$_3$, —NO$_2$, benzoyl, —SO$_3$ alkali metal, C$_1$-C$_6$ alkyl, —OC$_1$-C$_6$ alkyl, —CN, —COOH,

—SO$_3$H, —OCF$_3$,

—SO$_2$NH$_2$, N(C$_1$-C$_6$ alkyl)$_2$, or —SONH$_2$;

B is OC$_1$-C$_6$ allyl, hydrogen, halogen, or C$_1$-C$_6$ alkyl;

Y is 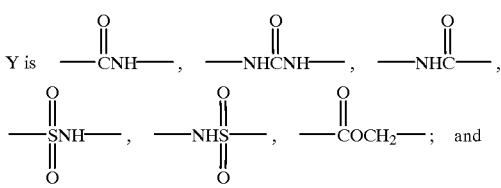; and

Q is phenyl, pyridyl, or phenyl substituted with 1 to 5 substituents selected from halogen, —OC$_1$-C$_6$ alkyl, halogen, or C$_1$-C$_6$ alkyl, or the pharmaceutically acceptable salts thereof.

In a preferred embodiment of the compounds of Formula III, R$^e$ is substituted phenyl.

In a preferred embodiment of the compounds of Formula III, B is —OCH$_3$ or —OCF$_3$, or fluorine.

In a preferred embodiment of the compounds of Formula III,

Y is 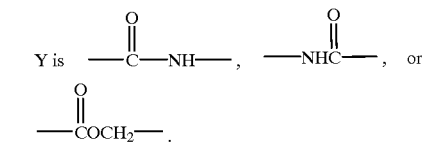

In a preferred embodiment of the compounds of Formula III, R$^e$ is substituted phenyl, B is —OCH$_3$, —OCF$_3$, and Y is

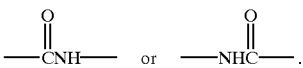.

Also provided are compounds having the Formula IV

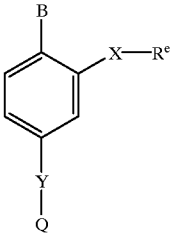

IV wherein

X is —NHCH$_2$—, —O—,

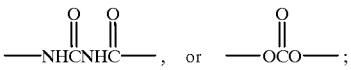;

B is —OC$_1$-C$_6$ alkyl, hydrogen, or —OH;

R$^e$ is phenyl, pyridyl, or phenyl substituted with 1 to 5 substituents selected from halogen, —OC$_1$-C$_6$ alkyl, —OH, —NH$_2$, —NHC$_1$-C$_6$ alkyl,

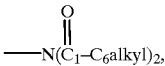

—NO$_2$, —C$_1$-C$_6$ alkyl, naphthyl, —CF$_3$, —OCF$_3$,

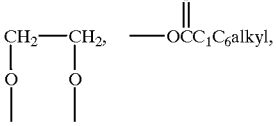

—CO$_2$C$_1$-C$_6$ alkyl, furyl, CN, —CO$_2$H, or phenyl;

Y is 

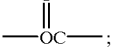;

and Q is phenyl, pyridyl, or substituted phenyl, wherein the substituted phenyl may contain 1 to 5 substituents selected from those listed for $R^e$, or the pharmaceutically acceptable salts thereof.

In a preferred embodiment of the compounds of Formula IV, $R^e$ is substituted phenyl.

In a preferred embodiment of the compounds of Formula IV, B is —OCH$_3$.

In a preferred embodiment of the compounds of Formula IV, X is —NHCH$_2$—.

In a preferred embodiment of the compounds of Formula IV,

Y is 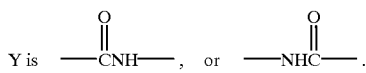.

In a preferred embodiment of the compounds of Formula IV, $R^e$ is substituted phenyl; B is —OCH$_3$; X is —NHCH$_2$—; and Y is

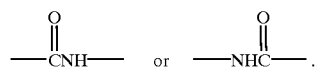.

Also provided are compounds having the Formula V

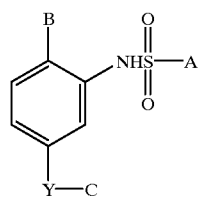

B is —OC$_1$–C$_6$ alkyl or halogen;

A is phenyl, C$_1$–C$_{18}$ alkyl, pyridyl, quinolinyl substituted phenyl, thiazolyl, substituted thiazolyl, substituted pyridyl, substituted quinolinyl, imidazolyl, substituted imidazolyl, naphthyl, substituted naphthyl, benzyl, thienyl, substituted thienyl, isoxazolyl, or substituted isoxazolyl, wherein the substituents are selected from halogen, —OC$_1$–C$_6$ alkyl, —NO$_2$, C$_1$–C$_6$ alkyl, —CF$_3$,

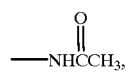,

—CO$_2$H, —NH$_2$, —NHC$_1$–C$_6$ alkyl,

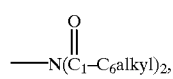

—CN, or —CH$_2$-halogen;

Y is

,

,

—CH$_2$NH—, or —NH$_2$CH—; and

C is phenyl or substituted phenyl, pyridyl or substituted pyridyl, wherein the substituents are as described for A, or the pharmaceutically acceptable salts thereof.

In a preferred embodiment of the compounds of Formula V, A is C$_1$–C$_{18}$ alkyl, substituted phenyl, or thienyl.

In a preferred embodiment of the compounds of Formula V, B is —OCH$_3$ or halogen.

In a preferred embodiment of the compounds of Formula V,

Y is

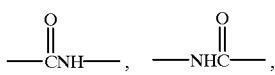, or —CH$_2$NH—.

In a preferred embodiment of the compounds of Formula V, A is C$_1$–C$_{18}$ alkyl, substituted phenyl or thienyl; B is —OCF$_3$ or halogen; and Y is .

Also provided is a method of treating or preventing atherosclerosis, the method comprising administering to a patient having atherosclerosis or at risk of having atherosclerosis a therapeutically effective amount of a compound of Formula VI

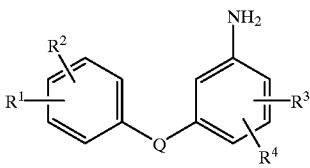

wherein Q is

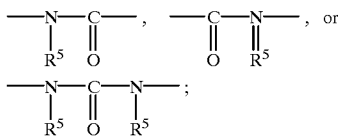;

each $R^5$ is independently hydrogen or C$_1$–C$_6$ alkyl;

$R^1$, $R^2$, $R^3$, and $R^4$ are independently hydrogen, —SC$_1$–C$_6$ alkyl, —OCF$_3$, —OH, halogen, —CF$_3$, —NO$_2$, —COOR$^5$, —SO$_3$NR$^5$R$^5$, —CHO, —OC$_1$–C$_6$ alkyl, —NR$^5$R$^5$, C$_1$–C$_6$ alkyl, heteroaryl, substituted heteroaryl, aryl, substituted aryl, cycloalkyl, substituted cycloalkyl, heterocycloalkyl, substituted heterocycloalkyl, or the pharmaceutically acceptable salts thereof.

Also provided is a method of treating or preventing inflammation, the method comprising administering to a patient having inflammation or at risk of having inflammation a therapeutically effective amount of a compound of Formula VI

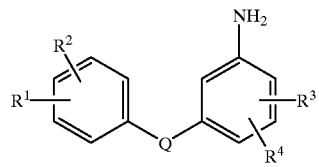

VI wherein Q is

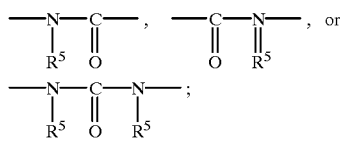

each $R^5$ is independently hydrogen or $C_1$–$C_6$ alkyl;
$R^1$, $R^2$, $R^3$, and $R^4$ are independently hydrogen, —$SC_1$–$C_6$ alkyl, —OH, halogen, —$CF_3$, —$NO_2$, —$COOR^5$, —$SO_3NR^5R^5$, —CHO, —$OCF_3$, —$OC_1$–$C_6$ alkyl, —$NR^5R^5$, $C_1$–$C_6$ alkyl, heteroaryl, substituted heteroaryl, aryl, substituted aryl, cycloalkyl, substituted cycloalkyl, heterocycloalkyl, substituted heterocycloalkyl, or the pharmaceutically acceptable salts thereof.

Also provided is a method of inhibiting 15-lipoxygenase, the method comprising administering to a patient in need of 15-lipoxygenase inhibition a 15-lipoxygenase inhibiting amount of a compound of Formula VI

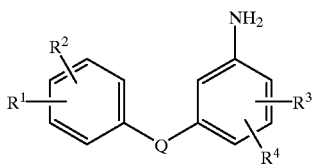

VI wherein Q is

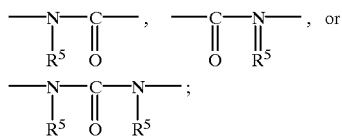

each $R^5$ is independently hydrogen or $C_1$–$C_6$ alkyl;
$R^1$, $R^2$, $R^3$, and $R^4$ are independently hydrogen, —$SC_1$–$C_6$ alkyl, —OH, halogen, —$CF_3$, —$NO_2$, —$COOR^5$, —$SO_3NR^5R^5$, —CHO, —$OCF_3$, —$OC_1$–$C_6$ alkyl, —$NR^5R^5$, $C_1$–$C_6$ alkyl, heteroaryl, substituted heteroaryl, aryl, substituted aryl, cycloalkyl, substituted cycloalkyl, heterocycloalkyl, substituted heterocycloalkyl, or the pharmaceutically acceptable salts thereof.

Also provided is a method of inhibiting the chemotaxis of monocytes, the method comprising administering to a patient in need of inhibition of chemotaxis of monocytes a chemotaxis inhibiting amount of a compound of Formula VI

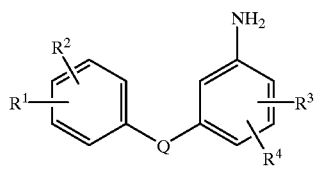

VI wherein Q is

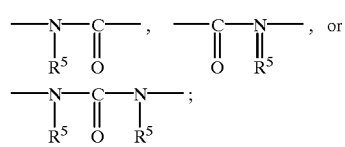

each $R^5$ is independently hydrogen or $C_1$–$C_6$ allyl;
$R^1$, $R^2$, $R^3$, and $R^4$ are independently hydrogen, —$SC_1$–$C_6$ alkyl, —OH, halogen, —$CF_3$, —$NO_2$, —$COOR^5$, —$SO_3NR^5R^5$, —CHO, —$OCF_3$, —$OC_1$–$C_6$ alkyl, —$NR^5R^5$, $C_1$–$C_6$ alkyl, heteroaryl, substituted heteroaryl, aryl, substituted aryl, cycloalkyl, substituted cycloalkyl, heterocycloalkyl, substituted heterocycloalkyl, or the pharmaceutically acceptable salts thereof.

The present invention also provides compounds having the Formula VII

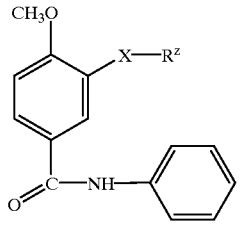

VII wherein
X is

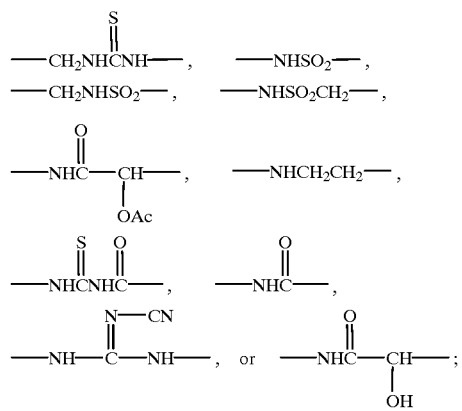

$R^Z$ is phenyl or phenyl substituted with from 1 to 5 substituents selected from halogen or —$CF_3$; or
X and $R^Z$ are —$N(SO_2$-3,5-dichlorophenyl$)_2$, or the pharmaceutically acceptable salts thereof.

The present invention also provides compounds having the Formula VIII

VIII

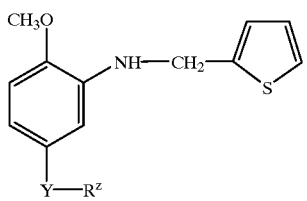

wherein
Y is

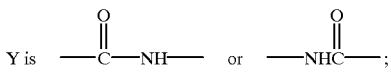

and
- $R^z$ is phenyl, pyridyl, or phenyl substituted with from 1 to 5 substituents wherein the substituents are selected from halogen, pyridyl, or $-CO_2C_1-C_6$ alkyl.

Also provided is a method of treating or preventing atherosclerosis, the method comprising administering to a patient having atherosclerosis or at risk of having atherosclerosis a therapeutically effective amount of a compound of Formula II.

Also provided is a method of treating or preventing inflammation, the method comprising administering to a patient having inflammation or at risk of having inflammation a therapeutically effective amount of a compound of Formula II.

Also provided is a method of inhibiting 15-lipoxygenase, the method comprising administering to a patient in need of 15-lipoxygenase inhibition a 15-lipoxygenase inhibiting amount of a compound of Formula II.

Also provided is a method of inhibiting the chemotaxis of monocytes, the method comprising administering to a patient in need of inhibition of chemotaxis of monocytes a chemotaxis inhibiting amount of a compound of Formula II.

The present invention provides a pharmaceutically acceptable composition comprising a compound of Formula II.

Also provided is a method of treating or preventing atherosclerosis, the method comprising administering to a patient having atherosclerosis or at risk of having atherosclerosis a therapeutically effective amount of a compound of Formula III.

Also provided is a method of treating or preventing inflammation, the method comprising administering to a patient having inflammation or at risk of having inflammation a therapeutically effective amount of a compound of Formula III.

Also provided is a method of inhibiting 15-lipoxygenase, the method comprising administering to a patient in need of 15-lipoxygenase inhibition a 15-lipoxygenase inhibiting amount of a compound of Formula III.

Also provided is a method of inhibiting the chemotaxis of monocytes, the method comprising administering to a patient in need of inhibition of chemotaxis of monocytes a chemotaxis inhibiting amount of a compound of Formula III.

The present invention also provides a pharmaceutically acceptable composition comprising a compound of Formula III.

Also provided is a method of treating or preventing atherosclerosis, the method comprising administering to a patient having atherosclerosis or at risk of having atherosclerosis a therapeutically effective amount of a compound of Formula IV.

Also provided is a method of treating or preventing inflammation, the method comprising administering to a patient having inflammation or at risk of having inflammation a therapeutically effective amount of a compound of Formula IV.

Also provided is a method of inhibiting 15-lipoxygenase, the method comprising administering to a patient in need of 15-lipoxygenase inhibition a 15-lipoxygenase inhibiting amount of a compound of Formula IV.

Also provided is a method of inhibiting the chemotaxis of monocytes, the method comprising administering to a patient in need of inhibition of chemotaxis of monocytes a chemotaxis inhibiting amount of a compound of Formula IV.

The present invention provides a pharmaceutically acceptable composition comprising a compound of Formula IV.

Also provided is a method of treating or preventing atherosclerosis, the method comprising administering to a patient having atherosclerosis or at risk of having atherosclerosis a therapeutically effective amount of a compound of Formula V.

Also provided is a method of treating or preventing inflammation, the method comprising administering to a patient having inflammation or at risk of having inflammation a therapeutically effective amount of a compound of Formula V.

Also provided is a method of inhibiting 15-lipoxygenase, the method comprising administering to a patient in need of 15-lipoxygenase inhibition a 15-lipoxygenase inhibiting amount of a compound of Formula V.

Also provided is a method of inhibiting the chemotaxis of monocytes, the method comprising administering to a patient in need of inhibition of chemotaxis of monocytes a chemotaxis inhibiting amount of a compound of Formula V.

The present invention also provides a pharmaceutically acceptable composition comprising a compound of Formula V.

Also provided is a method of treating or preventing atherosclerosis, the method comprising administering to a patient having atherosclerosis or at risk of having atherosclerosis a therapeutically effective amount of a compound of Formula VII.

Also provided is a method of treating or preventing inflammation, the method comprising administering to a patient having inflammation or at risk of having inflammation a therapeutically effective amount of a compound of Formula VII.

Also provided is a method of inhibiting 15-lipoxygenase, the method comprising administering to a patient in need of 15-lipoxygenase inhibition a 15-lipoxygenase inhibiting amount of a compound of Formula VII.

Also provided is a method of inhibiting the chemotaxis of monocytes, the method comprising administering to a patient in need of inhibition of chemotaxis of monocytes a chemotaxis inhibiting amount of a compound of Formula VII.

The present invention also provides a pharmaceutically acceptable composition comprising a compound of Formula VII.

Also provided is a method of treating or preventing atherosclerosis, the method comprising administering to a patient having atherosclerosis or at risk of having atherosclerosis a therapeutically effective amount of a compound of Formula VIII.

Also provided is a method of treating or preventing inflammation, the method comprising administering to a patient having inflammation or at risk of having inflammation a therapeutically effective amount of a compound of Formula VIII.

Also provided is a method of inhibiting 15-lipoxygenase, the method comprising administering to a patient in need of 15-lipoxygenase inhibition a 15-lipoxygenase inhibiting amount of a compound of Formula VIII.

Also provided is a method of inhibiting the chemotaxis of monocytes, the method comprising administering to a patient in need of inhibition of chemotaxis of monocytes a chemotaxis inhibiting amount of a compound of Formula VIII.

The present invention provides a pharmaceutically acceptable composition comprising a compound of Formula VIII.

The present invention provides the compounds:
3-Amino-4-methoxy-N-(3,4-dichlorophenyl)-benzamide;
3-(3-Trifluoromethyl-phenylamino)-4-methoxy-N-(4-fluorophenyl)-benzamide;
3-[3-(3,5-Dichlorophenyl)-thioureido]-4-methoxy-N-phenyl-benzamide;
4-[3-(2-Methoxy-5-phenylcarbamoyl-phenyl)-thioureido]-benzoic acid;
4-Methoxy-N-phenyl-3-(3-pyridin-3-yl-thioureido)-benzamide;
3-[3-(3,5-Dichlorophenyl)-thioureido]-N-(4-flourophenyl)-4-methoxy-benzamide;
3-(3,5-Dichloro-benzenesulfonylamino)-4-methoxy-N-phenyl-benzamide; or
3-Methanesulfonylamino-4-methoxy-N-(3,4-dichlorophenyl)-benzamide.

The present invention provides the compounds:
3-Amino-4-methoxy-N-(4-chlorophenyl)-benzamide,
3-Amino-4-methoxy-N-(3,4-dimethylphenyl)-benzamide;
3-Amino-4-methoxy-N-(4-methylphenyl)-benzamide;
3-Amino-4-methoxy-N-(4-fluorophenyl)-benzamide;
3-Amino-4-fluoro-N-phenyl-benzamide; or
3-Amino-4-ethoxy-N-phenyl-benzamide.

The present invention provides the compounds:
3-Amino-4-methoxy-N-(3,5-dimethylphenyl)-benzamide;
3-Amino-4-methoxy-N-(3-chloro-4-methylphenyl)-benzamide;
3-Amino-4-methoxy-N-(2,4-difluorophenyl)-benzamide;
3-Amino-4-methoxy-N-(3,4-difluorophenyl)-benzamide;
3-Amino-4-methoxy-N-(3-chlorophenyl)-benzamide;
3-Amino-4-ethyl-N-phenyl-benzamide;
3-Amino-4-ethyl-N-(3,4-dichlorophenyl)-benzamide;
3-Amino-4-ethyl-N-(3,4-difluorophenyl)-benzamide; or
3-Amino-4-methylsulfanyl-N-phenyl-benzamide.

The present invention provides the compounds:
N-(3-Amino-4-methoxyphenyl)-benzamide;
3,4-Dichloro-N-(3-amino-4-fluorophenyl)-benzamide;
3,4-Dichloro-N-(3-amino-4-methoxy-phenyl)-benzamide;
3-Phenylamino-N-phenyl-benzamide;
3-(3,5-Dichloro-phenylamino)-N-phenyl-benzamide;
3-(2-Methoxy-phenylamino)-N-phenyl-benzamide;
4-Methoxy-3-phenylamino-N-phenyl-benzamide;
3-(2-Methoxy-phenylamino)-4-methoxy-N-phenyl-benzamide; or
3-(3-Trifluoromethyl-phenylamino)-4-methoxy-N-phenyl-benzamide.

The present invention provides the compounds:
3-(3-Chloro-phenylamino)-4-methoxy-N-phenyl-benzamide;
3-(3-Methyl-phenylamino)-4-methoxy-N-phenyl-benzamide;
3-(3-Nitro-phenylamino)-4-methoxy-N-phenyl-benzamide;
3-(4-Methyl-phenylamino)-4-methoxy-N-phenyl-benzamide;
3-(3,5-Dichloro-phenylamino)-4-methoxy-N-phenyl-benzamide;
3-(3,5-Dimethyl-phenylamino)-4-methoxy-N-phenyl-benzamide;
3-Phenylamino-4-fluoro-N-phenyl-benzamide;
3-Phenylamino-4-methyl-N-phenyl-benzamide; or
3-Phenylamino-4-methoxy-N-(4-fluorophenyl)-benzamide.

The present invention provides the compounds:
4-Ethyl-3-(3-trifluoromethyl-phenylamino)-N-phenyl-benzamide;
4-Ethoxy-3-(3-trifluoromethyl-phenylamino)-N-phenyl-benzamide;
4-Methylsulfanyl-3-(3-trifluoromethyl-phenylamino)-N-phenyl-benzamide;
3-[4-(4,4-Dimethyl-4,5-dihydro-oxazol-2-yl)-phenylamino]-4-methoxy-N-phenyl-benzamide;
4-Methoxy-3-(3-trifluoromethyl-phenylamino)-N-(3-pyridyl)-benzamide;
4-Methoxy-3-(3,5-dimethyl-phenylamino)-N-(4-fluorophenyl)-benzamide;
4-Methoxy-3-(3-trifluoromethyl-phenylamino)-N-(3,4-dichlorophenyl)-benzamide;
4-Methoxy-3-(3-trifluoromethyl-phenylamino)-N-(3,4-difluorophenyl)-benzamide;
N-[3-(Phenylamino)-4-methoxy-phenyl]-benzamide; or
3-Benzylamino-4-methoxy-N-phenyl-benzamide.

The present invention provides the compounds:
3-(3,5-Dichloro-benzylamino)-4-methoxy-N-phenyl-benzamide,
3-(3,4-Dimethoxy-benzylamino)-4-methoxy-N-phenyl-benzamide;
3-Phenoxy-N-phenyl-benzamide;
3-Phenoxy-4-methoxy-N-phenyl-benzamide;
3-(Phenylamino)-4-methoxy-benzoic acid, phenyl ester;
4-Hydroxy-3-(3,5-dichloro-phenylamino)-N-phenyl-benzamide;
3-(3,5-Dichloro-phenylamino)-4-hydroxy-N-(4-methoxyphenyl)-benzamide;
3-(3,5-Dichloro-phenylamino)-4-hydroxy-N-(4-methylphenyl)-benzamide; or
3-(3,5-Dichloro-phenylamino)-4-hydroxy-N-(3-hydroxy-4-methoxyphenyl)-benzamide.

The present invention provides the compounds:
3-[3-(3-Chlorophenyl)-thioureido]-4-methoxy-N-phenyl-benzamide;
4-Methoxy-N-phenyl-3-(3-phenyl-thioureido)-benzamide;
4-Methoxy-N-phenyl-3-[3-(4-trifluoromethyl-phenyl)-thioureido]-benzamide;
3-[3-(4-tert-Butyl-phenyl)-thioureido]-4-methoxy-N-phenyl-benzamide;
3-[3-(4-Chlorophenyl)-thioureido]-4-methoxy-N-phenyl-benzamide;
3-[3-(3-Nitrophenyl)-thioureido]-4-methoxy-N-phenyl-benzamide;
4-Methoxy-N-phenyl-3-(3-benzoyl-thioureido)-benzamide;
4-Methoxy-N-phenyl-3-[3-(2,3,5,6-tetrafluoro-phenyl)-thioureido]-benzamide;
4-Methoxy-N-phenyl-3-(-3-p-tolyl-thioureido)-benzamide; or
3-[3-(3,5-Dichlorophenyl)-thioureido]-N-phenyl-benzamide.

The present invention provides the compounds:
3-[3-(3,5-Dichlorophenyl)-thioureido]-4-methyl-N-phenyl-benzamide;

3-[3-(3,4-Dimethoxyphenyl)-thioureido]-4-methoxy-N-phenyl-benzamide;
3-[3-(4-Chloro-3-trifluoromethylphenyl)-thioureido]-4-methoxy-N-phenyl-benzamide;
3-[3-(3-Cyanophenyl)-thioureido]-4-methoxy-N-phenyl-benzamide;
3-[3-(3-Acetyl-phenyl)-thioureido]-4-methoxy-N-phenyl-benzamide;
3-[3-(4-Chloro-3-nitrophenyl)-thioureido]-4-methoxy-N-phenyl-benzamide;
3-[3-(4-Fluorophenyl)-thioureido]-4-methoxy-N-phenyl-benzamide;
3-[3-(3,5-Dichlorophenyl)-thioureido]-4-methoxy-N-(4-methoxy-phenyl)-benzamide; or
3-[3-(3,5-Dichlorophenyl)-thioureido]-4-ethoxy-N-phenyl-benzamide.

The present invention provides the compounds:
4-[3-(2-Methoxy-5-phenylcarbamoyl-phenyl)-thioureido]-benzenesulfonic acid;
4-Methoxy-3-[3-(4-methoxy-phenyl)-thioureido]-N-phenyl-benzamide;
4-Methoxy-N-phenyl-3-[3-(3-trifluoromethyl-phenyl)-thioureido]-benzamide;
3-[3-(3,4-Dichlorophenyl)-thioureido]-4-methoxy-N-phenyl-benzamide,
1-{3-[3-(3,5-Dichlorophenyl)-thioureido]-4-methoxyphenyl}-3-phenyl-urea;
N-{3-[3-(3,5-Dichlorophenyl)-thioureido]-4-methoxyphenyl}-benzamide;
4-Methoxy-3-[3-(4-nitrophenyl)-thioureido]-N-phenyl-benzamide;
3-[3-(3,5-Bis-trifluoromethylphenyl)-thioureido]-4-methoxy-N-phenyl-benzamide; or
4-Methoxy-N-phenyl-3-[3-(4-sulfamoyl-phenyl)-thioureido]-benzamide.

The present invention provides the compounds:
N-(4-Chlorophenyl)-3-[3-(3,5-dichlorophenyl)thioureido]-4-methoxy-benzamide;
3-[3-(4-Dimethylaminophenyl)-thioureido]-4-methoxy-N-phenyl-benzamide;
3-[3-(3,5-Dichlorophenyl)-thioureido]-4-methoxy-N-p-tolyl-benzamide;
4-Methoxy-N-phenyl-3-(3-m-tolyl-thioureido)-benzamide;
3-[3-(3,5-Dichlorophenyl)-thioureido]-4-fluoro-N-phenyl-benzamide;
N-(3,4-Dichlorophenyl)-3-[3-(3,5-dichlorophenyl)-thioureido]-4-methoxy-benzamide;
4-Methoxy-N-phenyl-3-(3-o-tolyl-thioureido)-benzamide;
3-[3-(3,5-Dimethylphenyl)-thioureido]-4-methoxy-N-phenyl-benzamide; or
3-[3-(3,4-Dichlorophenyl)-thioureido]-4-methoxy-N-pyridin-3-yl-benzamide.

The present invention provides the compounds:
5-[3-(3,5-Dichlorophenyl)-thioureido]-2-fluoro-N-phenyl-benzamide;
N-(3,4-Dimethylphenyl)-4-methoxy-3-(3-m-tolyl-thioureido)-benzamide;
N-(-3,5-Dimethylphenyl)-4-methoxy-3-(3-m-tolyl-thioureido)-benzamide;
N-(3-Chloro-4-methylphenyl)-3-[3-(3,5-dichlorophenyl)-thioureido]-4-methoxy-benzamide;
N-(3,4-Dichlorophenyl)-4-methoxy-3-[3-(4-sulfamoyl-phenyl)-thioureido]-benzamide;
3-[3-(3,5-Dichlorophenyl)-thioureido]-4-methylsulfanyl-N-phenyl-benzamide;
3-[3-(3,5-Dichlorophenyl)-thioureido]-N-(3,4-difluoro-phenyl)-4-methoxy-benzamide;
N-(3-Chlorophenyl)-3-[3-(4-fluorophenyl)-thioureido]-4-methoxy-benzamide;
3-[3-(3,5-Dichlorophenyl)-thioureido]-4-methoxy-N-phenyl-benzenesulfonamide; or
4-Ethyl-N-phenyl-3-[3-(3-trifluoromethylphenyl)-thioureido]-benzamide.

The present invention provides the compounds:
4-Ethyl-N-(3,4-difluorophenyl)-3-[3-(3-trifluoromethylphenyl)-thioureido]-benzamide;
3-{3-[2-Methoxy-5-(pyridin-3-ylcarbamoyl)-phenyl]-thioureido}-benzoic acid;
3-[3-(2-Methoxy-5-phenylcarbamoyl-phenyl)-thioureido]-benzoic acid;
3,4-Dichloro-N-{4-fluoro-3-[3-(3-trifluoromethylphenyl)-thioureido]-phenyl}-benzamide;
3,4-Dichloro-N-{3-[3-(3,5-dichlorophenyl)-thioureido]-4-methoxyphenyl}-benzamide;
3-(3,5-Dichloro-benzenesulfonylamino)-4-methoxy-N-(3,4-difluorophenyl)-benzamide;
3-(3,5-Dichloro-benzenesulfonylamino)-4-methoxy-N-(3,4-dichlorophenyl)-benzamide; or
3-Benzenesulfonylamino-4-methoxy-N-phenyl-benzamide.

The present invention provides the compounds:
3-(4-Methoxy-benzenesulfonylamino)-4-methoxy-N-phenyl-benzamide;
3-(3-Nitro-benzenesulfonylamino)-4-methoxy-N-phenyl-benzamide;
3-(3-Chloro-benzenesulfonylamino)-4-methoxy-N-phenyl-benzamide;
3-(4-Methyl-benzenesulfonylamino)-4-methoxy-N-phenyl-benzamide;
3-(4-Fluoro-benzenesulfonylamino)-4-methoxy-N-phenyl-benzamide;
3-(4,5-Dibromo-thiophene-2-sulfonylamino)-4-methoxy-N-phenyl-benzamide;
3-(2-Chloro-benzenesulfonylamino)-4-methoxy-N-phenyl-benzamide;
3-(4-Trifluoromethyl-benzenesulfonylamino)-4-methoxy-N-phenyl-benzamide;
3-(Butane-1-sulfonylamino)-4-methoxy-N-phenyl-benzamide; or
3-(Quinoline-8-sulfonylamino)-4-methoxy-N-phenyl-benzamide.

The present invention provides the compounds:
3-(2-Acetylamino-4-methyl-thiazole-5-sulfonylamino)-4-methoxy-N-phenyl-benzamide;
3-(2,5-Dichloro-thiophene-3-sulfonylamino)-4-methoxy-N-phenyl-benzamide;
3-(Naphthalene-1-sulfonylamino)-4-methoxy-N-phenyl-benzamide;
3-Ethaenesulfonylamino-4-methoxy-N-phenyl-benzamide;
3-Phenylmethanesulfonylamino-4-methoxy-N-phenyl-benzamide,
3-(3,4-Dichloro-benzenesulfonylamino)-4-methoxy-N-phenyl-benzamide;
3-(2,4-Difluoro-benzenesulfonylamino)-4-methoxy-N-phenyl-benzamide;
3-(Toluene-3-sulfonylamino)-4-methoxy-N-phenyl-benzamide;
3-(4-Acetylamino-benzenesulfonylamino)-4-methoxy-N-phenyl-benzamide;
3-(Naphthalene-2-sulfonylamino)-4-methoxy-N-phenyl-benzamide;
3-(1-Methyl-1H-imidazole-4-sulfonylamino)-4-methoxy-N-phenyl-benzamide;
3-(Thiophene-2-sulfonylamino)-4-methoxy-N-phenyl-benzamide;

3-(5-Dimethylamino-naphthalene-1-sulfonylamino)-4-methoxy-N-phenyl-benzamide;
2-Methoxy-5-phenylcarbamoyl-carbonic acid-phenyl ester phenyl ester; or
4-Hydroxy-3-phenylamino-N-phenyl-benzamide.
The present invention provides the compounds:
3-(3-Amino-4-methoxy-benzoylamino)-benzoic acid ethyl ester;
3-(3-Amino-4-methoxy-benzoylamino)-benzoic acid methyl ester;
3,4-Difluoro-N-(3-amino-4-methoxy-phenyl)-benzamide;
3,4-Difluoro-N-(3-amino-4-fluoro-phenyl)-benzamide;
1-(3-Amino-4-methoxy-phenyl)-3-(3,4-dichloro-phenyl)-urea;
3-(4-Fluoro-phenylamino)-4-methoxy-N-phenyl-benzamide; or
3-(3,5-Dichloro-phenylamino)-4-methoxy-N-(4-fluoro-phenyl)-benzamide.
The present invention provides the compounds:
3-(4-Fluoro-phenylamino)-4-methoxy-N-(4-fluoro-phenyl)-benzamide;
3-[4-Methoxy-3-(3-trifluoromethyl-phenylamino)-benzoylamino]-benzoic acid methyl ester;
3-[4-Methoxy-3-(3-trifluoromethyl-phenylamino)-benzoylamino]-benzoic acid ethyl ester;
4-Trifluoromethoxy-3-(3-trifluoromethyl-phenylamino)-N-phenyl-benzamide;
4-Trifluoromethoxy-3-(3-trifluoromethyl-phenylamino)-N-(4-fluoro-phenyl)-benzamide;
3,4-Dichloro-N-[4-methoxy-3-(3-trifluoromethyl-phenylamino)-phenyl]-benzamide;
3-[3-(2-Methoxy-5-phenylcarbamoyl-phenyl)-thioureido]-benzoic acid methyl ester;
3-{3-[5-(3,4-Difluoro-phenylcarbamoyl)-2-methoxy-phenyl]-thioureido}-benzoic acid;
3-[3-(3,5-Dichloro-phenyl)-thioureido]-4-trifluoromethoxy-N-(4-fluoro-phenyl)-benzamide; or
3-[3-(3-trifluoromethyl-phenyl)-thioureido]-4-trifluoromethoxy-N-(4-fluoro-phenyl)-benzamide.
The present invention provides the compounds:
4-{3-[5-(3,4-Difluoro-phenylcarbamoyl)-2-methoxy-phenyl]-thioureido}-benzenesulfonic acid;
4-{3-[5-(4-Fluoro-phenylcarbamoyl)-2-methoxy-phenyl]-thioureido}-benzoic acid;
3-{3-[5-(4-Fluoro-phenylcarbamoyl)-2-methoxy-phenyl]-thioureido}-benzoic acid;
4-{3-[5-(3,4-Difluoro-benzoylamino)-2-methoxy-phenyl]-thioureido}-benzoic acid;
3-{3-[5-(3,4-Difluoro-benzoylamino)-2-methoxy-phenyl]-thioureido}-benzoic acid;
N-{3-[3-(3,5-Dichloro-phenyl)-thioureido]-4-fluoro-phenyl}-3,4-difluoro-benzamide;
1-(3,4-Dichloro-phenyl)-3-{3-[3-(3,5-dichloro-phenyl)-thioureido]-4-methoxy-phenyl}-urea;
3-(3-{5-[3-(3,4-Dichloro-phenyl)-ureido]-2-methoxy-phenyl}-thioureido)-benzoic acid methyl ester;
3-(3-{5-[3-(3,4-Dichloro-phenyl)-ureido]-2-methoxy-phenyl}-thioureido)-benzoic acid; or
1-{3-[3-(3,5-Bis-trifluoromethyl-phenyl)-thioureido]-4-methoxy-phenyl}-3-(3,4-dichloro-phenyl)-urea.
The present invention provides the compounds:
1-{3-[3-(4-Chloro-3-nitro-phenyl)-thioureido]-4-methoxy-phenyl}-3-(3,4-dichloro-phenyl)-urea;
3-[3-(3,5-Dichloro-phenyl)-thioureido]-4-methoxy-benzoic acid benzyl ester;
3-(Dodecane-1-sulfonylamino)-4-methoxy-N-phenyl-benzamide;
4-Methoxy-3-(octane-1-sulfonylamino)-N-phenyl-benzamide;
3-(Decane-1-sulfonylamino)-4-methoxy-N-phenyl-benzamide;
3-(3-Nitro-benzenesufonylamino)-4-methoxy-N-(3,4-difluoro-phenyl)-benzamide;
3,5-Dichloro-N-{5-[3-(3,4-dichloro-phenyl)-ureido]-2-methoxy-phenyl}-benzenesulfonamide;
3-(1-Methylethyl-1-sulfonylamino)-4-methoxy-N-phenyl-benzamide;
4-(2-Methoxy-5-phenylcarbamoyl-phenylsulfamoyl)-benzoic acid; or
3-(Octadecane-1-sulfonylamino)-4-methoxy-N-phenyl-benzamide.
The present invention provides the compounds:
3-(3-Amino-benzenesulfonylamino)-4-methoxy-N-(3,4-difluoro-phenyl)-benzamide;
4-Methoxy-3-(4-nitro-benzenesulfonylamino)-N-(3,4-difluoro-phenyl)-benzamide;
3-(4-Cyano-benzenesulfonylamino)-4-methoxy-N-(3,4-difluoro-phenyl)-benzamide;
4-Methoxy-3-(4-nitro-benzenesulfonylamino)-N-phenyl-benzamide;
3-(3-Cyano-benzenesulfonylamino)-4-methoxy-N-(4-fluoro-phenyl)-benzamide;
4-Methoxy-3-(3-nitro-benzenesulfonylamino)-N-(4-fluoro-phenyl)-benzamide;
4-Methoxy-3-(4-nitro-benzenesulfonylamino)-N-(4-fluoro-phenyl)-benzamide;
3-(4-Cyano-benzenesulfonylamino)-4-methoxy-N-phenyl-benzamide;
3-(4-Cyano-benzenesulfonylamino)-4-methoxy-N-(4-fluoro-phenyl)-benzamide; or
3-(Dodecane-1-sulfonylamino)-4-methoxy-N-(3,4-dichloro-phenyl)-benzamide.
The present invention provides the compounds:
3-(3-Cyano-benzenesulfonylamino)-4-methoxy-N-phenyl-benzamide;
3,4-Dichloro-N-[4-methoxy-3-(4-methoxy-benzenesulfonylamino)-phenyl]-benzamide;
3,4-Dichloro-N-[4-methoxy-3-(toluene-4-sulfonylamino)-phenyl]-benzamide;
3,4-Difluoro-N-[4-methoxy-3-(3-amino-benzenesulfonylamino)-phenyl]-benzamide;
3,4-Difluoro-N-[4-methoxy-3-(4-amino-benzenesulfonylamino)-phenyl]-benzamide;
3,4-Difluoro-N-[4-methoxy-3-(1-dodecane-sulfonylamino)-phenyl]-benzamide;
3,4-Difluoro-N-[4-methoxy-3-(chloromethyl-sulfonylamino)-phenyl]-benzamide;
3,4-Difluoro-N-[4-methoxy-3-(4-nitro-benzenesulfonylamino)-phenyl]-benzamide;
3,4-Difluoro-N-[4-methoxy-3-(3-nitro-benzenesulfonylamino)-phenyl]-benzamide; or
3,4-Difluoro-N-[3-(4-cyano-benzenesulfonylamino)-4-methoxy-phenyl]-benzamide.
The present invention provides the compounds:
3,4-Difluoro-N-[3-(3-cyano-benzenesulfonylamino)-4-methoxy-phenyl]-benzamide;
3,4-Difluoro-N-[4-fluoro-3-(thiophene-2-sulfonylamino)-phenyl]-benzamide;
Thiophene-2-sulfonic acid{5-[3-(3,4-dichloro-phenyl)-ureido]-2-methoxy-phenyl}-amide;
3-(3,5-Dichloro-benzenesulfonylamino)-4-methoxy-N-phenyl-thiobenzamide;
3,5-Dichloro-N-(2-methoxy-5-phenylaminomethyl-phenyl)-benzenesulfonamide;

3-(3-Hydroxy-benzylamino)-4-methoxy-N-(3,4-difluoro-phenyl)-benzamide;
3-(4-Diethylamino-benzylamino)-4-methoxy-N-phenyl-benzamide;
3-(3-Fluoro-benzylamino)-4-methoxy-N-(3,4-difluoro-phenyl)-benzamide;
3-(3-Hydroxy-benzylamino)-4-methoxy-N-phenyl-benzamide; or
4-Methoxy-3-(3-fluoro-benzylamino)-N-phenyl-benzamide.

The present invention provides the compounds:
4-Methoxy-3-(3-nitro-benzylamino)-N-phenyl-benzamide;
4-Methoxy-3-(4-methoxy-benzylamino)-N-phenyl-benzamide;
4-Methoxy-3-[(naphthalen-1-ylmethyl)-amino]-N-phenyl-benzamide;
4-Methoxy-3-(3,5-dimethyl-benylamino)-N-phenyl-benzamide;
3-(2,3-Difluoro-benzylamino)-4-methoxy-N-phenyl-benzamide;
Acetic acid 4-[(2-methoxy-5-phenylcarbamoyl-phenylamino)-methyl]-phenyl ester;
4-[(2-Methoxy-5-phenylcarbamoyl-phenylamino)-methyl]-benzoic acid methyl ester;
3-[(Furan-3-ylmethyl)-amino]-4-methoxy-N-phenyl-benzamide;
4-Methoxy-3-(2-methyl-benzylamino)-N-phenyl-benzamide; or
4-Methoxy-3-(4-fluoro-benzylamino)-N-phenyl-benzamide.

The present invention provides the compounds:
3-(4-Hydroxy-3-nitro-benzylamino)-4-methoxy-N-phenyl-benzamide;
3-(4-Diethylamino-benzylamino)-4-methoxy-N-(3,4-difluoro-phenyl)-benzamide;
3-Benzylamino-4-methoxy-N-(3,4-difluoro-phenyl)-benzamide;
3-(3-Hydroxy-4-nitro-benzylamino)-4-methoxy-N-phenyl-benzamide;
3-(3-Cyano-benzylamino)-4-methoxy-N-phenyl-benzamide;
3-{[5-(3,4-Difluoro-phenylcarbamoyl)-2-methoxy-phenylamino]-methyl}-benzoic acid;
3-(3-Chloro-benzylamino)-4-methoxy-N-phenyl-benzamide;
3-(4-tert-Butyl-benzylamino)-4-methoxy-N-phenyl-benzamide;
3-(4-Cyano-benzylamino)-4-methoxy-N-phenyl-benzamide; or
4-{[5-(3,4-Difluoro-phenylcarbamoyl)-2-methoxy-phenylamino]-methyl}-benzoic acid.

The present invention provides the compounds:
4-Methoxy-3-(4-propoxy-benzylamino)-N-phenyl-benzamide;
3-[(Biphenyl-4-ylmethyl)-amino]-4-methoxy-N-phenyl-benzamide;
4-Methoxy-3-(4-methyl-benzylamino)-N-phenyl-benzamide;
4-Methoxy-3-(2-methoxy-benzylamino)-N-phenyl-benzamide;
3-(4-Butyl-benzylamino)-4-methoxy-N-phenyl-benzamide;
3-(3-Fluoro-benzylamino)-4-methoxy-N-(3,4-dichloro-phenyl)-benzamide;
3-[(2-Methoxy-5-phenylcarbamoyl-phenylamino)-methyl]-benzoic acid;
3-(3,4-Dimethyl-benzylamino)-4-methoxy-N-phenyl-benzamide;
3-(4-Isopropyl-benzylamino)-4-methoxy-N-phenyl-benzamide; or
3,4-Dichloro-N-[3-(3-fluoro-benzylamino)-4-methoxy-phenyl]-benzamide.

The present invention provides the compounds:
3,4-Difluoro-N-[3-(3-hydroxy-benzylamino)-4-methoxy-phenyl]-benzamide;
3-{[5-(3,4-Difluoro-benzoylamino)-2-methoxy-phenylamino]-methyl}-benzoic acid;
3-[3-(3,5-Dichloro-phenyl)-thioureidomethyl]-4-methoxy-N-phenyl-benzamide;
3-(3,5-Dichloro-benzenesulfonylamino)-4-methoxy-N-phenyl-benzamide;
3-[(3,5-Dichloro-benzenesulfonylamino)-methyl]-4-methoxy-N-phenyl-benzamide;
4-Methoxy-3-phenylmethanesulfonylamino-N-phenyl-benzamide;
3-[Bis[(3,5-dichlorophenyl)sulfonyl]amino]-4-methoxy-N-phenyl-benzamide;
(2-Methoxy-5-phenylcarbamoyl-phenylcarbamoyl)-acetic acid phenylmethyl ester;
4-Methoxy-N-phenyl-3-[2-(3-trifluoromethyl-phenyl)-ethylamino]-benzamide; or
4-Methoxy-3-[3-(3-nitro-phenyl)-thioureido]-N-phenyl-benzamide.

The present invention provides the compounds:
3-[(3,5-Dichlorobenzoyl)-amino]-4-methyl-N-phenyl-benzamide;
3-[[(Cyanoimino)[(3,5-dichlorophenyl)amino]methyl)amino]-4-methoxy-N-phenyl-benzamide;
3-(2-Hydroxy-2-phenyl-acetylamino)-4-methoxy-N-phenyl-benzamide;
4-Methoxy-3-[(thiophen-2-ylmethyl)-amino]-N-(3,4-difluoro-phenyl)-benzamide;
4-Methoxy-3-[(thiophen-2-ylmethyl)-amino]-N-phenyl-benzamide;
4-Methoxy-3-[(thiophen-2-ylmethyl)-amino]-N-(4-fluoro-phenyl)-benzamide;
4-Methoxy-3-[(thiophen-2-ylmethyl)-amino]-N-(3,4-dichloro-phenyl)-benzamide;
4-Methoxy-3-[(thiophen-2-ylmethyl)-amino]-N-pyridin-3-yl-benzamide;
4-{4-Methoxy-3-[(thiophen-2-ylmethyl)-amino]-benzoylamino}-benzoic acid ethyl ester;
3,4-Dichloro-N-{4-methoxy-3-[(thiophen-2-ylmethyl)-amino]-phenyl}-benzamide; or
3,4-Difluoro-N-{4-methoxy-3-[(thiophen-2-ylmethyl)-amino]-phenyl}-benzamide.

The present invention provides the compounds:
3-[(Benzo[1,3]dioxol-5-ylmethyl)-amino]-4-methoxy-N-phenyl-benzamide;
4-Methoxy-3-(3,5-difluoro-benzylamino)-N-phenyl-benzamide;
3-(4-Dimethylamino-benzylamino)-4-methoxy-N-phenyl-benzamide;
4-Methoxy-3-(3-trifluoromethyl-benzylamino)-N-phenyl-benzamide;
4-Methoxy-3-(2-fluoro-benzylamino)-N-phenyl-benzamide;
N-{3-[(2,3-Dihydro-benzo[1,4]dioxin-6-ylmethyl)-amino]-4-methoxy-phenyl}-benzamide;
3-(4-Hydroxy-benzylamino)-4-methoxy-N-phenyl-benzamide;
4-Methoxy-3-(3-methyl-benzylamino)-N-phenyl-benzamide; or
3-(3,4-Difluoro-benzylamino)-4-methoxy-N-phenyl-benzamide.

The present invention provides the compounds:
3-[(Pyridin-3-ylmethyl)-amino]-4-methoxy-N-phenyl-benzamide;
3-[(Pyridin-3-ylmethyl)-amino]-4-methoxy-N-(3,4-difluoro-phenyl)-benzamide;
3-[(Pyridin-3-ylmethyl)-amino]-4-methoxy-N-(3,4-dichloro-phenyl)-benzamide;
4-[(2-Methoxy-5-phenylcarbamoyl-phenylamino)-methyl]-benzoic acid;
3,4-Difluoro-N-{[3-(pyridin-3-ylmethyl)-amino]-4-methoxy-phenyl}-benzamide; or
3-(3-Acetylamino-phenylamino)-4-methoxy-N-phenyl-benzamide.

DETAILED DESCRIPTION OF THE INVENTION

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl. Preferably the alkyl group contains from 1 to 6 carbon atoms.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The term "substituted" means that the base organic radical has one or more substituents. For example, substituted cyclohexyl means a cyclohexyl radical that has one or more substituents. Substituents include, but are not limited to, halogen, $C_1$–$C_8$ alkyl, —CN, $CF_3$, —$NO_2$, —$NH_2$, —$NHC_1$–$C_8$alkyl, —$N(C_1$–$C_8$alkyl$)_2$, —$OC_1$–$C_8$ alkyl, and —OH.

The term "heterocycle" means a cycloalkyl group wherein one or more atom is replaced with a heteroatom. Examples of heterocycles include, but are not limited to, pyrrolidinyl, piperidinyl, and piperazinyl.

The symbol "—" means a bond.

The term "patient" means all animals including humans. Examples of patients include humans, cows, dogs, cats, goats, sheep, and pigs.

Those skilled in the art are easily able to identify patients having atherosclerosis and inflammation.

A therapeutically effective amount is an amount of a compound of the present invention that when administered to a patient ameliorates a symptom of atherosclerosis or inflammation.

The compounds of the present invention can be administered to a patient either alone or as part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term salts refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts and the like. These may include cations based on the alkali and alkaline earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., Pharmaceutical Salts, *J. Pharm. Sci.,* 1977;66:1–19, which is incorporated herein by reference).

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, Pro-drugs as Novel Delivery Systems, Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kg of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well known to those skilled in the art.

The scope of the present invention includes compounds that are synthesized by standard techniques used organic synthesis and known to those skilled in the art, including combinatorial chemistry, or by biological mechanisms, including digestion and metabolism.

The examples presented below are intended to illustrate particular embodiments of the invention and are not intended to limit the scope of the specification, including the claims, in any way.

EXAMPLES

The following abbreviations are used throughout the present application:

| THF | tetrahydrofuran |
|---|---|
| PBS | phosphate buffered saline |
| APCI | atmosphere pressure chemical ionization |
| m.p. | melting point |
| CI | chemical ionization |
| HPODE | hydroperoxyoctadecadienoate |
| HODE | hydroxyoctadecadienoate |

Biological Examples

Rabbit Reticulocyte 15-LO Assay (h15LO)

The present 15-LO assay takes advantage of the ability of 15-LO to oxidize the fatty acid linoleic acid to the hydroperoxy fatty acid 13-(S)HPODE, resulting in the formation of a conjugated diene. The 15-LO inhibitors are incubated with 15-LO enzyme in the presence of linoleic acid substrate. The initial reaction is compared to an uninhibited (maximal) reaction to yield % inhibition. The 13-(S)HPODE produced in the reaction is reduced to the more stable corresponding hydroxy fatty acid, 13-hydroxyoctadecadienoate (13-HODE). This prevents artificial nonenzyme lipid peroxidation and product breakdown in the sample. 13-HPODE is quantitated by comparing peak areas of individual samples with those from a standard curve generated using authentic 13-HODE. This assay is performed using 2U of rabbit reticulocyte 15-LO in the presence of 174 μM linoleic acid. The reaction is incubated for 15 minutes at 4° C. The total reaction volume is 100 μL in PBS containing 0.2% Na cholate. The reaction is stopped with 100 μL of mobile phase and 10 μL of triethyl phosphite, which reduces the 13-HPODE to the more stable 13-HODE.

Fifteen-lipoxygenase was obtained from phenylhydrazine-treated rabbits and purified per the method of Rapoport (Rapoport S. M., Schewe T., Wiesner R., et al. The lipoxygenase of reticulocytes. Purification, characterization, and biological dynamics of the lipoxygenase; its identity with the respiratory inhibitors of the reticulocyte. *European Journal of Biochemistry,* 1979;96:545–561). The following chemicals were purchased and used as received: linoleic acid (NUJCheck Prep), 13-HPODE (Biomol Research Labs), sodium cholate (Sigma), trimethyl phosphite (Fluka Chemicals).

Monocyte Recruitment Assay

The recruitment or chemotaxis of monocytes was assayed by methods well known to those skilled in the art. In particular, the method set forth in *J. Clin. Invest.,* 1988;82:1853–1863, which is hereby incorporated by reference, was used.

Synthetic Examples

The compounds of the invention which are diarylamines can be prepared by reacting an aminobenzanilide with an appropriately substituted triarylbismuthine in a solvent such as ether, tetrahydrofuran, dichloromethane, chloroform, or the like. The reaction time is 1 hour to 96 hours, generally 4 hours, at a temperature from 20° C. to 70° C., preferably 40° C. to 50° C., in the presence of an organic base and a copper salt. The organic base can be chosen from any of a number such as pyridine, DABCO, DBU, trialkylamine, diisopropyl-ethylamine, etc., preferably triethylamine. The copper salt can be a copper(I) or copper(II) species, or even copper itself, but is preferably copper(II) acetate. The reaction requires at least a stoichiometric amount of each of the reagents but they may be employed in large excess; typically an approximately equimolar amount of each is employed. The triarylbismuth reagents may be triaryl Bi(III) or Bi(V) compounds, the latter being also the dihalo- or diacyl-species, with the tris(substituted-phenyl)bismuthines being preferred.

The required triarylbismuthines are either commercially available or prepared from commercially available materials using methods known in the literature, for example by reacting a Grignard reagent with Bi(III) chloride in THF.

Alternatively, the compounds of this type can be prepared by the well-known Ullmann reaction, in which an aminobenzanilide is reacted with an appropriately substituted aryl halide, such as a bromo- or iodobenzene in the presence of a base such as potassium carbonate or sodium carbonate or an organic base like N-ethylmorpholine, and a copper salt as described above, in a high-boiling solvent such as xylene, toluene, mesitylene, DMF, or DMA. The reaction is typically carried out at a temperature between 100° C. to 200° C., preferably 150° C. to 160° C. The concentrations of the reagents is not critical; typically a 2- to 5-fold excess of the reagents relative to the benzanilide is utilized, and the reaction time extends from 3 hours to 5 days, depending on the substituents present on the aromatic rings.

The aminobenzanilides required are either commercially available or are prepared by methods well-known in the chemical literature.

The thioureas of this invention may be prepared in various ways, all of which are well-known in the art. A convenient method of preparing the thioureas in this patent is to react a substituted aminobenzanilide with a substituted phenyl-isothiocyanate in a nonpolar aprotic solvent such as THF, ethyl acetate, ether, dichloromethane, or dioxane for from about 2 hours to 3 days at from about 0 degrees to about 70 degrees. The resulting product is collected by filtration or is obtained by concentration of the reaction mixture and then collected by filtration.

Isothiocyanates of various types are well-known and widely available to practitioners of the art.

The sulfonamides of this invention can be prepared using procedures well-known in the art. In a typical preparation, an aminobenzanilide is reacted with a sulfonyl chloride in equimolar proportions either neat or in a nonreactive organic solvent such as dichloromethane, tetrahydrofuran, toluene, dioxane or the like in the presence of a base such as trialkylamine, pyridine, DABCO, or DBU, over a wide range of temperatures typically from 0 degrees to about 150 degrees and a time period of 5 minutes to 5 days, followed by a workup procedure well-known to practitioners of the art. The molar ratios of the reactants are not critical but for the compounds of this invention equimolar ratios are preferred. Likewise, the sulfonamides of this invention are preferably prepared using pyridine as solvent with a reaction time of approximately 3 days at room temperature.

The required sulfonyl chlorides are in general commercially available or are readily prepared by methods well-known in the chemical literature.

Starting Materials

The benzoic acids, benzaldehydes, and anilines used in the following Examples are obtained from commercial suppliers, for example, Aldrich Chemical Company. 3-Amino-4-methoxy-benzanilide is obtained from Apin or Pfaltz & Bauer. Triphenylbismuth is obtained from Alfa. The other tris(aryl)-bismuthines are prepared using procedures described in the following references:

| | |
|---|---|
| Tris(2-methoxyphenyl)bismuthine | CA 111(1989): 154111j |
| Tris(3-methylphenyl)bismuthine | ibid. |
| Tris(3-chlorophenyl)bismuthine | Synthesis 1994: 775 |
| Tris(3-trifluoromethylphenyl)bismuthine | ibid. |
| Tris(4-methylphenyl)bismuthine | J. Coord. Chem., 1982; 12(1): 53–57 |
| Tris[4-(4,4-dimethyl-2-oxazolino)-phenyl]-bismuthine | International Patent Publication Number WO 96/22994, Aug 1, 1996 |
| Tris(3,5-dimethylphenyl)bismuthine | Can be prepared in accordance with the procedure set forth in Synthesis, 1994: 775, except using the Grignard reagent as described in J. Organomet Chem., 1994; 468(1–2): 37 |

Example 1

3-Amino-4-methyl-N-phenyl-benzamide

Step A: 4-Methyl-3-nitro-N-phenyl-benzamide

Oxalyl chloride (3 mL, 35 mmol) was added dropwise to a stirred solution of 3-nitro-4-methylbenzoic acid (5.0 g, 28 mmol) in a mixture of tetrahydrofuran or dichloromethane (125 mL) and dimethylformamide (1/2 mL) under $N_2$ at ice bath temperature. The mixture was allowed to warm to room temperature. After 1 hour, the solvent was removed by rotary evaporator under reduced pressure. The residue was redissolved in fresh tetrahydrofuran (100 mL) and recooled to ice bath temperature under $N_2$, while a solution of aniline (5.2 g, 56 mmol) in tetrahydrofuran (25 mL) was added dropwise. After 16 hours of stirring at room temperature, the mixture was concentrated to half-volume by rotary evaporator and the residue stirred in water (200 mL). After several hours, the precipitate was filtered off, rinsed three times with water, and dried to afford the product (6.8 g); m.p. 147–148° C.

Calculated for $C_{14}H_{12}N_2O_3$: C, 65.62; H, 4.72; N, 10.93. Found: C, 65.45; H, 4.64; N, 10.87.

Step B: 3-Amino-4-methyl-N-phenyl-benzamide

Raney nickel (1 g) was added to a solution of 3-nitro-4-methyl-N-phenyl-benzamide (6.2 g, 24 mmol) in a mixture of tetrahydrofuran (50 mL) and methanol (100 mL) and shaken at room temperature under an atmosphere of hydrogen, initially at a pressure of 50 psi, until the required amount of hydrogen was taken up. The catalyst was removed by filtration, and the filtrate was stripped of solvent by rotary evaporator. The residue was dried under reduced pressure to afford the pure product (5.5 g); m.p. 149–151° C.

Calculated for $C_{14}H_{14}N_2O$: C, 74.31; H, 6.24; N, 12.38. Found: C, 74.09; H, 6.20; N, 12.17.

Example 2

3-Amino-4-methoxy-N-(4-chlorophenyl)-benzamide

Prepared according to the procedure described for Example 1 using oxalyl chloride (5.5 mL, 63.05 mmol), 4-methoxy-3-nitrobenzoic acid (11.30 g, 57.32 mmol), dimethylformamide (1.0 mL, 1.29 mmol), and 4-chloroaniline (14.6 g, 114 mmol) to afford the product (4.4 g); m.p. 191–192° C.

Calculated for $C_{14}H_{13}N_2O_2Cl$: C, 60.77; H, 4.74; N, 10.12. Found: C, 60.71; H, 4.67; N, 10.03.

Example 3

3-Amino-4-methoxy-N-(4-methoxyphenyl)-benzamide

Prepared according to the procedure described for Example 1 using oxalyl chloride (3.0 mL, 34.39 mmol), 4-methoxy-3-nitrobenzoic acid (5.00 g, 25.36 mmol), dimethylformamide (0.5 mL, 6.5 mmol), and 4-methoxyaniline (6.25 g, 50.7 mmol) to afford the product (4.45 g); m.p. 164–167° C.

Calculated for $C_{14}H_{16}N_2O_3$: C, 66.16; H, 5.92; N, 10.29. Found: C, 66.21; H, 5.73; N, 10.35.

Example 4

3-Amino-4-methoxy-N-(3,4-dichlorophenyl)-benzamide

Prepared according to the procedure described for Example 1 using oxalyl chloride (5.0 mL, 57.31 mmol), 3-nitro-4-methoxybenzoic acid (5.04 g, 25.56 mmol), dimethylformamide (0.5 mL, 6.46 mmol), and 3,4-dichloroaniline (8.3 g, 51 mmol) to afford the product (5.45 g); m.p. 179–182° C.

Calculated for $C_{14}H_{12}N_2O_2Cl_2$: C, 54.04; H, 3.89; N, 9.00. Found: C, 53.30; H, 3.76; N, 8.83.

Example 5

3-Amino-4-methoxy-N-(3pyridyl)-benzamide

Prepared according to the procedure described for Example 1 using oxalyl chloride (2.0 mL, 22.93 mmol), 4-methoxy-3-nitrobenzoic acid (4.00 g, 20.29 mmol), dimethylformamide (0.5 mL, 6.46 mmol), and 3-aminopyridine (3.83 g, 40.69 mmol) to afford the product (3.98 g); m.p. 193–196° C.

Calculated for $C_{13}H_{13}N_3O_2 \cdot 0.25$ M MeOH: C, 63.33; H, 5.62; N, 16.73. Found: C, 63.33; H, 5.41; N, 16.88.

Example 6

3-Amino-4-methoxy-N-(3,4-dimethylphenyl)-benzamide

Prepared according to the procedure described for Example 1 using oxalyl chloride (3.0 mL, 34.4 mmol), 4-methoxy-3-nitrobenzoic acid (5.00 g, 25.36 mmol), dimethylformamide (1.0 mL, 12.92 mmol), and 3,4-dimethylaniline (6.2 g, 51 mmol) to afford the product (5.99 g), m.p. 138–142° C.

Calculated for $C_{16}H_{18}N_2O_2$: C, 71.09; H, 6.71; N, 10.36. Found: C, 70.63; H, 6.79; N, 10.28.

Example 7

3-Amino-4-methoxy-N-(4-methylphenyl)-benzamide

Oxalyl chloride (5.8 mL, 66.49 mmol) was added dropwise to a solution of 4-methoxy-3-nitrobenzoic acid (13.00 g, 65.94 mmol) and dimethylformamide (1.5 mL, 1.94 mmol) in tetrahydrofuran (250 mL) at ice bath temperature under a nitrogen atmosphere. The reaction was stirred overnight and allowed to gradually warm to room temperature. The solvent was removed in vacuo. The residue was triturated with hexanes and filtered to obtain 15.68 g of an off-white solid (acid chloride). The acid chloride (5.00 g, 23.19 mmol) was dissolved in tetrahydrofuran (250 mL) and cooled to ice bath temperature under a nitrogen atmosphere while 4-toluidine (14.6 g, 132 mmol) in of tetrahydrofuran (50 mL) was added. The reaction was stirred overnight and allowed to warm to room temperature. The solvent was concentrated to a volume of 125 mL and diluted with ethyl acetate (125 mL). The organic layer was washed with 1N HCl, 1N NaOH, brine (2×40 mL), dried ($MgSO_4$), filtered, and evaporated. The solid was triturated with hexanes and collected by filtration to give 1.23 g of the nitrobenzamide. The benzamide (1.06 g, 3.71 mmol) was reduced according to the procedure described for Example 1, Step B to afford the product (0.89 g); m.p. 190–194° C.

Calculated for $C_{15}H_{16}N_2O$ 2.0.1 M $H_2O$: C, 69.80; H, 6.33; N, 10.68. Found: C, 69.69; H, 6.11; N, 10.77.

Example 8

3-Amino-4-methoxy-N-(4-fluorophenyl)-benzamide

Prepared according to the procedure described for Example 7 using oxalyl chloride (3.0 mL, 34.39 mmol), 4-methoxy-3-nitrobenzoic acid (5.00 g, 25.36 mmol), dimethylformamide (0.5 mL, 6.5 mmol), and 4-fluroaniline (5.0 mL, 52.78 mmol) to afford the product (4.45 g); m.p. 164–167° C.

Calculated for $C_{14}H_{13}N_2O_2F$: C, 64.61; H, 5.03; N, 10.76. Found: C, 64.43; H, 4.95; N, 10.71.

Example 9

3-Amino-4-fluoro-N-phenyl-benzamide

Step A: 3-Nitro-4-fluoro-N-phenyl-benzamide

Dicyclohexylcarbodiimide (13.4 g, 65 mmol) was added to a mixture of 4-fluoro-3-nitrobenzoic acid (11.21 g, 61 mmol), 1-hydroxybenzotriazole hydrate (8.72 g, 65 mmol), aniline (6.3 g, 68 mmol), and dimethylformamide (200 mL) all at once (exotherm), and the mixture was stirred at room temperature overnight. The reaction mixture was filtered, the solvent was removed by rotary evaporator (70° C.), and the residue taken up in ethyl acetate (300 mL). The ethyl acetate solution was washed with water (3×200 mL), dried (magnesium sulfate), filtered, and stripped of solvent to leave an orange solid residue. The solid was recrystallized from hexane/ethyl acetate and used without further purification in the next step. Filtration through silica gel, eluting with dichloromethane/methanol 95:5 afforded an analytical sample; m.p. 155–157° C.

Calculated for $C_{13}H_9FN_2O_3$: C, 60.00; H, 3.49; N, 10.76. Found: C, 59.94; H, 3.48; N, 10.69.

Step B: 3-Amino-4-fluoro-N-phenyl-benzamide

Zinc dust (14 g) was added to a solution of 4-fluoro-3-nitro-N-phenyl-benzamide (1.99 g, 7.6 mmol) in acetic acid (80 mL) at 0° C. The mixture was stirred and allowed to warm to room temperature. After 4 hours, the mixture was filtered and the residue washed with ethyl acetate. The filtrate and washings were combined and taken to dryness by rotovap and the residue partitioned between ethyl acetate (200 mL) and saturated aqueous $NaHCO_3$. The organic layer was washed with saturated brine, dried over $MgSO_4$, filtered, and stripped of solvent. The residue was triturated in ethyl acetate/hexane and the suspended solid filtered off to afford the product (1.55 g); m.p. 167–170° C.

Calculated for $C_{13}H_{11}FN_2O$ : C, 67.82; H, 4.82; N, 12.17. Found: C, 67.76; H, 4.70; N, 12.06.

Example 10

3-Amino-4-ethoxy-N-phenyl-benzamide

Step A: 3-Nitro-4-ethoxy-N-phenyl-benzamide

4-Fluoro-3-nitro-N-phenyl-benzamide from Example 9 (2.34 g, 9 mmol) was added all at once to a solution prepared by dissolving sodium metal (2.29 g, 100 mmol) in ethanol (100 mL). The reaction mixture was stirred 1 hour at room temperature, then citric acid solution (10% aqueous, 4 mL) was added, and the mixture allowed to stand overnight. The reaction mixture was then concentrated to dryness and the residue chromatographed on silica gel using hexane/ethyl acetate, 1:1, as eluant to afford the product as an orange solid (1.09 g); m.p. 189–190° C.

Calculated for $C_{15}H_{14}N_2O_4$: C, 62.93; H, 4.93; N, 9.79. Found: C, 63.09; H, 4.42; N, 9.57.

Step B: 3-Amino-4-ethoxy-N-phenyl-benzamide

4-Ethoxy-3-nitro-N-phenyl-benzamide (0.77 g, 2.7 mmol) was reduced according to the procedure described for Example 9, Step B to afford the product (0.48 g); m.p. 189–190° C.

Calculated for $C_{15}H_{16}N_2O_2$: C, 70.29; H, 6.29; N, 10.93. Found: C, 70.29; H, 6.11; N, 10.82.

Example 11

3-Amino-4-methoxy-N-(3,5-dimethylphenyl)-benzamide

Prepared according to the procedure described for Example 1 using oxalyl chloride (3.0 mL, 4.39 mmol), 4-methoxy-3-nitrobenzoic acid (5.00 g, 25.36 mmol), dimethylformamide (0.5 mL, 6.5 mmol), and 3,5-dimethylaniline (6.4 mL, 51.33 mmol) to afford the product (4.79 g); m.p. 155–162° C.

Calculated for $C_{16}H_{18}N_2O_2$: C, 71.09; H, 6.71; N, 10.36. Found: C, 70.78; H, 6.90; N, 10.16.

Example 12

3-Amino-4-methoxy-N-(3-chloro-4-methylphenyl)-benzamide

Prepared according to the procedure described for Example 1 using oxalyl chloride (3.0 mL, 4.39 mmol), 4-methoxy-3-nitrobenzoic acid (5.00 g, 25.36 mmol), DMF (1.0 mL, 12.92 mmol), and 3-chloro-4-methylaniline (7.0 mL, 57.69 mmol). Chromatography on silica gel in 95:5 dichloromethane/methanol gave the product, (2.72 g), m.p. 153–157° C.

Calculated for $C_{15}H_{15}N_2O_2Cl$: C, 61.97; H, 5.20; N, 9.63. Found: C, 61.87; H, 5.15; N, 9.72.

Example 13

3-Amino-4-chloro-N-phenyl-benzamide

Prepared according to the procedure described for Example 1 using oxalyl chloride (2.5 mL, 28.66 mmol), 4-chloro-3-nitrobenzoic acid (4.02 g, 19.94 mmol), DMF (1.0 mL, 12.92 mmol), and aniline (3.6 mL, 39.51 mmol) to afford the product (3.39 g) after trituration in hexane; m.p. 194–197° C. after recrystallization from ethyl acetate.

Calculated for $C_{13}H_{11}N_2OCl$: C, 63.29; H, 4.49; N, 11.36. Found: C, 63.44; H, 4.73; N, 11.31.

Example 14

3-Amino-4-methoxy-N-(2,4-difluorophenyl)-benzamide

Prepared according to the procedure described for Example 1 using oxalyl chloride (3.0 mL, 34.39 mmol), 4-methoxy-3-nitrobenzoic acid (5.00 g, 25.36 mmol), DMF (1.0 mL, 12.92 mmol), and 2,4-difluoroaniline (5.2 mL, 51.07 mmol) to afford the product (6.07 g), m.p. 166–168° C. after trituration in hexane.

Calculated for $C_{14}H_{12}N_2O_2F_2$: C, 60.43; H, 4.35; N, 10.07. Found: C, 60.35; H, 4.31; N, 10.01.

Example 15

3-Amino-4-methoxy-N-(3,4-difluorophenyl)-benzamide

Prepared according to the procedure described for Example 1 using oxalyl chloride (3.0 mL, 34.39 mmol), 4-methoxy-3-nitrobenzoic acid (5.00 g, 25.36 mmol), DMF (1.0 mL, 12.92 mmol), and 3,4-difluoroaniline (5.0 mL, 50.42 mmol) to afford the product (6.17 g), m.p. 171–172° C.

Calculated for $C_{14}H_{12}N_2O_2F_2$: C, 60.43; H, 4.35; N, 10.07. Found: C, 60.45; H, 4.36; N, 10.12.

Example 16

3-Amino-4-methoxy-N-(3-chlorophenyl)-benzamide

Prepared according to the procedure described for Example 1 using oxalyl chloride (3.0 mL, 34.39 mmol), 4-methoxy-3-nitrobenzoic acid (5.00 g, 25.36 mmol), DMF (0.5 mL, 6.46 mmol), and 3-chloroaniline (5.4 mL, 51.05 mmol). The reduction was performed as described but using DMF as the solvent to afford the product (2.29 g) after trituration in hexane; m.p. 144–146° C. after recrystallization from ethyl acetate.

Calculated for $C_{14}H_{13}N_2O_2Cl$: C, 60.77; H, 4.74; N, 10.12. Found: C, 60.59; H, 4.61; N, 10.10.

Example 17

3-Amino-4-ethyl-N-phenyl-benzamide
Step A: 3-Nitro-4-ethylbenzoic acid

4-Ethylbenzoic acid (12.0 g, 79.9 mmol) was added portionwise to fuming nitric acid (62 mL) with stirring at room temperature. Following the addition, the mixture was poured into water (500 mL), stirred, and extracted with ethyl acetate (300 mL). Saturated brine (150 mL) was added and the mixture shaken then separated. The organic solution was washed with brine then dried over magnesium sulfate. Filtration, removal of the solvent by rotovap under reduced pressure, and trituration of the residue in hexane afforded the product (13.3 g); pure after recrystallization from hexane/ethyl acetate.

Calculated for $C_9H_9NO_4$: C, 55.39; H, 4.65; N, 7.18. Found: C, 55.34; H, 4.61; N, 7.08.

Step B: 3-Nitro-4-ethyl-N-phenyl-benzamide

Prepared according to the procedure described for Example 1 using oxalyl chloride (2.0 mL, 22.93 mmol), 3-nitro-4-ethylbenzoic acid (4.00 g, 20.51 mmol), DMF (1.0 mL, 12.92 mmol), and aniline (3.8 mL, 41.70 mmol) to afford the product (4.1 g); m.p. 111–113° C. after trituration in hexane.

Calculated for $C_{15}H_{14}N_2O \cdot 0.1\, H_2O$: C, 74.41; H, 6.74; N, 11.57. Found: C, 74.26; H, 6.72; N, 11.40.

Example 18

3-Amino-ethyl-N-(3,4-dichlorophenyl)-benzamide

Prepared according to the procedure described for Example 1 using oxalyl chloride (2.0 mL, 22.93 mmol), 3-nitro-4-ethylbenzoic acid from Example 17, Step A (4.01 g, 20.56 mmol), DMF (1.0 mL, 12.92 mmol), and 3,4-dichloroaniline (6.64 g, 40.98 mmol) to afford the product (2.1 g); m.p. 115–117° C. after chromatography on silica gel using a 10–25% gradient of ethyl acetate in hexane as the eluant.

Calculated for $C_{15}H_{14}Cl_2N_2O$: C, 58.27; H, 4.56; N, 9.06. Found: C, 58.10; H, 4.54; N, 9.02.

Example 19

3-Amino-4-ethyl-N-(3,4-difluorophenyl)-benzamide

Prepared according to the procedure described for Example 1 using oxalyl chloride (2.0 mL, 22.93 mmol), 3-nitro-4-ethylbenzoic acid from Example 17, Step A (3.85 g, 19.74 mmol), DMF (1.0 mL, 12.92 mmol), and 3,4-difluoroaniline (4.0 mL, 40.34 mmol) to afford the product (4.9 g); m.p. 108–110° C. after trituration in hexane.

Calculated for $C_{15}H_{14}N_2OF_2$: C, 65.21; H, 5.11; N, 10.14. Found: C, 64.89; H, 4.92; N, 9.97.

Example 20

3-Amino-4-methylsulfanyl-N-phenyl-benzamide
Step A: 3-Nitro-4-methylsulfanyl-N-phenyl-benzamide 3-Amino-4-chloro-N-phenyl-benzamide from Example 13, Step A (12.06 g, 43.6 mmol) in 100% ethanol was treated with sodium thiomethoxide (3.42 g, 68.5 mmol). The reaction mixture was stirred overnight at room temperature then concentrated to dryness. The residue was shaken with a mixture of ethyl acetate (600 mL) and 1N HCl (200 mL), and the insoluble material was collected by filtration. The resulting solid was washed several times with water then diethyl ether, then dried to afford the product (10.8 g); m.p. 219–222° C.

Calculated for $C_{14}H_{12}N_2O_3S$: C, 58.32; H, 4.20; N, 9.72. Found: C, 58.06; H, 4.13; N, 9.73.

Step B: 3-Amino-4-methylsulfanyl-N-phenyl-benzamide

Prepared according to the procedure described for Example 9, Step B using 4-methylsulfanyl-3-nitro-N-phenyl-benzamide (4.94 g, 17.1 mmol) to give the product (3.72 g); m.p. 143–145° C.

Calculated for $C_{14}H_{14}N_2OS$: C, 65.09; H, 5.46; N, 10.84. Found: C, 65.17; H, 5.41; N, 10.78.

Example 21

N-(3-Amino-4-methoxyphenyl)-benzamide
Step A: N-(3-Nitro-4-fluorophenyl)-benzamide Benzoyl chloride (12 mL, 103 mmol) was added dropwise to 4-fluoro-3-nitroaniline (15.64 g, 100 mmol) and triethylamine (17 mL, 122 mmol) in ethyl acetate (400 mL) at room temperature. The reaction mixture was stirred for 2 hours and then allowed to stand overnight. The reaction mixture was washed with 10% aqueous citric acid solution (200 mL) saturated aqueous sodium bicarbonate solution (200 mL), and brine (100 mL); dried (magnesium sulfate), filtered, and concentrated to about 100 mL at which point a solid began to precipitate. The mixture was cooled to zero degrees and the straw-colored solid collected by filtration to afford the product (21.1 g) in two crops.

Calculated for $C_{13}H_9FN_2O_3$: C, 60.00; H, 3.49; N, 10.76. Found: C, 60.00; H, 3.27; N, 10.84.

Step B: N-(3-Nitro-4-methoxyphenyl)-benzamide

Prepared according to the procedure described for Example 10, Step A from N-(4-fluoro-3-nitrophenyl)-benzamide (5.2 g, 20 mmol) and sodium (1.3 g, 57 mmol) using methanol in place of ethanol to afford the product (3.7 g) after chromatography on silica gel in dichloromethane/methanol 99:1.

Step C: N-(3-Amino-4-methoxyphenyl)-benzamide

Prepared according to the procedure described for Example 9, Step B using N-(4-methoxy-3-nitrophenyl)-benzamide (3.68 g, 13.5 mmol) and zinc dust (20 g) to give the product (2.5 g) after chromatography on silica gel in ethyl acetate/hexane and recrystallization from the same solvent.

Calculated for $C_{14}H_{14}N_2O_2$: C, 69.41; H, 5.82; N, 11.56. Found: C, 69.26; H, 5.59; N, 11.28.

Example 22

3,4-Dichloro-N-(3-amino-4-fluorophenyl)-benzamide

Step A: 3,4-Dichloro-N-(3-nitro-4-fluorophenyl)-benzamide 3,4-Dichlorobenzoyl chloride (4.3 g, 20.5 mmol) was added all at once to 4-fluoro-3-nitroaniline (3.14 g, 20.1 mmol) and triethylamine (3 mL, 21.5 mmol) in ethyl acetate (200 mL) at room temperature. The reaction mixture was stirred overnight at room temperature then diluted to ~500 mL with ethyl acetate. The ethyl acetate was washed successively with 1N HCl (100 mL), saturated sodium bicarbonate (100 mL), and brine (100 mL), then dried (magnesium sulfate), filtered, and stripped of solvent under reduced pressure. Trituration of the residue in hexanes (125 mL) and a few milliliters of ethyl acetate afforded the product by filtration (5.6 g); m.p. 202–204° C.

Step B: 3,4-Dichloro-N-(3-amino-fluorophenyl)-benzamide 3,4-Dichloro-N-(3-nitro-4-fluorophenyl)-benzamide from Step A (1.56 g, 4.7 mmol) was reduced according to the procedure described for Example 9, Step B to give the product (1.15 g); m.p. 151–153° C.

Calculated for $C_{13}H_9Cl_2FN_2O$: C, 52.20; H, 3.03; N, 9.36. Found: C, 52.15; H, 3.55; N, 9.20.

Example 23

3,4-Dichloro-N-(3-amino-4-methoxyphenyl)-benzamide

Step A: 3,4-Dichloro-N-(3-nitro-4-methoxyphenyl)-benzamide

Prepared according to the procedure described for Example 10, Step A from 3,4-dichloro-N-3-nitro-4-fluorophenyl)-benzamide from Example 22, Step A (5.2 g, 20 mmol) and sodium (1.3 g, 57 mmol) using methanol in place of ethanol to afford the product (5.8 g). m.p. 215–218° C. after chromatography on silica gel in dichloromethane/methanol 99:1.

Calculated for $C_{14}H_{10}Cl_2N_2O_4$: C, 49.29; H, 2.95; N, 8.21. Found: C, 49.47; H, 3.23; N, 7.99.

Step B: 3,4-Dichloro-N-(3-amino-4-methoxyphenyl)-benzamide

Prepared according to the procedure described for Example 9, Step B from 3,4-dichloro-N-(3-nitro-4-methoxyphenyl)-benzamide (3.65 g, 10.7 mmol) to afford the product (1.19 g); no distinct m.p. (gradual decomposition).

Calculated for $C_{14}H_{12}Cl_2N_2O_2$: C, 54.04; H, 3.89; N, 9.00. Found: C, 53.81; H, 4.05; N, 8.54.

Example 24

1-(3-Amino-4-methoxyphenyl)-3-phenyl-urea

Step A: 1-(4-Fluoro-3-nitrophenyl)-3-phenyl-urea

Phenylisocyanate (12.0 g, 0.1 mol) was added to 4-fluoro-3-nitroaniline (15.6 g, 0.1 mol) in ethyl acetate (400 mL) at room temperature. The reaction mixture was stirred overnight, then the volume was reduced to approximately 200 mL and the resulting suspension filtered to afford the product (14.3 g); m.p. 200–202° C. Concentration of the filtrate followed by filtration afforded an additional crop of product (5.4 g).

Calculated for $C_{13}H_{10}FN_3O_3$: C, 56.73; H, 3.66; N, 15.27. Found: C, 56.74; H, 3.43; N, 15.46.

Step B: 1-(4-Methoxy-3-nitrophenyl)-3-phenyl-urea

The product from Step A (5.52 g, 20 mmol) was dissolved in methanol (200 mL) and sodium methoxide in methanol (7.4 mL, 25% w/w) was added. After standing overnight at room temperature, the reaction mixture was concentrated to dryness, taken up in ethyl acetate, washed with 10% citric acid solution then brine, and dried (magnesium sulfate), filtered, and concentrated to dryness. The residue was chromatographed two times on silica gel using ethyl acetate as eluant. The fractions enriched in the product were triturated in acetone-ether and the insoluble portion collected by filtration to afford the product (1.64 g), sufficiently pure for use in the next step.

Step C: 1-(3-Amino-4-methoxyphenyl)-3-phenyl-urea

Prepared according to the procedure described for Example 9, Step B using the product from Step B above (1.64 g, 5.7 mmol) to give the product (0.715 g) in three crops; m.p. 174–175° C. after chromatography on silica gel using a 2–4% gradient of methanol in methylene chloride as eluant, followed by recrystallization from ethyl acetate.

Calculated for $C_{14}H_{15}N_3O_2$: C, 65.36; H, 5.88; N, 16.33. Found: C, 65.15; H, 5.55; N, 16.19.

Example 25

3-Phenylamino-N-phenyl-benzamide

A mixture of 3-amino-N-phenyl-benzamide (1.5 g, 7.0 mmol), triphenylbismuth (3.7 g, 8.0 mmol), copper(II) acetate (1.3 g, 7.0 mmol), and triethylamine (0.73 g, 7.0 mmol) was stirred under an inert atmosphere in dichloromethane (100 mL) and heated to reflux. After 4 to 24 hours (the reaction was monitored for completeness using tlc), the mixture was allowed to cool and was then diluted with additional dichloromethane (200 mL) and stirred into 2N hydrochloric acid (250 mL). After 2 hours, the layers were separated and the organic phase washed successively with 2N HCl, water, 0.5 M aqueous potassium carbonate, water, and saturated aqueous sodium chloride, then dried over $MgSO_4$. The solution was filtered then stripped of solvent under reduced pressure to afford a solid residue which was purified by chromatography on a column of silica gel in chloroform to give the product (1.0 g); m.p. 134–135° C. after recrystallization from toluene.

Calculated for $C_{19}H_{16}N_2O$: C, 79.14; H, 5.59; N, 9.71. Found: C, 79.17; H, 5.42; N, 9.63.

Example 26

3-(3,5-Dichloro-phenylamino)-N-phenyl-benzamide

A mixture of 3-amino-N-phenyl-benzamide (2.0 g, 9.4 mmol), 3,5-dichloroiodobenzene (2.65 g, 9.7 mmol), N-ethylmorpholine (1.1 g, 9.5 mmol), and copper(II) acetate (0.1 g, 0.6 mmol) in N,N-dimethylformamide (6 mL) was stirred under an inert atmosphere and heated to reflux. After 120 hours, the mixture was allowed to cool and was stirred into water (300 mL) and acidified with concentrated hydrochloric acid. The mixture was extracted with dichloromethane (300 mL) and the extract separated and washed successively with 2N hydrochloric acid, water, 0.5 M aqueous potassium carbonate, water, and saturated aqueous sodium chloride, then dried over $MgSO_4$. The solution was filtered and stripped of solvent under reduced pressure to leave a solid residue which was subjected to chromatography on a column of silica gel in chloroform to afford the product (0.1 g); m.p. 164–165° C. after recrystallization from ethyl alcohol.

Calculated for $C_{19}H_{14}Cl_2N_2O$: C, 63.88; H, 3.95; N, 7.84. Found: C, 63.64; H, 4.04; N, 7.61.

Example 27

3-(2-Methoxy-phenylamino)-N-phenyl-benzamide

Prepared according to the procedure of Example 25 using 3-amino-N-phenyl-benzamide (0.85 g, 4.0 mmol), tris(2- methoxyphenyl)bismuthine (2.2 g, 4.1 mmol), copper(II) acetate (0.75 g, 4.1 mmol), and triethylamine (0.42 g, 4.1 mmol) to give a solid residue which was subjected to chromatography on a column of silica gel in chloroform to afford the product (0.9 g); m.p. 153–154° C. after recrystallization from ethanol.

Calculated for $C_{20}H_{18}N_2O_2$: C, 75.45; H, 5.70; N, 8.80. Found: C, 75.21; H, 5.65; N, 8.72.

Example 28

4-Methoxy-3-phenylamino-N-phenyl-benzamide

Prepared according to the procedure of Example 25 using 3-amino-4-methoxy-N-phenyl-benzamide (1.5 g, 6.2 mmol), triphenylbismuth (2.9 g, 6.6 mmol), copper(II) acetate (1.13 g, 6.2 mmol), and triethylamine (0.62 g, 6.2 mmol) to give a solid which was recrystallized from ethanol then subjected to chromatography on a column of silica gel in dichloromethane to afford the product (0.8 g); m.p. 194–195° C. after an additional recrystallization from ethyl alcohol.

Calculated for $C_{20}H_{18}N_2O_2$: C, 75.45; H, 5.70; N, 8.80. Found: C, 74.66; H, 5.43; N, 8.67.

Example 29

3-(2-Methoxy-phenylamino)-4-methoxy-N-phenyl-benzamide

Prepared according to the procedure of Example 25 using 3-amino-4-methoxy-N-phenyl-benzamide (0.8 g, 3.2 mmol), tris(2-methoxyphenyl)bismuthine (1.8 g, 3.4 mmol), copper(II) acetate (0.6 g, 3.4 mmol), and triethylamine (0.34 g, 3.4 mmol) to afford the product (0.9 g); m.p. 155–156° C. after chromatography on a column of silica gel in chloroform followed by recrystallization from ethanol.

Calculated for $C_{21}H_{20}N_2O_3$: C, 72.40; H, 5.79; N, 8.04. Found: C, 72.13; H, 5.73; N, 7.94.

Example 30

3-(3-Trifluoromethyl-phenylamino)-4-methoxy-N-phenyl-benzamide

Prepared according to the procedure of Example 25 using 3-amino-4-methoxy-N-phenyl-benzamide (0.7 g, 2.9 mmol), tris(3-trifluoromethylphenyl)bismuthine (2.0 g, 3.1 mmol), copper(II) acetate (0.54 g, 3.0 mmol), and triethylamine (0.29 g, 2.9 mmol) to afford the product (0.7 g); m.p. 183–184° C. after recrystallization from acetonitrile.

Calculated for $C_{21}H_{17}FN_2O_2$: C, 65.28; H, 4.43; N, 7.25. Found: C, 64.89; H, 4.13; N, 7.24.

Example 31

3-(3-Chloro-phenylamino)-4-methoxy-N-phenyl-benzamide

Prepared according to the procedure of Example 25 using 3-amino-4-methoxy-N-phenyl-benzamide (1.5 g, 6.2 mmol), tris(3-chlorophenyl)bismuthine (3.5 g, 6.4 mmol), copper(II) acetate (1.16 g, 6.4 mmol), and triethylamine (0.65 g, 6.4 mmol) to give a solid which was purified by chromatography on a column of silica gel in chloroform/ ethyl acetate 99:1 to afford the product (1.8 g); m.p. 168–170° C. after recrystallization from ethanol.

Calculated for $C_{20}H_{17}ClN_2O_2$: C, 68.09; H, 4.86; N, 7.94. Found: C, 67.91; H, 4.71; N, 7.80.

Example 32

3-(3-Methyl-phenylamino)-4-methoxy-N-phenyl-benzamide

Prepared according to the procedure described for Example 25 using 3-amino-4-methoxy-N-phenyl-benzamide (1.0 g, 4.1 mmol), tris(3-methylphenyl)bismuthine (2.2 g, 4.6 mmol), copper(II) acetate (0.8 g, 4.4 mmol), and triethylamine (0.44 g, 4.4 mmol) to afford the product (0.7 g); m.p. 160–161° C. after recrystallization from acetonitrile.

Calculated for $C_{21}H_{20}N_2O_2$: C, 75.88; H, 6.06; N, 8.43. Found: C, 75.63; H, 6.11; N, 8.47.

Example 33

3-(3-Nitro-phenylamino)-4-methoxy-N-phenyl-benzamide

A mixture of 3-amino-4-methoxy-N-phenyl-benzamide (2.0 g, 8 mmol), 1-iodo-3-nitrobenzene (2.5 g, 10 mmol), potassium carbonate (2.8 g, 20 mmol), and copper(I) iodide (0.4 g, 2 mmol) in mesitylene (20 mL) was stirred under an inert atmosphere and heated to reflux. After 48 hours, the mixture was allowed to cool and was then diluted with tetrahydrofuran (100 mL) and filtered through Celite. The filtrate was stripped of solvent under reduced pressure to leave an oily residue which was dissolved in ethyl acetate (250 mL) and extracted successively with 2N hydrochloric acid (2×200 mL), water, 0.5 M aqueous potassium carbonate, water, and saturated aqueous sodium chloride, then dried over $MgSO_4$. The solution was filtered and the filtrate stripped of solvent under reduced pressure. The resulting residue was subjected to chromatography on a column of silica gel in chloroform to afford the product (0.18 g); m.p. 220–221° C. after recrystallization from acetonitrile.

Calculated for $C_{20}H_{17}N_3O_4$: C, 66.11; H, 4.72; N, 11.56. Found: C, 65.81; H, 4.63; N, 11.47.

Example 34

3-(4-Methyl-phenylamino)-4-methoxy-N-phenyl-benzamide

Prepared according to the procedure of Example 25 using 3-amino-4-methoxy-N-phenyl-benzamide (1.1 g, 4.5 mmol), tris(4-methylphenyl)bismuthine (2.5 g, 5.2 mmol), copper(II) acetate (0.82 g, 4.5 mmol), and triethylamine (0.46 g, 4.5 mmol) to afford the product (0.8 g); m.p. 187–188° C. after recrystallization from acetonitrile then ethyl acetate.

Calculated for $C_{21}H_{20}N_2O_2$: C, 75.88; H, 6.06; N, 8.43. Found: C, 75.57; H, 5.83; N, 8.34.

Example 35

3-(3,5-Dichloro-phenylamino)-4-methoxy-N-phenyl-benzamide

Prepared according to the procedure of Example 33 using 3-amino-4-methoxy-N-phenyl-benzamide (2.0 g, 8.3 mmol), 3,5-dichloroiodobenzene (4.5 g, 16.5 mmol), potassium carbonate (2.9 g, 21.0 mmol), and copper(I) iodide (0.5 g, 2.6 mmol) to give a gummy residue which was subjected to chromatography on a column of silica gel in dichloromethane to afford the product (0.3 g); m.p. 207–208° C. after recrystallization from ethanol.

Calculated for $C_{20}H_{16}Cl_2N_2O_2 \cdot 0.2C_2H_6O$: C, 61.80; H, 4.37; N, 7.07. Found: C, 61.47; H, 4.04; N, 7.08.

Example 36

3-(3,5-Dimethyl-phenylamino)-4-methoxy-N-phenyl-benzamide

Prepared according to the procedure of Example 25 using 3-amino-4-methoxy-N-phenyl-benzamide (1.5 g, 6.3 mmol), tris(3,5-dimethylphenyl)-bismuthine (3.3 g, 6.3 mmol), copper(II) acetate (1.15 g, 6.3 mmol), and triethylamine (0.64 g, 6.3 mmol) to afford the product (1.1 g); m.p. 198–199° C. after recrystallization from a mixture of dichloromethane and ethyl acetate 10:1.

Calculated for $C_{22}H_{22}N_2O_2 \cdot 0.5CH_2Cl_2$: C, 75.52; H, 6.35; N, 7.99. Found: C, 75.56; H, 6.32; N, 7.92.

Example 37

3-Phenylamino-4-fluoro-N-phenyl-benzamide

Prepared according to the procedure of Example 25 using 3-amino-4-fluoro-N-phenyl-benzamide from Example 9 (0.93 g, 4.0 mmol), triphenylbismuth (1.9 g, 4.3 mmol), copper(II) acetate (0.8 g, 4.4 mmol), and triethylamine (0.45 g, 6.3 mmol) to afford the product (0.4 g); m.p. 132–133° C., after chromatography on a column of silica gel in dichloromethane/ethyl acetate 95:5.

Calculated for $C_{19}H_{15}FN_2O$: C, 74.50; H, 4.94; N, 9.14. Found: C, 74.21; H, 4.96; N, 9.00.

Example 38

3-Phenylamino-4-methyl-N-phenyl-benzamide

Prepared according to the procedure of Example 25 using 3-amino-4-methyl-benzanilide from Example 1 (1.0 g, 4.4 mmol), triphenylbismuth (2.0 g, 4.5 mmol), copper(II) acetate (0.82 g, 4.5 mmol), and triethylamine (0.46 g, 4.5 mmol) to afford the product (0.8); m.p. 119–120° C. after chromatography on a column of silica gel in dichloromethane/ethyl acetate 99:1 and subsequent crystallization from ethanol.

Calculated for $C_{20}H_{18}N_2O \cdot 0.1C_2H_6O$: C, 79.36; H, 6.01; N, 8.98. Found: C, 79.02; H, 6.00; N, 9.26.

Example 39

3-Phenylamino-4-methoxy-N-(4-fluorophenyl)-benzamide

Prepared according to the procedure of Example 25 using 3-amino-4-methyl-N-(4-fluorophenyl)-benzamide from Example 8 (1.0 g, 3.8 mmol), triphenylbismuth (1.8 g, 4.1 mmol), copper(II) acetate (0.8 g, 4.4 mmol), and triethylamine (0.44 g, 4.4 mmol) to afford the product (0.8 g); m.p. 151–152° C. after recrystallization from ethanol.

Calculated for $C_{20}H_{17}FN_2O_2 \cdot 0.1C_2H_6O$: C, 71.16; H, 5.20; N, 8.22. Found: C, 70.84; H, 5.06; N, 8.09.

Example 40

3-(3-Trifluoromethyl-phenylamino)-4-methoxy-N-(4-fluorophenyl)-benzamide

Prepared according to the procedure of Example 25 using 3-amino-4-methoxy-N-(4-fluorophenyl)-benzamide from Example 8 (1.0 g, 3.8 mmol), tris(3-trifluoromethylphenyl) bismuthine (2.8 g, 4.3 mmol), copper(II) acetate (0.8 g, 4.4 mmol), and triethylamine (0.44 g, 4.4 mmol) to afford the product (0.9 g); m.p. 163–164° C. after recrystallization from acetonitrile.

Calculated for $C_{21}H_{16}F_4N_2O_2$: C, 62.38; H, 3.99; N, 6.93. Found: C, 62.18; H, 4.00; N, 6.84.

Example 41

4-Ethyl-3-(3-trifluoromethyl-phenylamino)-N-phenyl-benzamide

Prepared according to the procedure of Example 25 using 3-amino-4-ethyl-N-phenyl-benzamide from Example 17 (1.0 g, 4.2 mmol), tris(3-trifluoromethylphenyl)bismuthine (2.9 g, 4.5 mmol), copper(II) acetate (0.8 g, 4.4 mmol), and triethylamine (0.45 g, 4.5 mmol) to give a syrup which was crystallized from ether to afford the product (0.42 g); m.p. 133–134° C. after recrystallization from acetonitrile.

Calculated for $C_{22}H_{19}F_3N_2O$: C, 68.74; H, 4.98; N, 7.29. Found: C, 68.71; H, 4.79; N, 7.30.

Example 42

4-Ethoxy-3-(trifluoromethyl-phenylamino)-N-phenyl-benzamide

Prepared according to the procedure of Example 25 using 3-amino-4-ethoxy-N-phenyl-benzamide from Example 10 (0.6 g, 2.3 mmol), tris(3-trifluoromethylphenyl)bismuthine (1.6 g, 2.5 mmol), copper(II) acetate (0.45 g, 2.5 mmol), and triethylamine (0.25 g, 2.5 mmol) to afford the product (0.53 g); m.p. 184–185° C. after recrystallization from ethyl alcohol.

Calculated for $C_{22}H_{19}F_3N_2O_2$: C, 65.99; H, 4.78; N, 7.00. Found: C, 65.82; H, 4.73; N, 6.92.

Example 43

4-Methylsulfanyl-3-(3-trifluoromethyl-phenylamino)-N-phenyl-benzamide

Prepared according to the procedure of Example 25 using 3-amino-4-methylsufanyl-N-phenyl-benzamide from Example 20 (0.5 g, 1.9 mmol), tris(3-trifluoromethylphenyl) bismuthine (1.4 g, 2.1 mmol), copper(II) acetate (0.4 g, 2.2 mmol), and triethylamine (0.21 g, 2.1 mmol) to afford the product (0.25 g); m.p. 169–170° C. after recrystallization from acetonitrile.

Calculated for $C_{21}H_{17}F_3N_2OS$: C, 62.68; H, 4.26; N, 6.96. Found: C, 62.34; H, 4.11; N, 6.87.

Example 44

3-[4-(4,4-Dimethyl-4,5-dihydro-oxazol-2-yl)-phenylamino]-4-methoxy-N-phenyl-benzamide Prepared according to the procedure of Example 25 using 3-amino-4-methoxy-N-phenyl-benzamide (1.6 g, 6.6 mmol), tris[4-(4,4-dimethyl-2-oxazolinyl)-phenyl] bismuthine (4.8 g, 6.6 mmol), copper(II) acetate (1.2 g, 6.6 mmol), and triethylamine (0.67 g, 6.6 mmol) to afford the product (0.8 g); m.p. 221–222° C. after recrystallization from acetonitrile.

Calculated for $C_{25}H_{25}N_3O_3$: C, 72.27; H, 6.06; N, 10.11. Found: C, 71.04; H, 5.92; N, 9.91.

Example 45

4-Methoxy-3-(3-trifluoromethyl-phenylamino)-N-(3-pyridyl)-benzamide

Prepared according to the procedure of Example 25 using 3-amino-4-methoxy-N-(3-pyridyl)-benzamide from Example 5 (1.0 g, 4.1 mmol), tris(3-trifluoromethylphenyl) bismuthine (2.8 g, 4.3 mmol), copper(II) acetate (0.8 g, 4.4 mmol), and triethylamine (0.44 g, 4.3 mmol) to afford the product (0.6 g); m.p. 184–185° C. after recrystallization from acetonitrile.

Calculated for $C_{20}H_{16}F_3N_3O_2$: C, 62.01; H, 4.16; N, 10.85. Found: C, 61.93; H, 4.14; N, 10.85.

Example 46

4-Methoxy-3-(3,5-dimethyl-phenylamino)-N-(4-fluorophenyl)-benzamide

Prepared according to the procedure of Example 25 using 3-amino-4-methoxy-N-(4-fluorophenyl)-benzamide from Example 8 (1.0 g, 3.8 mmol), tris(3,5-dimethylphenyl) bismuthine (2.1 g, 4.0 mmol), copper(II) acetate (0.8 g, 4.4 mmol), and triethylamine (0.45 g, 4.4 mmol) to afford the product (0.6 g); m.p. 199–200° C. after recrystallization from acetonitrile.

Calculated for $C_{22}H_{21}FN_2O_2$: C, 72.51; H, 5.81; N, 7.69. Found: C, 72.32; H, 5.76; N, 7.60.

Example 47

4-Methoxy-3-(3-trifluoromethyl-phenylamino)-N-(3,4-dichlorophenyl)benzamide

Prepared according to the procedure of Example 25 using 3-amino-4-methoxy-N-(3,4-dichlorophenyl)-benzamide from Example 4 (0.9 g, 2.9 mmol), tris(3-trifluoromethylphenyl)bismuthine (2.1 g, 3.3 mmol), copper (II) acetate (0.6 g, 3.3 mmol), and triethylamine (0.34 g 3.3 mmol) to afford the product (0.4 g); m.p. 154–155° C. after recrystallization from ethanol.

Calculated for $C_{21}H_{15}Cl_2F_3N_2O_2$: C, 55.40; H, 3.32; N, 6.15. Found: C, 55.21; H, 3.20; N, 5.88.

Example 48

4-Methoxy-3-(3-trifluoromethyl-phenylamino)-N-(3,4-difluorophenyl)-benzamide

Prepared according to the procedure of Example 25 using 3-amino-4-methoxy-N-(3,4-difluorophenyl)-benzamide from Example 15 (1.1 g, 4.0 mmol), tris(3-trifluoromethylphenyl)bismuthine (2.8 g, 4.3 mmol), copper (II) acetate (0.8 g, 4.3 mmol), and triethylamine (0.44 g, 4.3 mmol) to afford the product (1.2 g); m.p. 166–169° C. after recrystallization from ethanol.

Calculated for $C_{21}H_{15}F_5N_2O_2$: C, 59.72; H, 3.58; N, 6.63. Found: C, 59.58; H, 3.44; N, 6.44.

Example 49

N-[3-(Phenylamino)-4-methoxy-phenyl]-benzamide

Prepared according to the procedure of Example 25 using N-(3-amino-4-methoxyphenyl)-benzamide from Example 21 (1.0 g, 4.1 mmol), triphenylbismuth (2.0 g, 4.5 mmol), copper(II) acetate (0.82 g, 4.5 mmol), and triethylamine (0.46 g, 4.6 mmol) to afford the product (0.6 g); m.p. 209–210° C. after recrystallization from ethanol.

Calculated for $C_{20}H_{18}N_2O_2$: C, 75.45; H, 5.70; N, 8.80. Found: C, 75.26; H, 5.75; N, 8.42.

Example 50

3-Benzylamino-4-methoxy-N-phenyl-benzamide

Benzaldehyde (2.2 g, 21.0 mmol) was added to a stirred solution of 3-amino-4-methoxy-N-phenyl-benzamide (5.0 g, 21.0 mmol) in dichloromethane (250 mL) under an inert atmosphere at room temperature, followed by acetic acid (1.26 g, 21.0 mmol). After 1 hour sodium triacetoxyborohydride (4.7 g, 21.0 mmol) was added in one portion. After 18 hours, saturated aqueous sodium bicarbonate (200 mL) was added and the mixture stirred for 2 to 3 hours. The layers were separated, the organic phase was washed with water then saturated aqueous sodium chloride, then dried over $MgSO_4$. The solution was filtered and stripped of solvent under reduced pressure to afford the product (6.5 g); m.p. 164–165° C. after recrystallization from ethanol.

Calculated for $C_{21}H_{20}N_2O_2$: C, 75.88; H, 6.06; N, 8.43. Found: C, 75.62; H, 6.02; N, 8.44.

Example 51

3-(3,5-Dichloro-benzylamino)-4-methoxy-N-phenyl-benzamide

Prepared according to the procedure of Example 50 using 3,5-dichloro-benzaldehyde (0.88 g, 5.0 mmol), 3-amino-4-methoxy-N-phenyl-benzamide (1.22 g, 5.0 mmol), acetic acid (0.24 g, 5.3 mmol), and sodium triacetoxyborohydride (1.12 mmol) to afford the product (0.65 g); m.p. 164–165° C. after recrystallization from ethanol.

Calculated for $C_{21}H_{18}Cl_2N_2O_2$: C, 62.86; H, 4.52; N, 6.98. Found: C, 62.58; H, 4.41; N, 6.83.

Example 52

3-(3,4-Dimethoxy-benzylamino)-4-methoxy-N-phenyl-benzamide

Prepared according to the procedure of Example 50 using 3,4-dimethoxybenzaldehyde (1.94 g, 11.6 mmol), 3-amino-4-methoxy-N-phenyl-benzamide (2.8 g, 11.6 mmol), acetic acid (0.69 g, 11.5 mmol), and sodium triacetoxyborohydride (2.6 g, 11.7 mmol) to afford the product (2.9 g); m.p. 187–188° C. after recrystallization from ethanol.

Calculated for $C_{23}H_{24}N_2O_4$: C, 70.39; H, 6.16; N, 7.14. Found: C, 70.31; H, 6.00; N, 7.10.

Example 53

3-Phenoxy-N-phenyl-benzamide

Prepared according to the procedure of Example 1 Step A using 3-phenoxybenzoic acid (1.2 g, 5.5 mmol), oxalyl chloride (0.55 mL, 6.3 mmol), and aniline (1.0 g, 10.7 mmol) to afford the product (1.5 g); m.p. 111–112° C. after recrystallization from ethanol.

Calculated for $C_{19}H_{15}NO_2$: C, 78.87; H, 5.23; N, 4.84. Found: C, 78.69; H, 5.25; N, 4.82.

Example 54

3-Phenoxy-4-methoxy-N-phenyl-benzamide

Step A: 3-Hydroxy-4-methoxybenzoic Acid Methyl Ester

A stirred suspension of 3-hydroxy-4-methoxybenzoic acid (6.3 g, 38 mmol) in methanol (200 mL) at ambient temperature was saturated with HCl gas until a solution was obtained. After 16 hours, the mixture was stripped of solvent under reduced pressure to afford the crystalline product (7.1 g); m.p. 64–65° C. after chromatography on silica gel eluting with 2.5% methanol in dichloromethane.

Calculated for $C_9H_{10}O_4$: C, 59.34; H, 5.53. Found: C, 59.41; H, 5.39.

Step B: 3-Phenoxy-4-methoxybenzoic Acid Methyl Ester

Prepared according to the procedure of Example 25 using 3-hydroxy-4-methoxybenzoic acid methyl ester (1.2 g, 6.6 mmol), triphenylbismuth (3.2 g, 7.3 mmol), copper(II) acetate (1.32 g, 7.3 mmol), and triethylamine (0.73 g, 7.2 mmol) to afford the product (0.9 g); m.p. 61–63° C. after trituration in methanol.

Step C: 3-Phenoxy-4-methoxybenzoic Acid

3-Phenoxy-4-methoxybenzoic acid methyl ester (0.8 g, 3.1 mmol) was stirred in a mixture of methanol (8 mL) and 4N potassium hydroxide (10 mL) and heated to reflux. After 2 hours, the mixture was stirred into water (60 mL) and extracted with ether (25 mL). The aqueous solution was stirred and acidified with 4N HCl, and the resulting precipitate was filtered off, rinsed with water, and dried to afford the product (0.7 g); m.p. 186–187° C.

Calculated for $C_{14}H_{12}O_4$: C, 68.85; H, 4.95. Found: C, 68.65; H, 4.74.

Step D: 3-Phenoxy-4-methoxy-N-phenyl-benzamide

Prepared according to the procedure of Example 1 using 3-phenoxy-4-methoxybenzoic acid (0.3 g, 1.2 mmol), oxalyl chloride (0.19 g, 1.5 mmol), and aniline (0.22 g, 2.4 mmol) to afford the product (0.3 g); m.p. 200–201° C. after recrystallization from ethanol.

Calculated for $C_{20}H_{17}NO_3$: C, 75.22; H, 5.37; N, 4.39. Found: C, 75.01 H, 5.36; N, 4.17.

Example 55

3-(Phenylamino)-4-methoxybenzoic acid, phenyl ester

Step A: 3-(Phenylamino)-4-methoxybenzoic acid, methyl ester

Prepared according to the procedure of Example 25 using 3-methoxy-4-aminobenzoic acid methyl ester (1.5 g, 6.9 mmol), triphenylbismuth (3.1 g, 7.0 mmol), copper(II) acetate (1.3 g, 7.2 mmol), and triethylamine (0.73 g, 7.2 mmol) to afford the product (1.5 g); m.p. 79–81° C., after recrystallization from ethanol.

Step B: 3-(Phenylamino)-4-methoxybenzoic acid

A mixture of 3-(phenylamino)-4-methoxybenzoic acid, methyl ester (0.4 g, 1.6 mmol), methanol (10 mL), and 4N sodium hydroxide (15 mL) was stirred and heated to reflux. After 2 hours, the methanol was removed by rotary evaporator and the residual aqueous suspension stirred and acidified with 4N HCl. The precipitate was filtered off, rinsed with water, and dried to afford the product (0.35 g); m.p. 198–200° C.

Calculated for $C_{14}H_{13}NO_3$: C, 69.12; H, 5.39; N, 5.76. Found: C, 68.27; H, 5.53; N, 5.65.

Step C: 3-(Phenylamino)-4-methoxybenzoic acid, phenyl ester

N,N'-Carbonyldiimidazole (0.41 g, 2.5 mmol) was added to a stirred solution of 3-(phenylamino)-4-methoxybenzoic acid (0.6 g, 2.5 mmol) in dimethylformamide (15 mL) under an inert atmosphere. After 30 minutes, the solution was heated to 50° C. for 1 hour, then phenol (0.24 g, 2.6 mmol) was added followed by diazabicycloundecene (0.40 g, 2.6 mmol) and heating at 50° C. was continued for 20 more hours. The mixture was allowed to cool and was then diluted with diethyl ether (100 mL) and washed successively with 2N HCl, water, 0.5N $K_2CO_3$, and saturated brine then dried over $MgSO_4$. The solvent was removed under reduced pressure, and the residue was chromatographed on a column of silica gel in ethyl acetate to afford the product (0.27 g); m.p. 130–131° C. after recrystallization from acetonitrile.

Calculated for $C_{20}H_{17}NO_3$: C, 75.22; H, 5.37; N, 4.39. Found: C, 74.92; H, 5.51; N, 4.45.

Example 56

4-Hydroxy-3-(3,5-dichloro-phenylamino)-N-phenyl-benzamide

Step A: 3-Amino-4-methoxybenzoic acid methyl ester

Concentrated $H_2SO_4$ (9 mL) was added in portions to a stirred solution of 3-amino-4-methoxybenzoic acid (20.06 g, 110.4 mmol) in methanol (280 mL). The mixture was heated to reflux overnight then cooled to room temperature, and the solvent was removed in vacuo. The residue was shaken with 10% aqueous potassium carbonate then extracted with ethyl acetate three times. The combined extracts were washed with saturated sodium bicarbonate, dried ($MgSO_4$), filtered, and stripped of solvent under reduced pressure. The residual solid was triturated with hexane and filtered to yield the product (10.82 g); m.p. 75–77° C.

Calculated for $C_9H_{11}NO_3$: C, 59.66; H, 6.12; N, 7.73. Found: C, 59.93; H, 6.22; N, 7.54.

Step B: 2-Acetylamino-4-methoxybenzoic acid methyl ester

Acetic anhydride (6.5 mL, 68.80 mmol) was added to a solution of 3-amino-4-methoxybenzoic acid methyl ester (10.58 g, 58.39 mmol) in 200 mL of ethyl acetate. The reaction was stirred at room temperature. After 3 days, the mixture was filtered and the filtrate was washed with saturated aqueous sodium bicarbonate until pH=5, dried ($MgSO_4$), and stripped of solvent under reduced pressure. The residue was triturated with hexane and filtered to afford a tan solid which was combined with the residue remaining in the funnel after the initial filtration and dried to afford the desired product (9.6 g); m.p. 123–126° C.

Calculated for $C_{11}H_{13}NO_4$: C, 59.19; H, 5.87; N, 6.27. Found: C, 59.03; H, 5.81; N, 6.23.

Step C: 3-[Acetyl-(3,5-dichlorophenyl)-amino]-4-methoxybenzoic acid methyl ester A mixture of 2-acetylamino-4-methoxybenzoic acid methyl ester (9.58 g, 42.92 mmol), 1-bromo-3,5-dichlorobenzene (28.80 g, 127.48 mmol), copper iodide (2.32 g, 12.18 mmol), and sodium bicarbonate (8.72 g, 103.80 mmol) in of mesitylene (60 mL) was heated to reflux. After 7 days, the mixture was allowed to cool and was diluted with ethyl acetate (300 mL). The resulting solid was removed by filtration and washed with ethyl acetate. The filtrate was concentrated in vacuo and the residue was chromatographed on silica gel eluting with hexane/ethyl acetate (9:1→1:1) to afford the product (11.6 g); m.p. 100–101° C. after trituration in hexane.

Calculated for $C_{17}H_{15}Cl_2NO_4$: C, 55.45; H, 4.11; N, 3.80. Found: C, 55.12; H, 3.97; N, 3.73.

Step D: 3-(3,5-Dichlorophenylamino)-4-methoxybenzoic acid methyl ester

Concentrated HCl (45 mL) was added to a solution of 3-[acetyl-(3,5-dichlorophenyl)-amino]-4-methoxybenzoic acid methyl ester (11.46 g, 31.12 mmol) in a mixture of tetrahydrofuran (75 mL) and methanol (75 mL). The reaction was heated to reflux. After 3 days, the solvent was removed in vacuo and the residue was dissolved in ethyl acetate and dried ($MgSO_4$). The ethyl acetate was removed under reduced pressure to give the product (2.4 g); m.p. 134–135° C. after chromatography on silica gel in ethyl acetate followed by recrystallization from ether/hexane 1:9.

Calculated for $C_{15}H_{13}Cl_2NO_3$: C, 55.24; H, 4.02; N, 4.29. Found: C, 55.20; H, 4.08; N, 4.07.

Step E: 3-(3,5-Dichlorophenylamino)-4-hydroxybenzoic acid

A solution of 3-(3,5-dichlorophenylamino)-4-methoxybenzoic acid methyl ester (4.48 g, 13.74 mmol), 100 mL of concentrated HBr, and 60 mL of acetic acid was heated to reflux. After 6 days, the reaction was cooled to room temperature and concentrated aqueous ammonium hydroxide was added in portions until the pH=4. The mixture was extracted with ethyl acetate three times, and the combined extracts were washed with brine (2×) and $H_2O$ (2×) then dried over $MgSO_4$ and stripped of solvent in vacuo. The residue was triturated with 5% ether/hexane, filtered off and dried to afford the product (3.7 g); m.p. 166–167° C.

Calculated for $C_{13}H_9Cl_2NO_3 \cdot H_2O$: C, 49.39; H, 3.51; N, 4.32. Found: C, 49.16; H, 3.34; N, 4.23.

Step F: 3-(3,5-Dichloro-phenylamino)-4-hydroxy-N-phenyl-benzamide

Dicyclohexylcarbodiimide (2.68 g, 12.99 mmol) was added to a solution of 3-(3,5-dichlorophenylamino)-4-hydroxybenzoic acid (3.59 g, 12.05 mmol) and aniline (1.19 mL, 13.06 mmol) in tetrahydrofuran (45 mL) at ice bath temperature. After 5 days at ambient temperature, the white precipitate was collected by filtration and washed with ethyl acetate. The filtrate was taken to dryness in vacuo, redissolved in ethyl acetate, and washed successively with $H_2O$, 1N HCl, and brine. The organic layer was dried ($MgSO_4$), filtered, and the solvent removed under reduced pressure. The crude material was chromatographed on silica gel, eluting with 4:1 hexane/ethyl acetate. The effluent was extracted with 1N NaOH, dried ($MgSO_4$), filtered, and stripped of solvent under reduced pressure. The resulting foam was triturated with hexane to afford the product (1.15 g); m.p. 160–162° C.

Calculated for $C_{19}H_{14}N_2O_2Cl_2 \cdot 0.25\ H_2O$: C, 60.41; H, 3.87; N, 7.42. Found: C, 60.34; H, 3.63; N, 7.20.

Example 57

3-(3,5-Dichloro-phenylamino)-4-hydroxy-N-(4-methoxyphenyl)-benzamide

Prepared according to the procedure described for Example 56, Step F using 3-(3,5-dichloro-phenylamino)-4-hydroxybenzoic acid from Example 56, Step E (0.652 g, 2.19 mmol), 4-anisidine (0.276 g, 2.24 mmol), and 1,3-dicyclohexylcarbodiimide (0.538 g, 2.61 mmol) to afford the product (0.19 g); m.p. 186–187° C. after chromatography on silica gel using a 20–25% gradient of ethyl acetate in hexane.

Calculated for $C_{20}H_{16}Cl_2N_2O_3 \cdot 0.5\ H_2O$: C, 58.26; H, 4.16; N, 6.80. Found: C, 58.17; H 4.13; N, 6.61.

Example 58

3-(3,5-Dichloro-phenylamino)-4-hydroxy-N-(4-methylphenyl)-benzamide

Prepared according to the procedure described for Example 56, Step F using 3-(3,5-dichloro-phenylamino)-4-hydroxybenzoic acid from Example 56, Step E (0.365 g, 1.22 mmol), p-toluidine (0.134 g, 1.25 mmol), and 1,3-dicyclohexylcarbodiimide (1.48 mmol) to afford the product (0.34 g); m.p. 179–183° C. after chromatography on silica gel using ethyl acetate/hexane 1:1 followed by trituration in hexane.

Calculated for $C_{20}H_{16}Cl_2N_2O_2 \cdot 0.25\ H_2O$: C, 61.31; H, 4.25; N, 7.15. Found: C, 61.34; H, 4.48; N, 7.18.

Example 59

3-(3,5-Dichloro-phenylamino)-4-hydroxy-N-(3-hydroxy-4-methoxyphenyl)-benzamide

Prepared according to the procedure described for Example 56, Step F, with the exception that a catalytic amount of 4-dimethylaminopyridine was added to the reaction mixture following the DCC. Thus, 3-(3,5-dichloro-phenylamino-4-hydroxybenzoic acid from Example 56, Step E (0.501 g, 1.68 mmol), 3-hydroxy-4-methoxyaniline (0.234 g, 1.68 mmol), and 1,3-dicyclohexylcarbodiimide (0.416 g, 2.02 mmol) gave the product (0.06 g); m.p. 170–171° C. after chromatography on silica gel using ethyl acetate/hexane 1:1.

Calculated for $C_{20}H_{16}Cl_2N_2O_4 \cdot 0.4\ H_2O$: C, 56.32; H, 3.97; N, 6.57. Found: C, 56.55; H, 4.32; N, 5.98.

Example 60

3-[3-(3,5-Dichlorophenyl)-thioureido]-4-methoxy-N-phenyl-benzamide

A mixture of 3-amino-4-methoxy-N-phenyl-benzamide (0.277 g, 1.14 mmol) and 3,5-dichlorophenyl isothiocyanate (0.238 g, 1.17 mmol) in ethyl acetate (30 mL) was warmed until a solution was obtained, then allowed to stand at room temperature for 3 days. The reaction was concentrated until a crystalline precipitate was obtained then allowed to stand overnight at room temperature. The solid was collected by filtration, rinsed with ethyl acetate/hexane, and dried to afford the product (0.423 g); m.p. 195–197° C.

Calculated for $C_{21}H_{17}Cl_2N_3O_2S$: C, 56.51; H, 3.84; N, 9.41. Found: C, 56.20; H, 3.69; N, 9.28.

Example 61

3-[3-(3-Chlorophenyl)-thioureido]-4-methoxy-N-phenyl-benzamide

Prepared according to the procedure described for Example 60 using 3-amino-4-methoxy-N-phenyl-benzamide (0.218 g, 0.90 mmol) and 3-chlorophenyl isothiocyanate (0.12 mL, 0.92 mmol) to give the product (0.286 g); m.p. 165–168° C.

Calculated for $C_{21}H_{18}ClN_3O_2S$: C, 61.23; H, 4.40; N, 10.20. Found: C, 61.01; H, 4.35; N, 10.15.

Example 62

4-Methoxy-N-phenyl-3-(3-phenyl-thioureido)-benzamide

Prepared according to the procedure described for Example 60 using 3-amino-4-methoxy-N-phenyl-benzamide (0.245 g, 1.01 mmol) and phenyl isothiocyanate (0.12 mL, 1.00 mmol) to give the product (0.216 g); m.p. 174–176° C.

Calculated for $C_{21}H_{19}N_3O_2S$: C, 66.82; H, 5.07; N, 11.13. Found: C, 66.34; H, 5.13; N, 11.04.

Example 63

4-Methoxy-N-phenyl-3-[3-(4-trifluoromethyl-phenyl)-thioureido]-benzamide

Prepared according to the procedure described for Example 60 using 3-amino-4-methoxy-N-phenyl-benzamide (0.198 g, 0.82 mmol) and 4-(trifluoromethyl) phenyl isothiocyanate (0.169 g, 0.83 mmol) to give the product (0.306 g); m.p. 194–196° C.

Calculated for $C_{22}H_{18}F_3N_3O_2S$: C, 59.32; H, 4.07; N, 9.43. Found: C, 59.04; H, 4.05; N, 9.35.

Example 64

3-[3-(4-tert-Butyl-phenyl)-thioureido]-4-methoxy-N-phenyl-benzamide

Prepared according to the procedure described for Example 60 using 3-amino-4-methoxy-N-phenyl-benzamide (0.216 g, 0.89 mmol) and 4-t-butylphenyl isothiocyanate (0.176 g, 0.92 mmol) to give the product (0.180 g); m.p. 198–200° C.

Calculated for $C_{25}H_{27}N_3O_2S \cdot 0.33\ H_2O$: C, 68.32; H, 6.34; N, 9.56. Found: C, 68.22; H, 6.49; N, 9.59.

Example 65

3-[3-(4-Chlorophenyl)-thioureido]-4-methoxy-N-phenyl-benzamide

Prepared according to the procedure described for Example 60 using 3-amino-4-methoxy-N-phenylbenzamide (0.243 g, 1.0 mmol) and 4-chlorophenyl isothiocyanate (0.174 g, 1.03 mmol). Trituration in hexanes/ethyl acetate (1:1) gave the product (0.362 g); m.p. 179–180° C.

Calculated for $C_{21}H_{18}ClN_3O_2S$: C, 61.23; H, 4.40; N, 10.20. Found: C, 60.94; H, 4.23; N, 10.03.

Example 66

3-[3-(3-Nitrophenyl)-thioureido]-4-methoxy-N-phenyl-benzamide

Prepared according to the procedure described for Example 60 using 3-amino-4-methoxy-N-phenyl-benzamide (0.243 g, 1.0 mmol) and 3-nitrophenyl isothiocyanate (0.183 g, 1.0 mmol). Trituration in hexanes/ethyl acetate (4:1) gave the product (0.370 g); m.p. 188–189° C.

Calculated for $C_{21}H_{18}N_4O_4S$: C, 59.71; H, 4.29; N, 13.26. Found: C, 58.92; H, 4.23; N, 12.72.

Example 67

4-Methoxy-N-phenyl-3-(3-benzoyl-thioureido)-benzamide

Prepared according to the procedure described for Example 60 using 3-amino-4-methoxy-N-phenyl-benzamide (0.243 g, 1.0 mmol) and benzoyl isothiocyanate (0.171 g, 1.04 mmol) to afford the product (0.371 g); m.p. 219–222° C.

CI Mass Spectrum: $[M+H^+]^+=406$.

Calculated for $C_{22}H_{19}N_3O_3S$: C, 65.17; H, 4.72; N, 10.36. Found: C, 64.98; H, 4.57; N, 10.26.

Example 68

4-Methoxy-N-phenyl-3-[3-(2,3,5,6-tetrafluorophenyl)-thioureido]-benzamide

Prepared according to the procedure described for Example 60 using 3-amino-4-methoxy-N-phenyl-benzamide (0.243 g, 1.0 mmol) and 2,3,5,6-tetrafluorophenyl isothiocyanate (0.224 g, 1.1 mmol) to give the product (0.398 g); m.p. 170–174° C.

Calculated for $C_{21}H_{15}F_4N_3O_2S$: C, 56.12; H, 3.36; N, 9.35. Found: C, 55.74; H, 3.22; N, 9.19.

Example 69

4-Methoxy-N-phenyl-3-(-3-p-tolyl-thioureido)-benzamide

Prepared according to the procedure described for Example 60 using 3-amino-4-methoxy-N-phenyl-benzamide (0.243 g, 1.0 mmol) and 4-methylphenyl isothiocyanate (0.205 g, 1.38 mmol). The reaction was incomplete after 2 days, so the mixture was diluted to 30 mL with ethyl acetate, and a small additional portion of 4-methylphenyl isothiocyanate was added. The mixture was boiled on a steambath until no solvent remained and the residue triturated in hexanes/ethyl acetate (4:1) and filtered to afford the product (0.255 g); m.p. 156–158° C.

CI Mass Spectrum: $[M+H^+]^+=392$.

Calculated for $C_{22}H_{21}N_3O_2S.0.5 H_2O$: C, 65.97; H, 5.54; N, 10.49. Found: C, 66.16; H, 5.60; N, 10.31.

Example 70

3-[3-(3,5-Dichlorophenyl)-thioureido]-4-N-phenyl-benzamide

Prepared according to the procedure described for Example 60 using 3-aminobenzanilide (0.213 g, 1.0 mmol) and 3,5-dichlorophenyl isothiocyanate (0.208 g, 1.0 mmol). Trituration in ethyl acetate gave the product (0.304 g); m.p. 174–177° C.

APCI Mass Spectrum, M=416.1.

Calculated for $C_{20}H_{15}Cl_2N_3OS$: C, 57.70; H, 3.63; N, 10.09. Found: C, 58.03; H, 3.57; N, 9.99.

Example 71

3-[3-(3,5-Dichlorophenyl)-thioureido]-4-methyl-N-phenyl-benzamide

Prepared according to the procedure described for Example 60 using of 3-amino-4-methyl-N-phenyl-benzamide (0.5 g, 2.2 mmol) and 3,5-dichlorophenyl isothiocyanate (0.458 g, 2.2 mmol). Trituration in ethyl acetate afforded the product (0.802 g) in two crops; m.p. 182–184° C.

Calculated for $C_{21}H_{17}Cl_2N_3OS$: C, 58.61; H, 3.98; N, 9.76. Found: C, 58.54; H, 3.77; N, 9.61.

Example 72

3-[3-(3,4-Dimethoxyphenyl)-thioureido]-4-methoxy-N-phenyl-benzamide

A mixture of 3-amino-4-methoxy-N-phenyl-benzamide (0.972 g, 4.0 mmol), 3,4-dimethoxyphenyl isothiocyanate (0.787 g, 4.0 mmol), and ethyl acetate (25 mL) was heated briefly to 50° C. and then allowed to stand overnight at room temperature. The reaction mixture was diluted with ethyl acetate (~100 mL), heated to 80° C. briefly, then allowed to stand 5 days at room temperature. The precipitate was filtered off to afford the product (0.552 g); m.p. 170–171° C.

Calculated for $C_{23}H_{23}N_3O_4S$: C, 63.14; H, 5.30; N, 9.60. Found: C, 63.02; H, 5.44; N, 9.58.

Example 73

3-[3-(4-Chloro-3-trifluoromethylphenyl)-thioureido]-4-methoxy-N-phenyl-benzamide Prepared according to the procedure described for Example 60 using 3-amino-4-methoxy-N-phenyl-benzamide (0.972 g, 4.0 mmol) and 4-chloro-3-(trifluoromethyl)phenyl isothiocyanate (0.961 g, 4.0 mmol). Trituration in hexanes/ethyl acetate (3:2) gave the product (1.91 g); m.p. 172–173° C.

Calculated for $C_{23}H_{17}Cl_2N_3O_2S$: C, 55.06; H, 3.57; N, 8.76. Found: C, 54.88; H, 3.26; N, 8.58.

Example 74

3-[3-(3-Cyanophenyl)-thioureido]-4-methoxy-N-phenyl-benzamide

Prepared according to the procedure described for Example 60 using 3-amino-methoxy-N-phenyl-benzamide (0.972 g, 4.0 mmol) and 3-cyanophenyl) isothiocyanate (0.649 g, 4.0 mmol). Trituration in boiling ethyl acetate/dichloromethane (1:1) gave the product (1.358 g); m.p. 183–185° C.

Calculated for $C_{22}H_{18}Cl_2N_4O_2S.0.2C_4H_8O_2$: C, 65.18; H, 4.70; N, 13.34. Found: C, 64.98; H, 4.80; N, 13.40.

Example 75

4-[3-(2-Methoxy-5-phenylcarbamoyl-phenyl)-thioureido]-benzoic acid

Prepared according to the procedure described for Example 60 using 3-amino-4-methoxy-N-phenylbenzamide (0.972 g, 4.0 mmol) and 4-carboxyphenyl isothiocyanate (0.722 g, 4.0 mmol) to afford the product (1.369 g); m.p. 201–202° C.

Calculated for $C_{22}H_{19}N_3O_4S\cdot 0.25\ H_2O$: C, 62.03; H, 4.61; N, 9.87. Found: C, 61.92; H, 4.73; N, 9.59.

Example 76

3-[3-(3-Acetyl-phenyl)-thioureido]-4-methoxy-N-phenyl-benzamide

Prepared according to the procedure described for Example 60 using 3-amino-4-methoxy-N-phenyl-benzamide (0.971 g, 4.00 mmol) and 3-acetylphenyl isothiocyanate (0.709 g, 4.00 mmol) to afford the product (1.135 g); m.p. 176–177° C.

Calculated for $C_{23}H_{21}N_3O_3S$: C, 65.85; H, 5.05; N, 10.02. Found: C, 65.55; H, 4.93; N, 9.83.

Example 77

3-[3-(4-Chloro-3-nitrophenyl)-thioureido]-4-methoxy-N-phenyl-benzamide

Prepared according to the procedure described for Example 60 using 3-amino-4-methoxy-N-phenyl-benzamide (0.973 g, 4.00 mmol) and 4-chloro-3-nitrophenyl isothiocyanate (0.859 g, 4.00 mmol) to afford the product (1.296 g); m.p. 174–175° C.

Calculated for $C_{21}H_{17}N_4O_4ClS$: C, 55.20; H, 3.75; N, 12.26. Found: C, 55.19; H, 3.87; N, 12.29.

Example 78

3-[3-(4-Fluorophenyl)-thioureido]-4-methoxy-N-phenyl-benzamide

A mixture of 3-amino-4-methoxybenzanilide (0.973 g, 4.00 mmol) in ethyl acetate (75 mL) was heated briefly to ~60° C. The mixture was filtered to clarity and 4-fluorophenyl isothiocyanate (0.49 mL, 4.04 mmol) was added to the filtrate. After 3 days, the mixture was concentrated until a crystalline precipitate was obtained, then allowed to stand several hours at room temperature. Filtration followed by trituration of the collected solid in ether afforded the product (0.4949 g); m.p. 182–183° C.

Calculated for $C_{21}H_{18}N_3O_2FS$: C, 63.78; H, 4.59; N, 10.63. Found: C, 63.72; H, 4.46; N, 10.45.

Example 79

3-[3-(3,5-Dichlorophenyl)-thioureido]-4-methoxy-N-(4-methoxy-phenyl)-benzamide

A mixture of 3-amino-4-methoxy-N-(4-methoxyphenyl)-benzamide from Example 3 (0.681 g, 2.50 mmol) in ethyl acetate (80 mL) was heated briefly to 60° C. then filtered to clarity and mixed with 3,5-dichlorophenyl isothiocyanate (0.511 g, 2.50 mmol). The reaction was allowed to stand for 3 days at room temperature then concentrated to two-thirds volume and allowed to stand overnight. Filtration afforded the product (0.948 g); m.p 175–182° C.

Calculated for $C_{22}H_{19}N_3O_3Cl_2S$: C, 55.47; H, 4.02; N, 8.82. Found: C, 55.42; H, 3.90; N, 8.73.

Example 80

3-[3-(3,5-Dichlorophenyl)-thioureido]-4-ethoxy-N-phenyl-benzamide

Prepared according to the procedure described for Example 60 using 3-amino-4-ethoxy-N-phenyl-benzamide from Example 10 (0.335 g, 1.30 mmol) and 3,5-dichlorophenyl isothiocyanate (0.266 g, 1.30 mmol) to give the product (0.4609 g); m.p. 201–202° C.

Calculated for $C_{22}H_{19}N_3O_2Cl_2S\cdot 1/3\ H_2O$: C, 56.66; H, 4.25; N, 9.01. Found: C, 56.64; H, 3.98; N, 8.87.

Example 81

4-Methoxy-N-phenyl-3-(3-pyridin-3-yl-thioureido)-benzamide

Prepared according to the procedure described for Example 60 using 3-amino-4-methoxy-N-phenyl-benzamide (0.972 g, 4.00 mmol) and 3-pyridyl isothiocyanate (0.565 g, 4.15 mmol). Trituration in hexanes/ethyl acetate (3:2) gave the product (1.441 g); m.p. 178–179° C.

Calculated for $C_{20}H_{18}N_4O_2S$: C, 63.47; H, 4.79; N, 14.80. Found: C, 62.88; H, 4.78; N, 14.65.

Example 82

4-[3-(2-Methoxy-5-phenylcarbamoyl-phenyl)-thioureido]-benzenesulfonic Acid

Prepared according to the procedure described for Example 60 using 3-amino-4-methoxy-N-phenyl-benzamide (0.972 g, 4.00 mmol) and 4-sulfophenyl isothiocyanate sodium salt (1.02 g, 4.0 mmol), except that dimethyl formamide was used as solvent. The dimethyl formamide was removed by rotary evaporator at 60° C. to afford the product, m.p. >280° C., after trituration in ethyl acetate.

Calculated for $C_{21}H_{18}N_3O_5S_2Na\cdot 1.25\ H_2O\cdot 0.67\ DMF$: C, 50.16; H, 4.61; N, 9.33. Found: C, 50.21; H, 4.32; N, 8.91.

Example 83

4-Methoxy-3-[3-(4-methoxy-phenyl)-thioureido]-N-phenyl-benzamide

Prepared according to the procedure described for Example 60 using 3-amino-4-methoxy-N-phenyl-benzamide (0.972 g, 4.00 mmol) and 4-methoxyphenyl isothiocyanate (0.77 g, 5.16 mmol), except that after collection of the product obtained upon trituration with hexanes/ethyl acetate, an impurity was present. The impurity was removed by slurrying the solid in dichloromethane/methanol 95:5 followed by filtration to afford the product (0.505 g); m.p. 168–169° C.

Calculated for $C_{22}H_{21}N_3O_3S$: C, 64.85; H, 5.19; N, 10.31. Found: C, 64.55; H, 5.17; N, 10.18.

Example 84

4-Methoxy-N-phenyl-3-[3-(3-trifluoromethyl-phenyl)-thioureido]-benzamide

Prepared according to the procedure described for Example 60 using 3-amino-4-methoxy-N-phenyl-benzamide (0.972 g, 4.00 mmol) and 3-trifluoromethylphenyl isothiocyanate (0.82 g, 4.04 mmol). Trituration in hexanes/ethyl acetate gave the product (1.12 g) in two crops; m.p. 177–178° C.

Calculated for $C_{22}H_{18}N_3O_2F_3S$: C, 59.32; H, 4.07; N, 9.43. Found: C, 59.33; H, 3.85; N, 9.37.

Example 85

3-[3-(3,4-Dichlorophenyl)-thioureido]-4-methoxy-N-phenyl-benzamide

Prepared according to the procedure described for Example 60 using 3-amino-4-methoxy-N-phenylbenzamide (0.972 g, 4.00 mmol) and 3,4-dichlorophenyl isothiocyanate (0.82 g, 4.02 mmol) to afford the product (1.40 g) in two crops; m.p. 174–175° C.

Calculated for $C_{21}H_{17}N_3O_2Cl_2S$: C, 56.51; H, 3.84; N, 9.41. Found: C, 56.54; H, 3.60; N, 9.36.

Example 86

1-{3-[3-(3,5-Dichlorophenyl)-thioureido]-4-methoxyphenyl}-3-phenyl-urea

Prepared according to the procedure described for Example 78 using 1-(4-methoxy-3-aminophenyl)-3-phenyl-urea from Example 24, Step C (0.390 g, 1.52 mmol) and 3,5-dichlorophenyl isothiocyanate (0.311 g, 1.52 mmol). Filtration without trituration afforded the product (0.5187 g); m.p. 218–219° C.

Calculated for $C_{21}H_{18}N_4O_2Cl_2S$: C, 54.67; H, 3.93; N, 12.14. Found: C, 54.73; H, 3.95; N, 11.89.

Example 87

N-{3-[3-(3,5-Dichlorophenyl)-thioureido]-4-methoxy-phenyl}-benzamide

Prepared according to the procedure described for Example 78 using N-(3-amino-4-methoxyphenyl)-benzamide from Example 21 (0.88 g, 3.62 mmol) and 3,5-dichlorophenyl isothiocyanate (0.739 g, 3.62 mmol). Filtration without trituration afforded the product (1.31 g); m.p. 194–195° C.

Calculated for $C_{21}H_{17}N_3O_2Cl_2S$: C, 56.51; H, 3.84; N, 9.41. Found: C, 56.30; H, 3.74; N, 9.22.

Example 88

4-Methoxy-3-[3-(4-nitrophenyl)-thioureido]-N-phenyl-benzamide

Prepared according to the procedure described for Example 60 using 3-amino-4-methoxy-N-phenyl-benzamide (0.976 g, 4.02 mmol) and 4-nitrophenyl isothiocyanate (0.723 g, 4.02 mmol) to afford the product (1.39 g) after trituration in ether; m.p. 183–184° C.

Calculated for $C_{21}H_{18}N_4O_4S \cdot 1/6$ EtOAc: C, 59.53; H, 4.46; N, 12.82. Found: C, 59.01; H, 4.08; N, 12.71.

Example 89

3-[3-(3,5-Bis-trifluoromethylphenyl)-thioureido]-4-methoxy-N-phenyl-benzamide

Prepared according to the procedure described for Example 60 using 3-amino-4-methoxy-N-phenyl-benzamide (0.972 g, 4.00 mmol) and 3,5-di(trifluoromethyl)phenyl isothiocyanate (1.08 g, 3.98 mmol) to afford the product (1.076 g); m.p. 192–193° C.

Calculated for $C_{23}H_{17}N_3O_2F_6S$: C, 53.80; H, 3.34; N, 8.18. Found: C, 53.71; H, 3.15; N, 8.15.

Example 90

4-Methoxy-N-phenyl-3-[3-(4-sulfamoyl-phenyl)-thioureido]-benzamide

Prepared according to the procedure described for Example 60 using 3-amino-4-methoxy-N-phenyl-benzamide (0.974 g, 4.01 mmol) and 4-isothiocyanatobenzenesulfonamide (0.858 g, 4.00 mmol) to afford the product (0.858 g); m.p. 193–195° C.

Calculated for $C_{21}H_{20}N_4O_4S_2$: C, 55.25; H, 4.42; N, 12.27. Found: C, 54.91; H, 4.34; N, 12.01.

Example 91

3-[3-(3,5-Dichlorophenyl)-thioureido]-N-(4-fluorophenyl)-4-methoxy-benzamide

Prepared according to the procedure described for Example 60 using 3-amino-N-(4-fluorophenyl)-4-methoxy-benzamide from Example 8 (0.520 g, 2.00 mmol) and 3,5-dichlorophenyl isothiocyanate (0.409 g, 2.00 mmol). Filtration afforded the product (0.71 g) in two crops; m.p. 175–178° C.

Calculated for $C_{21}H_{16}N_3O_2Cl_2FS$: C, 54.32; H, 3.47; N, 9.05. Found: C, 54.07; H, 3.53; N, 8.88.

Example 92

N-(4-Chlorophenyl)-3-[3-(3,5-dichlorophenyl)-thioureido]-4-methoxy-benzamide

A mixture of 3-amino-N-(4-chlorophenyl)-4-methoxy-benzamide from Example 2 (1.113 g, 4.02 mmol) and 3,5-dichlorophenyl isothiocyanate (0.820 g, 4.02 mmol) in DMF (10 mL) was allowed to stand at room temperature overnight. The mixture was then diluted with 50 mL $H_2O$ and the precipitate collected by filtration and dried. Trituration in first ether then ethyl acetate followed by filtration afforded the product (1.19 g); m.p. 180–185° C.

Calculated for $C_{21}H_{16}N_3O_2Cl_3S$: C, 52.46; H, 3.35; N, 8.74. Found: C, 52.34; H, 3.51; N, 8.92.

Example 93

3-[3-(4-Dimethylaminophenyl)-thioureido]-4-methoxy-N-phenyl-benzamide

A mixture of 3-amino-4-methoxy-N-phenyl-benzamide (0.975 g, 4.01 mmol), 4-(dimethylamino)phenyl isothiocyanate (0.716 g, 4.00 mmol), and ethyl acetate (20 mL) was allowed to stand at room temperature. After 5 days, the mixture was concentrated to two-thirds volume by rotary evaporator, allowed to stand overnight, then heated to 80 degrees for 4 hours. The precipitate was collected by filtration and the mother liquor heated to 80 degrees for another 3 hours. More precipitate was collected by filtration and the mother liquor again heated to 80 degrees and after 7 hours allowed to cool to room temperature overnight. The remaining liquor was concentrated to dryness and the residue triturated in hexanes and the solid filtered off and washed with ethyl acetate. Combination of all the lots gave the product (0.905 g); m.p. 179–180° C.

Calculated for $C_{23}H_{24}N_4O_2S \cdot 0.1$ M EtOAc: C, 65.46; H, 5.82; N, 13.05. Found: C, 65.24; H, 5.70; N, 12.86.

Example 94

3-[3-(3,5-Dichlorophenyl)-thioureido]-4-methoxy-N-p-tolyl-benzamide

A suspension of 3-amino-4-methoxy-N-p-tolyl-benzamide from Example 7 (0.515 g, 2.01 mmol) in methylene chloride (75 mL) was heated to the boiling point, then 3,5-dichlorophenyl isothiocyanate (0.411 g, 2.01 mmol) was added, and the reaction was allowed to stand at room temperature. After 2 days, the mixture was stripped of solvent at 40° C. and the residue triturated in warm methylene chloride. The solid was filtered off, redissolved in methylene chloride/methanol, and filtered to clarity. Evaporation of the solvent afforded the product (0.305 g); m.p. 178–180° C.

Calculated for $C_{22}H_{19}N_3O_2Cl_2S$: C, 57.40; H, 4.16; N, 9.13. Found: C, 56.99; H, 4.11; N, 9.07.

Example 95

4-Methoxy-N-phenyl-3-(3-m-tolyl-thioureido)-benzamide

Prepared according to the procedure described for Example 60 using 3-amino-4-methoxy-N-phenyl-benzamide (0.973 g, 4.00 mmol) and 3-methylphenyl isothiocyanate (0.55 mL, 4.07 mmol) to afford the product (0.305 g) in two crops; m.p. 168–117° C.

Calculated for $C_{22}H_{21}N_3O_2S.0.1\ M\ H_2O$ ; C, 67.18; H, 5.43; N, 10.69. Found: C, 67.00; H, 5.32; N, 10.55.

Example 96

3-[3-(3,5-Dichlorophenyl)-thioureido]-4-fluoro-N-phenyl-benzamide

Prepared according to the procedure described for Example 60 using 3-amino-4-fluoro-N-phenyl-benzamide from Example 9 (0.481 g, 2.09 mmol) and 3,5-dichlorophenyl isothiocyanate (0.427 g, 2.09 mmol). Filtration afforded the product (0.45 g) in two crops; m.p. 173–175° C.

Calculated for $C_{20}H_{14}N_3OCl_2SF$: C, 55.31; H, 3.25; N, 9.67. Found: C, 55.21; H, 3.12; N, 9.62.

Example 97

N-(3,4-Dichlorophenyl)-3-(3,5-dichlorophenyl)-thioureido]-4-methoxy-benzamide

Prepared according to the procedure described for Example 78 using 3-amino-4-methoxy-N-(3,4-dichlorophenyl)-benzamide from Example 4 (0.932 g, 3.00 mmol) and 3,5-dichlorophenyl isothiocyanate (0.335 g, 1.64 mmol). After 2 days, filtration afforded the product (0.426 g); m.p. 189–191° C.

Calculated for $C_{21}H_{15}N_3O_2Cl_4S$: C, 48.95; H, 2.93; N, 8.16. Found: C, 48.96; H, 2.87; N, 8.05.

Example 98

4-Methoxy-N-phenyl-3-(3-o-tolyl-thioureido)-benzamide

A mixture of 3-amino-4-methoxy-N-phenyl-benzamide (0.972 g, 4.00 mmol), 2-methylphenyl isothiocyanate (0.55 mL, 4.11 mmol, and ethyl acetate 20 mL) was allowed to stand at room temperature. After 4 days, the reaction was heated to 80° C. for 3 hours then allowed to stand at room temperature for an additional 5 days. Filtration afforded the product (0.804 g); m.p. 172–174° C.

Calculated for $C_{22}H_{21}N_3O_2S$: C, 67.50; H, 5.41; N, 10.73. Found: C, 66.96; H, 5.47; N, 10.56.

Example 99

3-[3-(3,5-Dimethylphenyl)-thioureido]-4-methoxy-N-phenyl)-benzamide

Prepared according to the procedure described for Example 98 using 3-amino-4-methoxy-N-phenyl-benzamide (0.974 g, 4.01 mmol) and 3,5-dimethylphenyl isothiocyanate (0.66 g, 4.04 mmol) to afford the product (0.42 g); m.p. 203–205° C.

Calculated for $C_{23}H_{23}N_3O_2S$: C, 68.12; H, 5.72; N, 10.36. Found: C, 67.83; H, 5.66; N, 10.26.

Example 100

3-[3-(3,4-Dichlorophenyl)-thioureido]-4-methoxy-N-pyridin-3-yl-benzamide

A solution of 3-amino-4-methoxy-N-pyridin-3-yl-benzamide from Example 5 (0.727 g, 2.99 mmol) and 3,5-dichlorophenyl isothiocyanate (0.611 g, 2.99 mmol) in DMF (25 mL) was allowed to stand at room temperature for 3 days. The solvent was removed in vacuo and the residue diluted with water then allowed to stand overnight. The suspended solid was filtered off and triturated successively with ethyl acetate, ether, then boiling methanol to afford the product (0.57 g); m.p. 179–180° C.

Calculated for $C_{20}H_{16}N_4O_2Cl_2S$: C, 53.70; H, 3.61; N, 12.53. Found: C, 53.54; H, 3.52; N, 12.43.

Example 101

5-[3-(3,5-Dichlorophenyl)-thioureido]-2-fluoro-N-phenyl-benzamide

Step A: 5-Amino-2-fluoro-N-phenyl-benzamide

Prepared according to the procedure described for Example 1 using oxalyl chloride (3.0 mL, 34.39 mmol), 2-fluoro-5-nitrobenzoic acid (5.00 g, 27.01 mmol), DMF (1.0 mL, 12.92 mmol), and aniline (5.0 mL, 54.88 mmol) to afford the pure product (5.76 g); m.p. 120–122° C.

Calculated for $C_{13}H_{11}N_2OF$: C, 67.82; H, 4.82; N, 12.17. Found: C, 67.59; H, 4.80; N, 12.08.

Step C: 5-[3-(3,5-Dichlorophenyl)-thioureido]-2-fluoro-N-phenyl-benzamide

Prepared according to the procedure described for Example 60 using 5-amino-2-fluoro-N-phenyl-benzamide (0.920 g, 4.00 mmol) and 3,5-dichlorophenyl isothiocyanate (0.817 g, 4.00 mmol) to afford the product (1.52 g); m.p. 195–196° C.

Calculated for $C_{20}H_{14}N_3OCl_2F$: C, 55.31; H, 13.25; N, 9.68. Found: C, 55.47; H, 3.28; N, 9.43.

Example 102

N-(3,4-Dimethylphenyl)-4-methoxy-3-(3-m-tolyl-thioureido)-benzamide

A solution of 3-amino-N-(3,4-dimethylphenyl)-4-methoxy-benzamide from Example 6 (0.541 g, 2.00 mmol) and 3-methylphenyl isothiocyanate (0.28 mL, 2.07 mmol) in ethyl acetate (35 mL) was boiled until nearly all the solvent had evaporated. Filtration after 2 days at room temperature afforded the product (0.44 g) in two crops; m.p. 155–160° C.

Calculated for $C_{24}H_{25}N_3O_2S$: C, 68.71; H, 6.01; N, 10.02. Found: C, 68.11; H, 6.09; N, 9.81.

Example 103

N-(3,5-Dimethylphenyl)-4-methoxy-3-(3-m-tolyl-thioureido)-benzamide

Prepared according to the procedure described for Example 102 using 3-amino-N-(3,5-dimethylphenyl)-4-methoxy-benzamide from Example 11 (0.542 g, 2.01 mmol) and 3-methylphenyl isothiocyanate (0.28 mL, 2.07 mmol) to afford the product (0.41 g); m.p. 188–189° C.

Calculated for $C_{24}H_{25}N_3O_2S$: C, 68.71; H, 6.01; N, 10.02. Found: C, 68.59; H, 5.93; N, 9.85.

Example 104

N-(3-Chloro-4-methylphenyl)-3-[3-(3,5-dichlorophenyl)-thioureido]-4-methoxy-benzamide A solution of 3-amino-N-(3-chloro-4-methylphenyl)-4-methoxy-benzamide from Example 12 (0.581 g, 2.00 mmol) and 3,5-dichlorophenyl isothiocyanate (0.409 g, 2.00 mmol) in dichloromethane (40 mL) and DMF (3 mL) was allowed to stand at room temperature. After 16 hours, filtration afforded the product (0.57 g); m.p. 195–196° C.

Calculated for $C_{22}H_{18}N_3O_2Cl_3S$: C, 53.40; H, 3.67; N, 8.49. Found: C, 53.13; H, 3.54; N, 8.37.

Example 105

N-(3,4-Dichlorophenyl)-4-methoxy-3-[3-(4-sulfamoyl-phenyl)-thioureido]-benzamide Prepared according to the procedure described for Example 78 using 3-amino-N-(3,4-dichlorophenyl)-4-methoxy-benzamide from Example 39 (0.622 g, 2.00 mmol) and 4-isothiocyanatobenzenesulfonamide (0.428 g, 2.00 mmol). Filtration without trituration afforded the product (0.714 g); m.p. 190–193° C.

Calculated for $C_{21}H_{18}N_4O_4S_2Cl_2$: C, 48.00; H, 3.45; N, 10.66. Found: C, 47.86; H, 3.64; N, 10.40.

Example 106

3-[3-(3,5-Dichlorophenyl)-thioureido]-4-methylsulfanyl-N-phenyl-benzamide

A solution of 3-amino-N-phenyl-4-methylsulfanyl-benzamide from Example 20 (0.327 g, 1.27 mmol) and 3,5-dichlorophenyl isothiocyanate (0.258 g, 1.26 mmol) in dichloromethane (50 mL) was briefly warmed to 40° C. and then allowed to stand at room temperature. After 4 days, DMF (5 mL) was added and the mixture allowed to stand for 4 hours, then the solvent was removed in vacuo and the residue mixed with water. Filtration afforded the product (0.3635 g); m.p. 172–175° C. after trituration in ether.

Calculated for $C_{21}H_7N_3OS_2Cl_2 \cdot H_2O$: C, 53.50; H, 3.85; N, 8.92. Found: C, 53.48; H, 3.83; N, 8.86.

Example 107

3-[3-(3,5-Dichlorophenyl)-thioureido]-N-(3,4-difluoro-phenyl)-4-methoxy-benzamide Prepared according to the procedure described for Example 60 using 3-amino-N-(3,4-difluorophenyl)-4-methoxy-benzamide from Example 15 (0.834 g, 3.00 mmol) and 3,5-dichlorophenyl isothiocyanate (0.6124 g, 3.00 mmol) to afford the product (1.206 g) in 3 crops; m.p. 180–183° C.

Calculated for $C_{21}H_{15}N_3O_2F_2Cl_2S$: C, 52.29; H, 3.13; N, 8.71. Found: C, 52.02; H, 3.07; N, 8.61.

Example 108

N-(3-Chlorophenyl)-3-[3-(4-fluorophenyl)-thioureido]-4-methoxy-benzamide

Prepared according to the procedure described for Example 100 using 3-amino-N-(3-chlorophenyl)-4-methoxy-benzamide from Example 16 (0.5545 g, 2.01 mmol) and 4-fluorophenyl isothiocyanate (0.3073 g, 2.01 mmol), and omitting the trituration in methanol to afford the product (0.775 g); m.p. 184–185° C.

Calculated for $C_{21}H_{17}N_3O_2SFCl$: C, 58.67; H, 3.99; N, 9.77. Found: C, 58.51; H, 3.94; N, 9.81.

Example 109

3-[3-(3,5-Dichlorophenyl)-thioureido]-4-methoxy-N-phenyl-benzenesulfonamide

A suspension of 3-amino-4-methoxy-N-phenyl-benzenesulfonamide (0.4514 g, 1.62 mmol) in ethyl acetate was heated until a solution was obtained. 3,5-Dichlorophenyl isothiocyanate (0.3310 g, 1.62 mmol) was added and the mixture allowed to stand at room temperature. After 4 days, the reaction was concentrated to 1/3 of its original volume and allowed to stand overnight. The solution was concentrated to an oil which was triturated with hexanes and the resulting solid filtered off, dried, and triturated in ether to afford the product (0.2275 g); m.p. 163–165° C.

Calculated for $C_{20}H_{17}N_3O_3S_2Cl_2 \cdot 0.67 H_2O$: C, 48.58; H, 3.74; N, 8.50. Found: C, 48.54; H, 3.70; N, 8.21.

Example 110

4-Ethyl-N-phenyl-3-[3-(3-trifluoromethylphenyl)-thioureido]-benzamide

Prepared according to the procedure described for Example 78 using 3-amino-N-phenyl-4-ethyl-benzamide from Example 17 (0.961 g, 4.00 mmol) and 3-(trifluromethyl)phenyl isothiocyanate (0.82 g, 4.04 mmol). Filtration without trituration afforded the product (1.4641 g); m.p. 166–167° C.

Calculated for $C_{23}H_{20}N_3OSF_3 \cdot 0.43$ EtOAc: C, 61.68; H, 4.91; N, 8.73. Found: C, 61.67; H, 4.89; N, 8.73.

Example 111

4-Ethyl-N-(3,4-difluorophenyl)-3-[3-(3-trifluoromethyl-phenyl)-thioureido]-benzamide Prepared according to the procedure described for Example 60 using 3-amino-N-(3,4-difluoro-phenyl)-4-ethyl-benzamide from Example 19 (1.5216 g, 5.51 mmol) and 3-(trifluoromethyl)phenyl isothiocyanate (1.12 g, 5.51 mmol) to afford the product (1.78 g); m.p. 169–170° C.

Calculated for $C_{23}H_{18}N_3OSF_5 \cdot 0.33$ EtOAc: C, 57.44; H, 4.09; N, 8.26. Found: C, 57.24; H, 3.94; N, 8.36.

Example 112

3-({3-[2-Methoxy-5-(pyridin-3-ylcarbamoyl)-phenyl]-thioureido}-benzoic acid

Prepared according to the procedure described for Example 60 using 3-amino-4-methoxy-N-pyridin-3-yl-benzamide from Example 5 (0.72 g, 3.0 mmol) and 3-carboxyphenyl isothiocyanate (0.53 g, 3.0 mmol). Trituration in ethyl acetate then hot methanol gave the product (1.0 g); m.p. 191–192° C.

Calculated for $C_{21}H_{18}N_4O_4S \cdot 0.66$ $CH_3OH$: C, 58.63; H, 4.70; N, 12.62. Found: C, 58.54; H, 4.32; N, 12.98.

Example 113

3-[3-(2-Methoxy-5-phenylcarbamoyl-phenyl)-thioureido]-benzoic acid

A mixture of 4-methoxy-3-amino-N-phenyl-benzamide (0.73 g, 3.0 mmol) and 3-carboxyphenyl isothiocyanate (0.54 g, 3.0 mmol) in ethyl acetate (60 mL) was warmed briefly to 50° C. and then allowed to stand overnight at room temperature. The mixture was then rewarmed to 50° C., filtered, and concentrated to dryness. Trituration of the residue in ethyl acetate followed by filtration afforded the product (1.083 g); m.p. 196–197° C.

Calculated for $C_{22}H_{19}N_3O_4S$: C, 62.69; H, 4.54; N, 9.97. Found: C, 62.43; H, 4.55; N, 9.83.

Example 114

3,4-Dichloro-N-{4-fluoro-3-[3-3-trifluoromethylphenyl)-thioureido]-phenyl}-benzamide Prepared according to the procedure described for Example 60 using 3,4-dichloro-N-(3-amino-4-fluorophenyl)-benzamide from Example 22 (0.69 g, 2.3 mmol) and 3-trifluoromethylphenyl isothiocyanate (0.47 g, 2.3 mmol) to afford the product (0.532 g); m.p. 172–174° C.

Calculated for $C_{21}H_{13}Cl_2F_4N_3OS$: C, 50.21; H, 2.61; N, 8.37. Found: C, 50.30; H, 2.63; N, 8.14.

Example 115

3,4-Dichloro-N-{3-[3-(3,5-dichlorophenyl)-thioureido]-4-methoxyphenyl}-benzamide Prepared according to the procedure described for Example 60 using 3,4-dichloro-N-(3-amino-4-methoxyphenyl)-benzamide from Example 23, Step B (0.72 g, 2.3 mmol) and 3,5-dichlorophenyl isothiocyanate (0.47 g, 2.3 mmol) to afford the product (0.3 g) after chromatography on silica gel using hexane/ethyl acetate 3:2 as eluant; m.p. 183–186° C.

Calculated for $C_{21}H_{15}Cl_4N_3O_2S$: C, 48.95; H, 2.93; N, 8.16. Found: C, 49.16; H, 3.18; N, 8.02.

Example 116

3-(3,5-Dichloro-benzenesulfonlylamino)-4-methoxy-N-(3,4-difluorophenyl)-benzamide A solution of 3-amino-4-methoxy-N-(3,4-difluorophenyl)-benzamide from Example 15 (0.834 g, 3.00 mmol), 3,5-dichlorobenzenesulfonyl chloride (0.736 g, 3.00 mmol) and a catalytic amount of 4-dimethylaminopyridine in pyridine (10 mL) was stirred under nitrogen at room temperature. After 16 hours, the solvent was removed in vacuo and the residue shaken with a mixture of ethyl acetate and 1N HCl then filtered. The layers were separated and the organic layer washed with brine, dried with $MgSO_4$, concentrated to dryness, triturated in hexanes and filtered to afford a solid which was combined with that obtained in the filtration step to afford the product (1.38 g); m.p. 228–231° C.

Calculated for $C_{20}H_{14}Cl_2F_2N_2O_4S$: C, 49.30; H, 2.90; N, 5.75. Found: C, 48.61; H, 2.97; N, 5.58.

Example 117

3-(3,5-Dichloro-benzenesulfonylamino)-4-methoxy-N-(3,4-dichlorophenyl)-benzamide Prepared according to the procedure described for Example 116 using 3-amino-4-methoxy-N-(3,4-dichlorophenyl)-benzamide from Example 4 (0.932 g, 3.00 mmol), 3,5-dichlorobenzenesulfonyl chloride (0.737 g, 3.00 mmol) and 4-dimethylaminopyridine to afford the product (1.53 g); m.p. >230° C. (dec).

Calculated for $C_{20}H_{14}Cl_4N_2O_4S$: C, 46.18; H, 2.71; N, 5.38. Found: C, 47.02; H, 2.82; N, 5.37.

Example 118

3-(3,5-Dichloro-benzenesulfonylamino)-4-methoxy-N-phenyl-benzamide

Prepared according to the procedure described for Example 116 using 3-amino-4-methoxy-N-phenyl-benzamide (0.7296 g, 3.00 mmol), 3,5-dichlorobenzenesulfonyl chloride (0.7327 g, 3.00 mmol), and 4-dimethylaminopyridine to obtain the product (1.01 g); m.p. 222–228° C.

Calculated for $C_{20}H_{16}N_2O_4Cl_2S$: C, 53.23; H, 3.57; N, 6.21. Found: C, 53.23; H, 3.51; N, 6.11.

Example 119

3-Methanesulfonylamino-4-methoxy-N-(3,4-dichlorophenyl)-benzamide

Prepared according to the procedure described for Example 116 using 3-amino-4-methoxy-N-(3,4-dichlorophenyl)-benzamide from Example 4 (0.6117 g, 1.97 mmol) and methanesulfonic anhydride (0.2505 g, 1.44 mmol) for 7 days. No product was obtained in the initial filtration step. Trituration in ethyl acetate/hexane (1:1) followed by recrystallization from ethyl acetate afforded the product (0.0639 g); m.p. 226–228° C.

Calculated for $C_{15}H_{14}N_2O_4SCl_2$: C, 46.28; H, 3.63; N, 7.20. Found: C, 46.21; H, 3.66; N, 7.11.

Example 120

3-Benzenesulfonylamino-methoxy-N-phenyl-benzamide

A mixture of 3-amino-4-methoxy-N-phenyl-benzamide (0.9726 g, 4.00 mmol), triethylamine (0.56 mL, 4.02 mmol), and benzenesulfonyl chloride (0.51 mL, 4.00 mmol) in ethyl acetate (70 mL) was heated briefly to obtain a solution. The reaction was stirred overnight at room temperature under nitrogen. An additional equivalent of triethylamine and 1/2 equivalent of benzenesulfonyl chloride was added and the mixture heated to 50–60° C. After 7 hours, the solvent was removed in vacuo and the residue dissolved in ethyl acetate and washed with 1N HCl followed by saturated $NaHCO_3$. The organic layer was filtered, dried with $MgSO_4$, and stripped of solvent by rotary evaporator. Trituration of the residue in hexane/ethyl acetate (4:1) afforded the product (0.268 g); m.p. 190–194° C.

Calculated for $C_{20}H_{18}N_2O_4S$: C, 62.81; H, 4.74; N, 7.32. Found: C, 62.43; H, 4.86; N, 7.07.

Example 121

3-(4-Methoxy-benzenesulfonylamino)-4-methoxy-N-phenyl-benzamide

A mixture of 4-methoxybenzenesulfonyl chloride (2.21 g, 10.0 mmol), 3-amino-4-methoxy-N-phenyl-benzamide (2.43 g, 10.0 mmol) and pyridine (25 mL) was allowed to stand at room temperature until thin layer chromatography indicated the reaction to be complete. The mixture was then partitioned between water (400 mL) and ethyl acetate (400 mL). The layers were separated and the organic layer washed with water (2×400 mL), 1N HCL (100 mL), and brine (100 mL) dried (magnesium sulfate), filtered and stripped of solvent. Trituration of the residue in hexanes/ethyl acetate (1:1) and filtration afforded the product (3.754 g); m.p. 184–186° C.

Calculated for $C_{21}H_{20}N_2O_5S$: C, 61.15; H, 4.89; N, 6.79. Found: C, 61.20; H, 5.03; N, 6.78.

Example 122

3-(3-Nitro-benzenesulfonylamino)-4-methoxy-N-phenyl-benzamide

Prepared according to the procedure described for Example 121 using 3-nitrobenzenesulfonyl chloride (2.44 g, 10 mmol) and 3-amino-4-methoxy-N-phenyl-benzamide (2.43 g, 10.0 mmol) to afford the product (3.522 g); m.p. 208–210° C.

Calculated for $C_{20}H_{17}N_3O_6S$: C, 56.20; H, 4.01; N, 9.83. Found: C, 56.43; H, 4.10; N, 9.81.

Example 123

3-(3-Chloro-benzenesulfonylamino)-4-methoxy-N-phenyl-benzamide

Prepared according to the procedure described for Example 121 using 3-chlorobenzenesulfonyl chloride (2.27 g, 10 mmol) and 3-amino-4-methoxy-N-phenyl-benzamide (2.43 g, 10.0 mmol) to afford the product (3.846 g); m.p. 197–199° C.

Calculated for $C_{20}H_{17}ClN_2O_4S$: C, 56.20; H, 4.01; N, 9.83. Found: C, 56.43; H, 4.10; N, 9.81.

Example 124

3-(4-Methyl-benzenesulfonylamino)-4-methoxy-N-phenyl-benzamide

Prepared according to the procedure described for Example 121 using 4-methylbenzenesulfonyl chloride (2.06 g, 10 mmol) and 3-amino-4-methoxy-N-phenyl-benzamide (2.43 g, 10.0 mmol) to afford the product (3.053 g); m.p. 200–202° C.

Calculated for $C_{21}H_{20}N_2O_4S$: C, 63.62; H, 5.08; N, 7.07. Found: C, 63.43; H, 5.18; N, 6.86.

Example 125

3-(4-Fluoro-benzenesulfonylamino)-4-methoxy-N-phenyl-benzamide

Prepared according to the procedure described for Example 121 using 4-fluorobenzenesulfonyl chloride (2.14 g 10 mmol) and 3-amino-4-methoxy-N-phenyl-benzamide (2.43 g, 10.0 mmol) to afford the product (3.522 g); m.p. 209–211° C.

Calculated for $C_{20}H_{17}FN_2O_4S$: C, 59.99; H, 4.28; N, 7.00. Found: C, 59.96; H, 4.24; N, 6.87.

Example 126

3-(4,5-Dibromothiophene-2-sulfonylamino)-4-methoxy-N-phenyl-benzamide

Pyridine (5 mL) was added to a mixture of 3-amino-4-methoxy-N-phenyl-benzamide (0.73 g, 3.0 mmol) and 2,3-dibromothiophene-5-sulfonyl chloride (1.0 g, 3.0 mmol) and stirred under an inert atmosphere at room temperature. After 20 hours, the mixture was diluted with water (50 mL), acidified with 4N HCl, and extracted with dichloromethane (2×50 mL). The insoluble material was filtered off and rinsed with water. The combined extracts were washed successively with 2N HCl, water, and saturated brine, then dried over $MgSO_4$. The solvent was removed under reduced pressure and the residue combined with the solid from above to afford the product (0.7 g), m.p. 205–210° C., after recrystallization from ethanol.

Calculated for $C_{18}H_{14}Br_2N_2O_4S_2$·0.3 EtOH: C, 39.89; H, 2.58; N, 5.00. Found: C, 40.26; H, 2.65; N, 5.18.

Example 127

3-(2-Chlorobenzenesulfonylamino)-4-methoxy-N-phenyl-benzamide

Pyridine (5 mL) was added to a mixture of 3-amino-4-methoxy-N-phenyl-benzamide (0.73 g, 3.0 mmol) and 2-chlorobenzenesulfonyl chloride (0.63 g, 3.0 mmol) and stirred under an inert atmosphere at room temperature. After 20 hours, the mixture was diluted with water (50 mL) and acidified with conc. HCl. After 2 hours, the mixture was extracted with dichloromethane (2×50 mL). The combined extracts were washed successively with dilute aqueous HCl, water, and sat. brine then dried over $MgSO_4$ and stripped of solvent under reduced pressure to afford the product (1.1 g); m.p. 107–109° C., after trituration in diethyl ether.

Calculated for $C_{20}H_{17}ClN_2O_4S$·0.3 Ether: C, 57.99; H, 4.59; N, 6.38. Found: C, 57.86; H, 4.65; N, 6.16.

Example 128

3-(4-Trifluoromethyl-benzenesulfonylamino)-4-methoxy-N-phenyl-benzamide

Pyridine (5 mL) was added to a mixture of 4-trifluoromethylbenzenesulfonyl chloride (0.73 g, 3.0 mmol) and 3-amino-4-methoxy-N-phenyl-benzamide (0.73 g, 3.0 mmol) and stirred at room temperature. After 20 hours, the mixture was added to water (50 mL), acidified with 2N HCl, and stirred for an hour. The precipitate was filtered off, rinsed with water, and dried to afford the product (1.2 g); m.p. 197–198° C.

Calculated for $C_{21}H_{17}F_3N_2O_4S$: C, 56.00; H, 3.80; N, 6.22. Found: C, 56.01; H, 3.85; N, 6.12.

Example 129

3-(Butane-1-sulfonylamino)-4-methoxy-N-phenyl-benzamide

Prepared according to the procedure described for Example 128 using 1-butanesulfonyl chloride (0.47 g, 3.0 mmol) and 3-amino-4-methoxy-N-phenyl-benzamide (0.73 g, 3.0 mmol) to afford the product (1.0 g); m.p. 182–183° C. after recrystallization from ethanol.

Calculated for $C_{18}H_{22}N_2O_4S$: C, 59.65; H, 6.12; N, 7.73. Found: C, 59.68; H, 6.09; N, 7.60.

Example 130

3-(Quinoline-8-sulfonylamino)-4-methoxy-N-phenyl-benzamide

Prepared according to the procedure described for Example 126 using 8-quinolinesulfonyl chloride (0.68 g, 3.0 mmol) and 3-amino-4-methoxy-N-phenyl-benzamide (0.73 g, 3.0 mmol) to afford the product (1.0 g); m.p. 187–188° C. after trituration in diethyl ether and recrystallization from ethanol.

Calculated for $C_{23}H_{19}N_3O_4S$: C, 63.73; H, 4.42; N, 9.69. Found: C, 63.68; H, 4.40; N, 9.66.

Example 131

3-(2-Acetylamino-4-methylthiazole-5sulfonylamino)-4-methoxy-N-phenyl-benzamide

Prepared according to the procedure described for Example 126 using 2-acetamido-4-methyl-5-thiazolesulfonyl chloride (0.76 g, 3.0 mmol) and 3-amino-4-methoxy-N-phenyl-benzamide (0.73 g, 3.0 mmol) to afford the product (0.7 g); m.p. 260–261° C. after trituration in diethyl ether.

Calculated for $C_{20}H_{20}N_4O_5S_2$: C, 52.16; H, 4.38; N, 12.17. Found: C, 52.15; H, 4.26; N, 11.87.

Example 132

3-(2,5-Dichlorothiophene-3-sulfonylamino)-4-methoxy-N-phenyl-benzamide

Prepared according to the procedure described for Example 127 using 2,5-dichlorothiophene-3-sulfonyl chloride (0.75 g, 3.0 mmol) and 3-amino- 4-methoxy-N-phenyl-benzamide (0.73 g, 3.0 mmol) to afford the product (0.9 g); m.p. 189–190° C.

Calculated for $C_{18}H_{14}Cl_2N_2O_4S_2$: C, 47.27; H, 3.09; N, 6.13. Found: C, 47.51; H, 3.04; N, 5.91.

Example 133

3-(Naphthalene-1-sulfonylamino)-4-methoxy-N-phenyl-benzamide

Prepared according to the procedure described for Example 127 using 1-naphthalenesulfonyl chloride (0.68 g, 3.0 mmol), 3-amino-4-methoxy-N-phenyl-benzamide (0.73 g, 3.0 mmol), and ethyl acetate instead of dichloromethane to afford the product (0.8 g); m.p. 212–213° C.

Calculated for $C_{24}H_{20}N_2O_4S_2$: C, 66.65; H, 4.66; N, 6.48. Found: C, 66.48; H, 4.75; N, 6.35.

Example 134

3-Ethanesulfonylamino-4-methoxy-N-phenyl-benzamide

Prepared according to the procedure described for Example 121 using ethanesulfonyl chloride (1.5 mL, 15.8 mmol), 3-amino-4-methoxy-N-phenyl-benzamide (2.43 g. 10 mmol) and pyridine (25 mL) to afford the product (3.023 g); m.p. 175–177° C. after trituration in hexanes/ethyl acetate (1:1).

Calculated for $C_{16}H_{18}N_2O_4S$: C, 57.47; H, 5.43; N, 8.38. Found: C, 57.65; H, 5.37; N, 8.35.

Example 135

3-Phenylmethanesulfonylamino-4-methoxy-N-phenyl-benzamide

Prepared according to the procedure described for Example 121 using benzylsulfonyl chloride (1.90 g, 10 mmol), 3-amino-4-methoxy-N-phenyl-benzamide (2.43 g, 10 mmol) and pyridine (25 mL) to afford the product (2.5 g); m.p. 216–216° C. after trituration in hexanes/ethyl acetate (1:1).

Calculated for $C_{21}H_{20}N_2O_4S_2$: C, 63.62; H, 5.08; N, 7.07. Found: C, 63.61; H, 5.00; N, 7.00.

Example 136

3-(3,4-Dichloro-benzenesulfonylamino)-4-methoxy-N-phenyl-benzamide

Prepared according to the procedure described for Example 121 using 3,4-dichlorobenzenesulfonyl chloride (2.45 g, 10 mmol), 3-amino-4-methoxy-N-phenyl-benzamide (2.43 g, 10 mmol) and pyridine (25 mL) to afford the product (4.183 g); m.p. 191–193° C. after trituration in hexanes/ethyl acetate (1:1).

Calculated for $C_{20}H_{16}Cl_2N_2O_4S$: C, 53.23; H, 3.57; N, 6.21. Found: C, 53.30; H, 3.48; N, 6.14.

Example 137

3-(2,4-Difluoro-benzenesulfonylamino)-4-methoxy-N-phenyl-benzamide

Prepared according to the procedure described for Example 121 using 2,4-difluorobenzenesulfonyl chloride (2.19 g, 10 mmol), 3-amino-4-methoxy-N-phenyl-benzamide (2.43 g, 10 mmol), and pyridine (25 mL) to afford the product (3.532 g); m.p. 198–200° C. after trituration in hexanes/ethyl acetate (1:1).

Calculated for $C_{20}H_{16}F_2N_2O_4S$: C, 57.41; H, 3.85; N, 6.70. Found C, 57.52; H, 3.94; N, 6.65.

Example 138

3-(Toluene-3-sulfonylamino)-4-methoxy-N-phenyl-benzamide

Prepared according to the procedure described for Example 121 using 3-methylbenzenesulfonyl chloride (1.91 g, 10 mmol), 3-amino-4-methoxy-N-phenyl-benzamide (2.43 g, 10 mmol), and pyridine (25 mL) to afford the product (3.587 g); m.p. 195–197° C. after trituration in hexanes/ethyl acetate (1:1).

Calculated for $C_{21}H_{20}N_2O_4S$: C, 63.62; H, 5.08; N, 7.07. Found: C, 63.63; H, 5.14; N, 6.96.

Example 139

3-(4-Acetylamino-benzenesulfonylamino)-4-methoxy-N-phenyl-benzamide

Prepared according to the procedure described for Example 121 using N-acetylsufanilyl chloride (2.33 g, 10 mmol), 3-amino-4-methoxy-N-phenyl-benzamide (2.43 g, 10 mmol), and pyridine (25 mL) to afford the product (1.80 g); m.p. 250–251° C. after trituration in hexanes/ethyl acetate (1:1).

Calculated for $C_{22}H_{21}N_3O_5S$: C, 60.12; H, 4.82; N, 9.56. Found: C, 60.04; H, 4.90; N, 9.47.

Example 140

3-(Naphthalene-2-sulfonylamino)-4-methoxy-N-phenyl-benzamide

Prepared according to the procedure described for Example 121 using 2-napthalenesulfonyl chloride (2.28 g, 10 mmol), 3-amino-4-methoxy-N-phenyl-benzamide (2.43 g, 10 mmol), and pyridine (25 mL) to afford the product (4.139 g); m.p. 223–225° C. after trituration in hexanes/ethyl acetate (1:1).

Calculated for $C_{24}H_{20}N_3O_5S$: C, 66.65; H, 4.66; N, 6.48. Found: C, 66.44; H, 4.55; N, 6.37.

Example 141

3-(1-Methyl-1H-imidazole-4-sulfonylamino)-4-methoxy-N-phenyl-benzamide

Pyridine (25 mL) was added to a mixture of 3-amino-4-methoxy-N-phenyl-benzamide (2.43 g, 10 mmol) and 1-methylimidazole-4-sulfonyl chloride (1.82 g, 10 mmol) and the mixture agitated then allowed to stand at room temperature. After 4 days, the mixture was partitioned between ethyl acetate (400 mL) and water (400 mL). The insoluble material was collected by filtration, washed with water, and air dried. The organic extract was washed with water (2× 400 mL), 1N HCl (100 mL), and brine (100 mL), then dried over magnesium sulfate, filtered, and stripped of solvent. The residue was combined with the solid obtained above to afford the product (3.07 g); m.p. 250–252° C., after trituration in hexanes/ethyl acetate (1:1).

Calculated for $C_{18}H_{18}N_4O_5S$: C, 55.95; H, 4.70; N, 14.50. Found: C, 55.99; H, 4.74; N, 14.53.

Example 142

3-(Thiophene-2-sulfonylamino)-4-methoxy-N-phenyl-benzamide

Prepared according to the procedure described for Example 121 using 2-thiophenesulfonyl chloride (1.82 g, 10 mmol), 3-amino-4-methoxy-N-phenyl-benzamide (2.43 g, 10 mmol), and pyridine (25 mL) to afford the product (3.457 g); m.p. 180–183° C. after trituration in hexanes/ethyl acetate (1:1).

Calculated for $C_{18}H_{16}N_2O_4S_2$: C, 55.65; H, 4.15; N, 7.21. Found: C, 55.80; H, 4.13; N, 7.11.

Example 143

3-(5-Dimethylaminonaphthalene-1-sulfonylamino)-4-methoxy-N-phenyl-benzamide Pyridine (5 mL) was added to a mixture of 3-amino-4-methoxy-N-phenyl-benzamide (0.73 g, 3.0 mmol) and dansyl chloride (0.81 g, 3.0 mmol) and stirred under an inert atmosphere at room temperature. After 20 hours, the mixture was diluted with water (50 mL) and extracted with ethyl acetate (2×50 mL). The combined extracts were washed with water then saturated brine, then dried over $MgSO_4$ and stripped of solvent under reduced pressure to afford the product (1.3 g); m.p. 231–232° C.

Calculated for $C_{26}H_{25}N_3O_4S$: C, 65.67; H, 5.30; N, 8.84. Found: C, 65.44; H, 5.29; N, 8.69.

Example 144

2-Methoxy-5-phenylcarbamoyl-carbonic acid-phenyl ester phenyl ester

A solution of phenyl chloroformate (0.75 g, 4.8 mmol) in tetrahydrofuran (8 mL) was added dropwise to a stirred solution of 3-hydroxy-4-methoxy-N-phenyl-benzamide (1.1 g, 4.5 mmol) and 1,4-diazabicyclooctane (0.5 g, 4.5 mmol) in tetrahydrofuran (90 mL) under an inert atmosphere at ice bath temperature. The mixture was allowed to warm gradually to room temperature. After 20 hours, additional diazabicyclooctane (0.6 g, 5.3 mmol) and phenyl chloroformate (0.75 g, 4.8 mmol) were added and the mixture heated to reflux. After 20 hours, the mixture was stirred into ice water and extracted with ethyl acetate (2×75 mL). The combined extracts were washed successively with water, ice-cold 1N HCl, 2N $K_2CO_3$, and saturated brine then dried over $MgSO_4$. The solvent was removed under reduced pressure and the residue recrystallized from ethanol to afford the product (0.7 g); m.p. 152–153° C.

Calculated for $C_{21}H_{17}NO_5$: C, 69.41; H, 4.72; N, 3.85. Found: C, 69.14; H, 4.59; N, 3.91.

Example 145

4-Hydroxy-3-phenylamino-N-phenyl-benzamide

Boron tribromide-dimethyl sulfide complex (3.1 g, 9.9 mmol) was added to a stirred suspension of 4-methoxy-3-phenylamino-N-phenyl-benzamide from Example 28 (0.9 g, 2.8 mmol) in 1,2-dichloroethane (50 mL) under an inert atmosphere, and the mixture heated to reflux. After 1.5 hours, the mixture was allowed to cool and was poured into water (125 mL) and extracted with dichloromethane (2×75 mL). The combined extracts were washed with water, then saturated brine, and dried over $MgSO_4$. The solvent was removed under reduced pressure and the residue dissolved in ethyl acetate and filtered through a short column of silica gel. The filtrate was stripped of solvent and the residue recrystallized from toluene to afford the product (0.3 g); m.p. 158–159° C.

Calculated for $C_{19}H_{116}N_2O_2$: C, 74.98; H, 5.30; N, 9.20. Found: C, 74.48; H, 4.95; N, 8.82.

Example 146 (Intermediate)

3-Amino-4-trifluoromethoxy-N-(4-fluoro-phenyl)-benzamide

Step A: 3-Nitro-4-trifluoromethoxybenzoic Acid

A suspension of 4-trifluoromethoxybenzoic acid (TCI, Portland, Oreg.) (1.0 g, 4.9 mmol) in concentrated sulfuric acid (3 mL) was stirred under an inert atmosphere at room temperature until a solution was obtained. Fuming nitric acid (1 mL) was added dropwise. After 20 hours the mixture was poured into water (100 mL) and stirred. After an hour the precipitate was filtered off, rinsed with water and dried to afford the product (0.8 g); m.p. 137–139° C.

Calculated for $C_8H_4F_3NO_5$: C, 38.26; H, 1.61; N, 5.58. Found: C, 37.89; H, 1.63; N, 5.54.

Step B: 3-Amino-4-trifluoromethoxy-N-(4-fluorophenyl)-benzamide

Prepared according to the procedure described for Example 1 using 3-nitro-4-trifluoromethoxybenzoic acid from Step A (5.1 g, 20.5 mmol), oxalyl chloride (2.1 mL, 20.5 mmol), and 4-fluoroaniline (Aldrich. Milwaukee, Wis.) (4.6 g, 41.1 mmol) to afford the product (5.7 g); m.p. 139–140° C.

Calculated for $C_{14}H_{10}F_4N_2O_2$: C, 53.51; H, 3.21; N, 8.91. Found: C, 53.34; H, 3.20; N, 8.80.

Example 147 (Intermediate)

3-Amino-4-trifluoromethoxy-N-phenyl-benzamide

The title compound has been made using the procedure of Example 146, but using 4-trifluoromethoxybenzoic acid and aniline as starting materials, which are commercially available from TCI and Aldrich; m.p. 160–162° C.

Example 148

3-(3-Amino-4-methoxy-benzoylamino)-benzoic acid ethyl ester

The title compound has been made using the procedure of Example 1, but using 3-amino-4-methoxybenzoic acid and ethyl 3-aminobenzoate as starting materials, which are commercially available from Aldrich; m.p. 144–146° C.

Example 149

3-(3-Amino-4-methoxy-benzoylamino)-benzoic acid methyl ester

Step A: 3-(3-Nitro-4-methoxy-benzoylamino)-benzoic acid methyl ester

4-Methoxy-3-nitrobenzoic acid (5.0 g, 25 mmol) was added to thionyl chloride (20 mL) under an inert atmosphere and stirred and heated to reflux. After 2 hours the mixture was stripped to dryness by rotary evaporator, and 2 portions of benzene were successively mixed with then stripped from the residue to leave a solid. This residue was dissolved in tetrahydrofuran (20 mL) and added dropwise to a stirred solution of methyl 3-aminobenzoate (3.83 g, 25 mmol) and pyridine (2 mL) cooled in an icebath. The mixture was allowed to warm to room temperature following the addition, then the solvent was removed under reduced pressure. The residue was suspended in 1N HCl, stirred, filtered off, and washed successively with 1N HCl, 1N NaHCO$_3$ (2×), and water (2×). The resulting solid was boiled briefly in methanol (500 mL) then allowed to cool. Filtration afforded the product (8.0 g); m.p. 233–235° C., in sufficient purity for the next step.

STEP B: 3-(3-Amino-4-methoxy-benzoylamino)-benzoic acid methyl ester

Raney nickel (1 g) was added to a solution of 3-(3-nitro-4-methoxy-benzoylamino)-benzoic acid methyl ester from Step A (4.0 g, 12 mmol) in dimethylformamide (125 mL) and shaken at room temperature under an atmosphere of hydrogen, initially at a pressure of 50 psi, until the required amount was taken up. The catalyst was removed by filtration and the filtrate was stripped of solvent by rotary evaporator. Recrystallization of the residue from methanol (150 mL) gave the product (2.3 g); m.p. 160–162° C.

Calculated for $C_{16}H_{16}N_2O_4$: C, 63.99; H, 5.37; N, 9.33. Found: C, 63.96; H, 5.47; N, 9.29.

Example 150

3,4-Difluoro-N-(3-amino-4-methoxy-phenyl)-benzamide

The title compound has been made using the procedure of Example 23, but using 3,4-difluoro-N-(3-nitro-4-fluoro-phenyl)-benzamide from the preparation of Example 151 as a starting material; m.p. 148–151° C.

Example 151

3,4-Difluoro-N-(3-amino-4-fluoro-phenyl)-benzamide

The title compound has been made using the procedure of Example 22, but using 4-fluoro-3-nitroaniline and 3,4-difluorobenzoyl chloride as starting materials, which are commercially available from Aldrich; m.p. 135–142° C.

Example 152

1-(3-Amino-4-methoxy-phenyl)-3-(3,4-dichloro-phenyl)-urea

The title compound has been made using the procedure of Example 24, but using 3,4-dichlorophenyl isocyanate as a starting material, which is commercially available from Aldrich; m.p. 202–204° C.

Example 153

3-(4-Fluoro-phenylamino)-4-methoxy-N-phenyl-benzamide

The title compound has been made using the procedure of Example 25, but using 3-amino-4-methoxy-N-phenyl benzamide (Aldrich) and tris(4-fluorophenyl)bismuthane as starting materials; m.p. 178–180° C.

Example 154

3-(3,5-Dichloro-phenylamino-4-methoxy-N-(4-fluoro-phenyl)-benzamide

Copper(II) acetate (0.5 g, 2.8 mmol) was added to a stirred mixture of 3-amino-4-methoxy-N-(4-fluoro-phenyl)-benzamide from Example 8 (0.7 g, 2.7 mmol), 3,5-dichlorobenzene boronic acid (Lancaster Synthesis, Ltd., Lancashire, UK) (1.0 g, 5.2 mmol), triethylamine (0.88 g, 8.6 mmol), and ~2 g of ground 4A molecular sieves in dichloromethane (50 mL) and stirred at room temperature in a flask fitted with a drying tube. After 18 hours the mixture was filtered, the residue was rinsed with dichloromethane and the filtrate stripped of solvent under reduced pressure. The residue was chromatographed on a column of silica gel in CHCl$_3$/EtOAc (9:1) to afford a crystalline solid which was triturated in ether, filtered off and dried to afford the product (0.13 g); m.p. 220° C.

Calculated for $C_{20}H_{15}Cl_2FN_2O_2$: C, 59.28; H, 3.73; N, 6.91. Found: C, 58.44; H, 3.69; N, 6.57.

Example 155

3-(4-Fluoro-phenylamino)-4-methoxy-N-(4-fluoro-phenyl)-benzamide

The title compound has been made using the procedure of Example 25, but using the title compound of Example 8 as a starting material; m.p. 193–194° C.

Example 156

3-[4-Methoxy-3-(3-trifluoromethyl-phenylamino)-benzoylamino]-benzoic acid methyl ester The title compound has been made using the procedure of Example 25, but using the title compound of Example 149 as a starting material; m.p. 128–129° C.

Example 157

3-[4-Methoxy-3-(3-trifluoromethyl-phenylamino)-benzoylamino]-benzoic acid ethyl ester The title compound has been made using the procedure of Example 25, but using the title compound of Example 148 as a starting material; m.p. 169–170° C.

Example 158

4-Trifluoromethoxy-3-(3-trifluoromethyl-phenylamino)-N-phenyl-benzamide

The title compound has been made using the procedure of Example 25, but using the title compound of Example 147 as a starting material; m.p. 129–130° C.

Example 159

4-Trifluoromethoxy-3-(3-trifluoromethyl-phenylamino)-N-(4-fluoro-phenyl)-benzamide The title compound has been made using the procedure of Example 25, but using the title compound of Example 146 as a starting material; m.p. 143–144° C.

Example 160

3,4-Dichloro-N-[4-methoxy-3-(3-trifluoromethyl-phenylamino)-phenyl]-benzamide The title compound has been made using the procedure of Example 25, but using the title compound of Example 23 as a starting material; m.p. 151–152° C.

Example 161

3-[3-(2-Methoxy-5-phenylcarbamoyl-phenyl)-thioureido]-benzoic acid methyl ester The title compound has been made using the procedure of Example 60, but using 3-amino-4-methoxy-N-phenyl benzamide and 3-carbomethoxyphenyl isothiocyanate as starting materials, which are commercially available from Aldrich or Trans World Chemicals, Inc., Rockville, Md.; m.p. 178–180° C.

Example 162

3-{3-[5-(3,4-Difluoro-phenylcarbamoyl)-2-methoxy-phenyl]-thioureido}-benzoic acid The title compound has been made using the procedure of Example 113, but using the title compound of Example 15 as a starting material; m.p. 221–222° C.

Example 163

3-[3-(3,5-Dichloro-phenyl)-thioureido]-4-trifluoromethoxy-N-(4-fluoro-phenyl)-benzamide A mixture of 3-amino-4-trifluoromethoxy-N-(4-fluorophenyl)-benzamide from Example 146 (0.292 g, 0.92 mmol) and 3,5-dichloro-phenyl isothiocyanate (Lancaster) (0.191 g, 0.93 mmol) was allowed to stand in ethyl acetate (25 mL) two days at room temperature. Concentration to dryness and trituration with hexanes/ethyl acetate (4:1) followed by thin layer chromatography revealed no reaction had taken place. More 3,5-dichlorophenyl isothiocyanate (0.23 g, 1.13 mmol) was added, and the neat reaction mixture was heated on a steam-bath. Ethyl acetate (25 mL) was added and boiled to dryness. Trituration with hexanes/ethyl acetate (1:1) gave the product (0.120 g); m.p. 165–166° C.

Calculated for $C_2H_{13}Cl_2F_4N_3O_2S$: C, 48.66; H, 2.53; N, 8.11. Found: C, 48.44; H, 2.45; N, 7.89.

Example 164

3-[3-(3-Trifluoromethyl-phenyl-thioureido]-4-trifluoro-methoxy-N-(4-fluoro-phenyl)-benzamide A mixture of 3-trifluoromethylphenyl isothiocyanate (Trans World) (0.35 g, 1.7 mmol) and 3-amino-4-trifluoromethoxy-N-(4-fluoro-phenyl)-benzamide from Example 146 (0.5 g, 1.6 mmol) in ethyl acetate (25 mL) was stirred under an inert atmosphere at room temperature for 40 hours then heated to reflux. After 15 hours an additional amount (0.35 g, 1.7 mmol) of the isothiocyanate was added and the mixture stirred at room temperature. After several days the mixture was concentrated on a steambath to a thick oil. Upon cooling the residue partially crystallized, and was triturated in hexane then allowed to stand overnight. Filtration afforded a solid which was chromatographed on silica gel in $CHCl_3/EtOAc$ (9:1) to afford the product (0.39 g); m.p. 153–154° C.

Calculated for $C_{22}H_{14}F_7N_3O_2S$: C, 51.07; H, 2.73; N, 8.12. Found: C. 51.41; H, 2.97; N, 7.92.

Example 165

4-{3-[5-(3,4-Difluoro-phenylcarbamoyl)-2-methoxy-phenyl]-thioureido}-benzenesulfonic acid, sodium salt The title compound has been made using the procedure of Example 82, but using the title compound of Example 15 as a starting material; m.p. >280° C.

Example 166

4-{3-[5-(4-Fluoro-phenylcarbamoyl)-2-methoxy-phenyl]-thioureido}-benzoic acid The title compound has been made using the procedure of Example 113, but using the title compound of Example 8 as a starting material; m.p. 203–205° C.

Example 167

3-{3-[5-(4-Fluoro-phenylcarbamoyl)-2-methoxy-phenyl]-thioureido}-benzoic acid The title compound has been made using the procedure of Example 113, but using the title compound of Example 8 as a starting material; m.p. 218–220° C.

Example 168

4-{3-[5-(3,4-Difluoro-benzoylamino)-2-methoxy-phenyl]-thioureido}-benzoic acid The title compound has been made using the procedure of Example 102, but using the title compound of Example 150 as a starting material; m.p. 200–203° C.

Example 169

3-{3-[5-(3,4-Difluoro-benzoylamino)-2-methoxy-phenyl]-thioureido}-benzoic acid The title compound has been made using the procedure of Example 102, but using the title compound of Example 150 as a starting material; m.p. 218–220° C.

Example 170

N-{3-[3-(3,5-Dichloro-phenyl)-thioureido]-4-fluoro-phenyl}-3,4-difluoro-benzamide The title compound has been made using the procedure of Example 113, but using the title compound of Example 151 as a starting material; m.p. 197° C.

Example 171

1-(3,4-Dichloro-phenyl)-3-{3-[3-(3,5-dichloro-phenyl)-thioureido]4-methoxy-phenyl}-urea The title compound has been made using the procedure of Example 102, but using the title compound of Example 152 as a starting material; m.p. 202° C.

Example 172

3-(3-{5-[3-(3,4-Dichloro-phenyl)-ureido]-2-methoxy-phenyl}-thioureido)-benzoic acid methyl ester The title compound has been made using the procedure of Example 102, but using the title compound of Example 152 as a starting material; m.p. 193–194° C.

Example 173

3-(3-{5-[3-(3,4-Dichloro-phenyl)-ureido]-2-methoxy-phenyl}-thioureido)-benzoic acid The title compound has been made using the procedure of Example 102, but using the title compound of Example 152 as a starting material; m.p. 209–211° C.

Example 174

1-{3-[3-(3,5-Bis-trifluoromethyl-phenyl)-thioureido]-4-methoxy-phenyl}-3-(3,4-dichloro-phenyl)-urea The title compound has been made using the procedure of Example 113, but using the title compound of Example 152 as a starting material; m.p. 181° C.

Example 175

1-{3-[3-(4-Chloro-3-nitro-phenyl)-thioureido]-4-methoxy-phenyl}-3-(3,4-dichloro-phenyl)-urea The title compound has been made using the procedure of Example 113, but using the title compound of Example 152 as a starting material; m.p. 162–170° C.

Example 176

3-[3-(3,5-Dichloro-phenyl)-thioureido]-4-methoxy-benzoic acid benzyl ester

Step A: 4-Methoxy-3-nitro-benzoic acid benzyl ester

The acid chloride prepared as in Example 1, Step A (15.07 g, 162 mmol) was dissolved in tetrahydrofuran (150 mL, and 2.0 M benzylmagnesium chloride in tetrahydrofuran was added to the rapidly stirred solution. After 1 hour the reaction was quenched with saturated aqueous ammonium chloride solution. The mixture was diluted with ethyl acetate (700 mL), the layers were separated, the organic layer washed with 1N potassium hydroxide and brine, dried (magnesium sulfate), filtered and concentrated to leave an oil. The oil was filtered through silica gel using ethyl acetate as eluant and the nonpolar fractions were chromatographed 2 times on silica gel in hexanes/ethyl acetate, first (1:1), then (4:1). Concentration of the eluant followed by trituration with hexanes and a little ethyl acetate afforded the product (1.655 g).

Calculated for $C_{15}H_{13}NO_5$: C, 62.27; H, 4.56; N, 4.88. Found: C, 62.15; H, 4.46; N, 4.75.

Step B: 3-Amino-4-methoxy-benzoic acid benzyl ester

The product from Step A (1.52 g, 5.3 mmol) was reacted according to the procedure for Example 9, Step B to give the product (1.05 g) as an oil.

Calculated for $C_{15}H_{15}NO_3$: C, 70.02; H, 5.88; N, 5.44. Found: C, 70.22; H, 5.96; N, 5.31.

Step C: 3-[3-(3,5-Dichloro-phenyl)-thioureido]-4-methoxy-benzoic acid benzyl ester The product from Step B (0.1405 g, 0.55 mmol) was reacted according to the procedure for Example 60 with 3,5-dichlorophenyl isothiocyanate (0.128 g, 0.88 mmol) to give the product (0.214 g); m.p. 144–145° C.

Calculated for $C_{22}H_{18}Cl_2N_2O_2S$: C, 57.27; H, 3.93; N, 6.07. Found: C, 57.32; H, 4.09; N, 5.84.

Example 177

3-(Dodecane-1-sulfonylamino)-4-methoxy-N-phenyl-benzamide

The title compound has been made using the procedure of Example 126, but using 3-amino-4-methoxy-N-phenyl benzamide and 1-dodecanesulfonyl chloride as starting materials, which are commercially available from Aldrich and Alfa; m.p. 156–157° C.

Example 178

4-Methoxy-3-(octane-1-sulfonylamino)-N-phenyl-benzamide

The title compound has been made using the procedure of Example 127, but using 3-amino-4-methoxy-N-phenyl benzamide and 1-octanesulfonyl chloride as a starting material, which are commercially available from Aldrich and Lancaster; m.p. 154–155° C.

Example 179

3-(Decane-1-sulfonylamino)-4-methoxy-N-phenyl-benzamide

The title compound has been made using the procedure of Example 128, but using 3-amino-4-methoxy-N-phenyl benzamide and 1-decanesulfonyl chloride as starting materials, which are commercially available from Aldrich and Lancaster; m.p. 160–161° C.

Example 180

3-(3-Nitro-benzenesufonylamino)-4-methoxy-N-(3,4-difluoro-phenyl)-benzamide

The title compound has been made using the procedure of Example 121, but using the title compound of Example 15 as a starting material; m.p. 220–222° C.

Example 181

3,5-Dichloro-N-{5-[3-(3,4-dichloro-phenyl)-ureido]-2-methoxy-phenyl}-benzenesulfonamide The title compound has been made using the procedure of Example 121, but using the title compound of Example 4 as a starting material; m.p. 225–227° C.

Example 182

3-(1-Methylethyl-1-sulfonylamino)-4-methoxy-N-phenyl-benzamide

The title compound has been made using the procedure of Example 121, but using 3-amino-4-methoxy-N-phenyl benzamide and isopropylsulfonyl chloride as a starting material, which are commercially available from Aldrich; m.p 135–140° C.

Example 183

4-(2-Methoxy-5-phenylcarbamoyl-phenylsulfamoyl)-benzoic acid

The title compound has been made using the procedure of Example 121, but using 3-amino-4-methoxy-N-phenyl benzamide and 4-carboxybenzenesulfonyl chloride as starting materials, which are commercially available from Aldrich; m.p. 212–214° C.

Example 184

3-(Octadecane-1-sulfonylamino)-4-methoxy-N-phenyl-benzamide

The title compound has been made using the procedure of Example 121, but using 3-amino-4-methoxy-N-phenyl benzamide and 1-octadecanesulfonyl chloride as starting materials, which are commercially available from Aldrich and Lancaster; m.p. 154–156° C.

Example 185

3-(3-Amino-benzenesulfonylamino)-4-methoxy-N-(3,4-difluoro-phenyl)-benzamide

The title compound has been made using the procedure of Example 9, but using the title compound of Example 180 as a starting material; m.p. 212–214° C.

Example 186

4-Methoxy-3-(4-nitro-benzenesulfonylamino)-N-(3,4-difluoro-phenyl)-benzamide

The title compound has been made using the procedure of Example 121, but using the title compound of Example 15 as a starting material; m.p. 234–236° C.

Example 187

3-(4-Cyano-benzenesulfonylamino)-4-methoxy-N-(3,4-difluoro-phenyl)-benzamide

The title compound has been made using the procedure of Example 121, but using the title compound of Example 15 as a starting material; m.p. 228–230° C.

Example 188

4-Methoxy-(4-nitro-benzenesulfonylamino)-N-phenyl-benzamide

The title compound has been made using the procedure of Example 121, but using 3-amino-4-methoxy-N-phenyl benzamide and 4-nitrobenzenesulfonyl chloride as starting materials, which are commercially available from Aldrich; m.p. 224–227° C.

Example 189

3-(3-Cyano-benzenesulfonylamino)-4-methoxy-N-(4-fluoro-phenyl)-benzamide

The title compound has been made using the procedure of Example 121, but using the title compound of Example 8 as a starting material; m.p. 221–225° C.

Example 190

4-Methoxy-3-(nitro-benzenesulfonylamino)-N-(4-fluoro-phenyl)-benzamide

The title compound has been made using the procedure of Example 121, but using the title compound of Example 8 as a starting material; m.p. 221–240° C.

Example 191

4-Methoxy-3-(4-nitro-benzenesulfonylamino)-N-(4-fluoro-phenyl)-benzamide

The title compound has been made using the procedure of Example 121, but using the title compound of Example 8 as a starting material; m.p. 208–211° C.

Example 192

3-(4-Cyano-benzenesulfonylamino)-4-methoxy-N-phenyl-benzamide

The title compound has been made using the procedure of Example 121, but using 3-amino-4-methoxy-N-phenyl benzamide and 4-cyanobenzenesulfonyl chloride as starting materials, which are commercially available from Aldrich or Maybridge Chemical Company Ltd., Cornwall, UK; m.p. 206–208° C.

Example 193

3-(4-Cyano-benzenesulfonylamino)-4-methoxy-N-(4-fluoro-phenyl)-benzamide

The title compound has been made using the procedure of Example 121, but using the title compound of Example 8 as a starting material; m.p. 131–135° C.

Example 194

3-(Dodecane-1-sulfonylamino)-4-methoxy-N-(3,4-dichloro-phenyl)-benzamide

Pyridine (5 mL) was added to a mixture of 1-dodecanesulfonyl chloride (Maybridge) (0.8 g, 3.0 mmol) and 3-amino-4-methoxy-N-(3,4-dichloro-phenyl)-benzamide from Example 4 (0.73 g, 3.0 mmol) and stirred at room temperature. After 5 days the mixture was heated on a steambath for 1.5 hours, allowed to cool, and added to water (150 mL), acidified with 4N HCl, and stirred for an hour. The precipitate was filtered off, rinsed with water then with ethanol and dried to afford the product (1.3 g); m.p. 15–152° C. after recrystallization from ethanol and chromatography on silica gel in $CHCl_3$/EtOAc (9:1).

Calculated for $C_{26}H_{36}Cl_2N_2O_4S$: C, 57.45; H, 6.68; N, 5.15. Found: C, 57.68; H, 6.67; N, 4.90.

Example 195

3-(3-Cyano-benzenesulfonylamino)-4-methoxy-N-phenyl-benzamide

The title compound has been made using the procedure of Example 121, but using 3-amino-4-methoxy-N-phenyl benzamide and 3-cyanobenzenesulfonyl chloride as starting materials, which is commercially available from Aldrich or Maybridge; m.p. 195–197° C.

Example 196

3,4-Dichloro-N-4-methoxy-3-(4-methoxy-benzenesulfonylamino)-phenyl]-benzamide

The title compound has been made using the procedure of Example 121, but using the title compound of Example 23 as a starting material; m.p. 225–227° C.

Example 197

3,4-Dichloro-N-[4-methoxy-3-(toluene-4-sulfonylamino)-phenyl]-benzamide

The title compound has been made using the procedure of Example 121, but using the title compound of Example 23 as a starting material; m.p. 228–230° C.

Example 198

3,4-Difluoro-N-[4-methoxy-3-(3-amino-benzenesulfonylamino)-phenyl]-benzamide

The title compound has been made using the procedure of Example 121/9B, but using the title compound of Example 150 as a starting material; m.p. 205–209° C.

Example 199

3,4-Difluoro-N-[4-methoxy-3-(4-amino-benzenesulfonylamino)-phenyl]-benzamide

The title compound has been made using the procedure of Example 121/9B, but using the title compound of Example 150 as a starting material; m.p. 229–231° C.

Example 200

3,4-Difluoro-N-[4-methoxy-3-(1-dodecane-sulfonylamino)-phenyl]-benzamide

The title compound has been made using the procedure of Example 143, but using the title compound of Example 150 as a starting material; m.p. 132° C.

Example 201

3,4-Difluoro-N-[4-methoxy-3-(chloromethyl-sulfonylamino)-phenyl]-benzamide

The title compound has been made using the procedure of Example 143, but using the title compound of Example 150 as a starting material; m.p. 191–193° C.

Example 202

3,4-Difluoro-N-[4-methoxy-3-(4-nitro-benzenesulfonylamino)-phenyl]-benzamide

The title compound has been made using the procedure of Example 121, but using the title compound of Example 150 as a starting material; m.p. 231–249° C.

Example 203

3,4-Difluoro-N-[4-methoxy-3-(3-nitro-benzenesulfonylamino)-phenyl]-benzamide

The title compound has been made using the procedure of Example 121, but using the title compound of Example 150 as a starting material; m.p. 150–160° C.

Example 204

3,4-Difluoro-N-[3-(4-cyano-benzenesulfonylamino)-4-methoxy-phenyl]-benzamide

The title compound has been made using the procedure of Example 121, but using the title compound of Example 150 as a starting material; m.p. 255–257° C.

Example 205

3,4-Difluoro-N-[3-(3-cyano-benzenesulfonylamino)-4-methoxy-phenyl]-benzamide

The title compound has been made using the procedure of Example 121, but using the title compound of Example 150 as a starting material; m.p. 212–214° C.

Example 206

3,4-Difluoro-N-[4-fluoro-3-(thiophen-2-sulfonylamino)-phenyl]-benzamide

The title compound has been made using the procedure of Example 121, but using the title compound of Example 151 as a starting material; m.p. 202–203° C.

Example 207

Thiophene-2-sulfonic acid {5-[3-(3,4-dichloro-phenyl)-ureido]-2-methoxy-phenyl}-amide

The title compound has been made using the procedure of Example 143, but using the title compound of Example 152 as a starting material; m.p. 205–208° C.

Example 208

3-(3,5-Dichloro-benzenesulfonylamino)-4-methoxy-N-phenyl-thiobenzamide

A mixture of 3-(3,5-dichloro-benzenesulfonylamino)-4-methoxy-N-phenyl-benzamide from Example 118 (3.61 g, 8.0 mmol) and Lawesson's reagent (3.57 g, 8.8 mmol) was stirred at room temperature overnight in tetrahydrofuran (250 mL). The reaction mixture was warmed to 50° C. for about one hour, then to 65° C. for about 4 hours then stirred at room temperature overnight. The mixture was concentrated to dryness and the residue dissolved in ethyl acetate and filtered through silica gel. Concentration of the eluant followed by trituration in hexanes/ethyl acetate (1:1) afforded the crude product (3.06 g). A portion (0.8 g) of this was chromatographed on silica gel in hexanes/ethyl acetate (1:1) to afford a pure sample (0.324 g); m.p. 206–208° C.

Calculated for $C_{20}H_{16}Cl_2N_2O_3S_2$: C, 51.40; H, 3.45; N, 5.99. Found: C, 51.40; H, 3.66; N, 5.54.

Example 209

3,5-Dichloro-N-(2-methoxy-5-phenylaminomethyl-phenyl)-benzenesulfonamide

A mixture of 3-(3,5-dichloro-benzenesulfonylamino)-4-methoxy-N-phenyl-thiobenzamide from Example 208 (1.0 g, 2.1 mmol) and Raney Nickel (21 g) in ethanol (80 mL) was stirred at 50 degrees for 1.5 hours and then for 3 days at room temperature. The reaction mixture was filtered through Celite, concentrated to dryness, dissolved in ethyl acetate/methanol/tetrahydrofuran, filtered and concentrated to an oil. The oil was filtered through silica gel twice, first in hexanes/ethyl acetate (3:1), then in hexanes/ethyl acetate (85:15). Concentration of the eluant followed by trituration in hexanes/ethyl acetate gave the product 8/31/9811/6/98 (0.100 g); m.p. 105–108° C.

Calculated for $C_{20}H_{18}Cl_2N_2O_3S$: C, 54.93; H, 4.15; N, 6.41. Found: C, 55.40; H, 4.23; N, 6.30.

Example 210

3-(3-Hydroxy-benzylamino)-4-methoxy-N-(3,4-difluoro-phenyl)-benzamide

The title compound has been made using the procedure of Example 50, but using the title compound of Example 15 as a starting material; m.p. 160–163° C.

Example 211

3-(4-Diethylamino-benzylamino)-4-methoxy-N-phenyl-benzamide

The title compound has been made using the procedure of Example 50, but using 3-amino-4-methoxy-N-phenyl benzamide and 4-diethylaminobenzaldehyde as starting materials, which are commercially available from Aldrich; m.p. 180–181° C.

Example 212

3-(3-Fluoro-benzylamino)-4-methoxy-N-(3,4-difluoro-phenyl)-benzamide

The title compound has been made using the procedure of Example 50, but using the title compound of Example 15 as a starting material 172–174° C.

Example 213

3-(3-Hydroxy-benzylamino)-4-methoxy-N-phenyl-benzamide

The title compound has been made using the procedure of Example 50, but using 3-amino-4-methoxy-N-phenyl benzamide and 3-hydroxybenzaldehyde as starting materials, which are commercially available from Aldrich; m.p. 168–170° C.

Example 214

4-Methoxy-3-(3-fluoro-benzylamino)-N-phenyl-benzamide

The title compound has been made using the procedure of Example 50, but using 3-amino-4-methoxy-N-phenyl benzamide and 3-fluorobenzaldehyde as starting materials, which are commercially available from Aldrich; m.p. 137–140° C.

Example 215

4-Methoxy-3-(3-nitro-benzylamino)-N-phenyl-benzamide

The title compound has been made using the procedure of Example 50, but using 3-amino-4-methoxy-N-phenyl benzamide and 3-nitrobenzaldehyde as starting materials, which are commercially available from Aldrich; m.p. 172–175° C.

Example 216

4-Methoxy-3-(4-methoxy-benzylamino)-N-phenyl-benzamide

The title compound has been made using the procedure of Example 50, but using 3-amino-4-methoxy-N-phenyl benzamide and 4-methoxybenzaldehyde as starting materials, which are commercially available from Aldrich; m.p. 173–174° C.

Example 217

4- Methoxy-3-[(naphthalen-1-ylmethyl)-amino]-N-phenyl-benzamide

The title compound has been made using the procedure of Example 50, but using 3-amino-4-methoxy-N-phenyl benzamide and 1-naphthaldehyde as starting materials, which are commercially available from Aldrich; m.p. 172–174° C.

Example 218

4-Methoxy-3-(3,5-dimethyl-benzylamino)-N-phenyl-benzamide

The title compound has been made using the procedure of Example 50, but using 3-amino-4-methoxy-N-phenyl benzamide and 3,5-dimethylbenzaldehyde as starting materials, which are commercially available from Aldrich or Lancaster; m.p. 168–170° C.

Example 219

3-(2,3-Difluoro-benzylamino)-4-methoxy-N-phenyl-benzamide

The title compound has been made using the procedure of Example 50, but using 3-amino-4-methoxy-N-phenyl benzamide and 2,3-difluorobenzaldehyde as starting materials, which are commercially available from Aldrich; m.p. 134–135° C.

Example 220

Acetic acid 4-[(2-methoxy-5-phenylcarbamoyl-phenylamino)-methyl]-phenyl ester

The title compound has been made using the procedure of Example 50, but using 3-amino-4-methoxy-N-phenyl benzamide and 4-acetoxybenzaldehyde as starting materials, which are commercially available from Aldrich; m.p. 193–195° C.

Example 221

4-[(2-Methoxy-5-phenylcarbamoyl-phenylamino)-methyl]-benzoic acid methyl ester

The title compound has been made using the procedure of Example 50, but using 3-amino-4-methoxy-N-phenyl benzamide or 4-carbomethoxybenzaldehyde as starting materials, which are commercially available from Aldrich; m.p. 170–172° C.

Example 222

3-[(Furan-3-ylmethyl)-amino]-4-methoxy-N-phenyl-benzamide

The title compound has been made using the procedure of Example 50, but using 3-amino-4-methoxy-N-phenyl benzamide and 2-furaldehyde as starting materials, which are commercially available from Aldrich; m.p. 188–190° C.

Example 223

4-Methoxy-3-(2-methyl-benzylamino)-N-phenyl-benzamide

The title compound has been made using the procedure of Example 50, but using 3-amino-4-methoxy-N-phenyl benzamide and 2-methylbenzaldehyde as starting materials, which are commercially available from Aldrich; m.p. 167–169° C.

Example 224

4-Methoxy-3-(4-fluoro-benzylamino)-N-phenyl-benzamide

The title compound has been made using the procedure of Example 50, but using 3-amino-4-methoxy-N-phenyl benzamide and 4-fluorobenzaldehyde as starting materials, which are commercially available from Aldrich; m.p. 165–167° C.

Example 225

3-(4-Hydroxy-3-nitro-benzylamino)-4-methoxy-N-phenyl-benzamide

The title compound has been made using the procedure of Example 50, but using 3-amino-4-methoxy-N-phenyl benzamide and 3-nitro-4-hydroxybenzaldehyde as starting materials, which are commercially available from Aldrich; m.p. 175–176° C.

Example 226

3-(4-Diethylamino-benzylamino)-4-methoxy-N-(3,4-difluoro-phenyl)-benzamide

The title compound has been made using the procedure of Example 50, but using the title compound of Example 15 as a starting material; m.p. 165–167° C.

Example 227

3-Benzylamino-4-methoxy-N-(3,4-difluoro-phenyl)-benzamide

The title compound has been made using the procedure of Example 50, but using the title compound of Example 15 as a starting material; m.p. 176–178° C.

Example 228

3-(3-Hydroxy-4-nitro-benzylamino)-4-methoxy-N-phenyl-benzamide

The title compound has been made using the procedure of Example 50, but using 3-amino-4-methoxy-N-phenyl benzamide and 3-hydroxy-4-nitrobenzaldehyde as starting materials which are commercially available from Aldrich; m.p. 140–143° C.

Example 229

3-(3-Cyano-benzylamino)-4-methoxy-N-phenyl-benzamide

The title compound has been made using the procedure of Example 50, but using 3-amino-4-methoxy-N-phenyl benzamide and 3-cyanobenzaldehyde as starting materials, which are commercially available from Aldrich; m.p. 172–174° C.

Example 230

3-{[5-(3,4-Difluoro-phenylcarbamoyl)-2-methoxy-phenylamino]-methyl}-benzoic acid The title compound has been made using the procedure of Example 50, but using the title compound of Example 15 as a starting material; m.p. 240–243° C.

Example 231

3-(3-Chloro-benzylamino)-4-methoxy-N-phenyl-benzamide

The title compound has been made using the procedure of Example 50, but using 3-amino-4-methoxy-N-phenyl benzamide and 3-chlorobenzaldehyde as starting materials, which are commercially available from Aldrich; m.p. 203–205° C.

Example 232

3-(4-tert-Butyl-benzylamino)-4-methoxy-N-phenyl-benzamide

The title compound has been made using the procedure of Example 50, but using 3-amino-4-methoxy-N-phenyl benzamide and 4-tert-butylbenzaldehyde as starting materials, which are commercially available from Aldrich; m.p. 195–197° C.

Example 233

3-(4-Cyano-benzylamino)-4-methoxy-N-phenyl-benzamide

The title compound has been made using the procedure of Example 50, but using 3-amino-4-methoxy-N-phenyl benzamide and 4-cyanobenzaldehyde as starting materials, which are commercially available from Aldrich; m.p. 130–133° C.

Example 234

4-{[5-(3,4-Difluoro-phenylcarbamoyl)-2-methoxy-phenylamino]-methyl}-benzoic acid The title compound has been made using the procedure of Example 50, but using the title compound of Example 15 as a starting material; m.p. >240° C.

Example 235

4-Methoxy-3-(4-propoxy-benzylamino)-N-phenyl-benzamide

The title compound has been made using the procedure of Example 50, but using 3-amino-4-methoxy-N-phenyl benzamide and 4-n-propoxybenzaldehyde as starting materials, which are commercially available from Aldrich; m.p. 154–156° C.

Example 236

3-[(Biphenyl-4-ylmethyl)-amino]-4-methoxy-N-phenyl-benzamide

The title compound has been made using the procedure of Example 50, but using 3-amino-4-methoxy-N-phenyl benzamide and 4-phenylbenzaldehyde as starting materials, which are commercially available from Aldrich; m.p. 222–223° C.

Example 237

4-Methoxy-3-(4-methyl-benzylamino)-N-phenyl-benzamide

The title compound has been made using the procedure of Example 50, but using 3-amino-4-methoxy-N-phenyl benzamide and 4-methylbenzaldehyde as starting materials, which are commercially available from Aldrich; m.p. 184–186° C.

Example 238

4-Methoxy-3-(2-methoxy-benzylamino)-N-phenyl-benzamide

The title compound has been made using the procedure of Example 50, but using 3-amino-4-methoxy-N-phenyl benzamide and 2-methoxybenzaldehyde as starting materials, which are commercially available from Aldrich; m.p. 177–179° C.

Example 239

3-(4-Butyl-benzylamino)-4-methoxy-N-phenyl-benzamide

The title compound has been made using the procedure of Example 50, but using 3-amino-4-methoxy-N-phenyl benzamide and 4-n-butylbenzaldehyde as starting materials, which are commercially available from Aldrich; m.p. 171–173° C.

Example 240

3-(3-Fluoro-benzylamino)-4-methoxy-N-(3,4-dichloro-phenyl)-benzamide

The title compound has been made using the procedure of Example 50, but using the title compound of Example 15 as a starting material; m.p 153–155° C.

Example 241

3-[(2-Methoxy-5-phenylcarbamoyl-phenylamino)-methyl]-benzoic acid

The title compound has been made using the procedure of Example 50, but using 3-amino-4-methoxy-N-phenyl benzamide and 3-carboxybenzaldehyde as starting materials, which are commercially available from Aldrich; m.p. 210–212° C.

Example 242

3-(3,4-Dimethyl-benzylamino)-4-methoxy-N-phenyl-benzamide

The title compound has been made using the procedure of Example 50, but using 3-amino-4-methoxy-N-phenyl benzamide and 3,4-dimethylbenzaldehyde as starting materials, which are commercially available from Aldrich or Maybridge; m.p. 163–164° C.

Example 243

3-(4-Isopropyl-benzylamino)-4-methoxy-N-phenyl-benzamide

The title compound has been made using the procedure of Example 50, but using 3-amino-4-methoxy-N-phenyl benzamide and 4-isopropylbenzaldehyde as starting materials, which are commercially available from Aldrich; m.p. 174–176° C.

Example 244

3,4-Dichloro-N-[3-(3-fluoro-benzylamino)-4-methoxy-phenyl]-benzamide

The title compound has been made using the procedure of Example 50, but using the title compound of Example 23 as a starting material; m.p. 197–199° C.

Example 245

3,4-Difluoro-N-[3-(3-hydroxy-benzylamino)-4-methoxy-phenyl]-benzamide

The title compound has been made using the procedure of Example 50, but using the title compound of Example 150 as a starting material; m.p. 174–176° C.

Example 246

3-{[5-(3,4-Difluoro-benzoylamino)-2-methoxy-phenylamino]-methyl}-benzoic acid

The title compound has been made using the procedure of Example 50, but using the title compound of Example 150 as a starting material; m.p. 218–221° C.

Example 247

3-[3-(3,5-Dichloro-phenyl)-thioureidomethyl]-4-methoxy-N-phenyl-benzamide

Step A: 4-Methoxy-3-cyanobenzoic Acid

A mixture of 4-methoxy-3-cyanomethyl benzoate (Maybridge) (9.94 g, 52 mmol) and 1N sodium hydroxide (51 mL) in water (150 mL) was heated briefly to 50° C., then water was added until the solution just became cloudy. After 5 days at room temperature the mixture was stripped of methanol, diluted with water (200 mL), and extracted once with ethyl acetate (discarded). The aqueous solution was acidified with 1N HCl then extracted with ethyl acetate (400 mL). The extract was washed with brine, dried over magnesium sulfate, filtered and stripped of solvent. Trituration of the residue in hexanes/ethyl acetate and filtration gave the product (6.79 g).

Calculated for $C_9H_7NO_3$: C, 61.02; H, 3.98; N, 7.91. Found: C, 61.10; H, 3.97; N, 7.93.

Step B: 4-Methoxy-3-cyano-N-phenyl-benzamide

Prepared according to the procedure described for Example 1, Step A using 4-methoxy-3-cyanobenzoic acid from Step A above to afford the product (1.781 g).

Calculated for $C_{15}H_{12}N_2O_2$: C, 71.42; H, 4.79; N, 11.10. Found: C, 71.10; H, 4.80; N, 11.02.

Step C: 4-Methoxy-3-aminomethyl-N-phenyl-benzamide

The product from Step B above (1.64 g, 6.5 mmol) was exposed to hydrogen gas (46 psi) in the presence of Raney Nickel (2 g) until gas uptake ceased. Concentration of the reaction mixture afforded the crude product (1.43 g). The product was purified by conversion to its N-t-butyloxy-carbonyl derivative, prepared as follows. The amine (1.43 g, 5.6 mmol) was treated with di-t-butyldicarbonate (1.68 g, 7.8 mmol) in dioxane/water (1:1), (110 mL) initially at 50° C. and then at room temperature for 3 days. The dioxane was removed by rotary evaporator and the residue extracted with ethyl acetate (150 mL). The organic extract was washed with 10% citric acid solution (50 mL), sodium bicarbonate solution (100 mL), and brine (50 mL), then dried over magnesium sulfate, filtered, and stripped of solvent. Trituration of the resulting solid in hexanes containing a few mL of ethyl acetate gave the carbamate (1.61 g). The carbamate (1.29 g, 3.6 mmol) was dissolved in dichloromethane (50 mL) and hydrogen chloride gas was bubbled in for about 3 minutes. The flask was stoppered and stirred at room temperature for 4 hours. The precipitate was collected by filtration washed successively with dichloromethane, ether and hexanes to afford the product (1.043 g).

Calculated for $C_{15}H_{16}N_2O_2 \cdot HCl$: C, 61.54; H, 5.85; N, 9.57. Found: C, 60.03; H, 5.76; N, 9.22.

Step D: 3-[3-(3,5-Dichloro-phenyl)-thioureidomethyl]-4-methoxy-N-phenyl-benzamide A mixture of the product from Step C (0.1585 g, 0.54 mmol), triethylamine (0.5 mL) and 3,5-dichlorophenyl isothiocyanate (Lancaster) (0.138 g, 0.68 mmol) was heated briefly to 50° C. and then allowed to stand at room temperature over-night. The reaction mixture was then re-warmed to 50° C., filtered, and concentrated to an oil which was triturated in hexanes/ethyl acetate (2:1) and filtered through silica gel in ethyl acetate to afford the product (0.067 g); m.p. 208–210° C.

Calculated for $C_{15}H_{16}N_2O_2 \cdot HCl$: C, 61.54; H, 5.85; N, 9.57. Found: C, 60.03; H, 5.76; N, 9.22.

Example 248

3-(3,5-Dichloro-benzenesulfonylamino)-4-methoxy-N-phenyl-benzamide

The title compound has been made using the procedure of Example 121, but using 3-amino-4-methoxy-N-phenyl benzamide and 3,5-dichlorophenylsulfonyl chloride as starting materials, which are commercially available from Aldrich or Lancaster; m.p. 226–228° C.

Example 249

3-[(3,5-Dichloro-benzenesulfonylamino)-methyl]-4-methoxy-N-phenyl-benzamide

The title compound has been made using the procedure of Example 120, but using the title compound of Example 247 as a starting material; mp 203–206° C.

Example 250

4-Methoxy-3-phenylmethanesulfonylamino-N-phenyl-benzamide

The title compound has been made using the procedure of Example 121, but using 3-amino-4-methoxy-N-phenyl benzamide and 3,5-dichlorobenzylsulfonyl chloride as starting materials, which are commercially available from Aldrich or Lancaster; m.p. 214–217° C.

Example 251

3-[Bis[(3,5-dichlorophenyl)sulfonyl]amino]-4-methoxy-N-phenyl-benzamide

The title compound has been made using the procedure of Example 25, but using 3-amino-4-methoxy-N-phenyl benzamide and 3,5-dichlorophenylsulfonyl chloride as starting materials, which are commercially available from Aldrich or Lancaster; m.p. 228–231° C.

Example 252

(2-Methoxy-5-phenylcarbamoyl-phenylcarbamoyl)-acetic acid phenylmethyl ester

Acetoxymandeloyl chloride (1.10 g, 5 mmol) was added to a mixture of 4-methoxy-3-amino-N-phenyl-benzamide (1.24 g, 5 mmol) and triethylamine (1.25 mL, 9 mmol) in ethyl acetate (50 mL). The flask was agitated briefly then allowed to stand overnight at room temperature. The reaction mixture was diluted with ethyl acetate (150 mL), washed with aqueous sodium bicarbonate solution (150 mL) then brine (100 mL), dried over magnesium sulfate, and filtered. Removal of the solvent followed by trituration in hexanes/ethyl acetate (2:1) gave the product (1.46 g.); m.p. 168–171° C.

Calculated for $C_{24}H_{22}N_2O_5$: C, 68.89; H, 5.30; N, 6.69. Found: C, 68.68; H, 5.14; N, 6.39.

Example 253

4-Methoxy-N-phenyl-3-[2-(3-trifluoromethyl-phenyl)-ethylamino]-benzamide

Step A: 4-Methoxy-N-phenyl-3-[2-(3-trifluoromethyl-phenyl)-acetylamino]-benzamide Dicyclohexylcarbodiimide (2.08 g, 10 mmol) was added to a stirred mixture of 4-methoxy-3-amino-N-phenyl-benzamide (2.44 g, 10 mmol) and 3-trifluoromethyl-phenyl-acetic acid (2.06 g, 10 mmol) in dichloromethane (80 mL) at room temperature followed by 1-hydroxybenzotriazole hydrate (1.36 g, 10 mmol). After overnight stirring the reaction mixture was filtered and the solid rinsed with ethyl acetate. The combined organic filtrates were washed with sodium bicarbonate solution (150 mL) then brine (100 mL), dried over magnesium sulfate, filtered, and concentrated. Trituration of the residue with hexanes/ethyl acetate (1:1) afforded the product (3.023 g).

Calculated for $C_{23}H_{19}F_3N_2O_3$: C, 64.48; H, 4.47; N, 6.54. Found: C, 64.46; H, 4.51; N, 6.64.

Step B: 4-Methoxy-N-phenyl-3-[2-(3-trifluoromethyl-phenyl)-thioacetylamino]-benzamide Prepared according to the procedure described for Example 208 using the product from step A above (2.14 g, 5 mmol) and Lawesson's reagent (4.04 g, 10 mmol) to give the product (0.261 g).

Calculated for $C_{23}H_{19}F_3N_2O_2S$: C, 62.15; H, 4.31; N, 6.30. Found: C, 61.82; H, 4.38; N, 6.27.

Step C: 4-Methoxy-N-phenyl-3-[2-(3-trifluoromethyl-phenyl)-ethylamino]-benzamide Prepared according to the procedure described for Example 209 using the product from Step C above (0.185 g, 0.42 mmol) and Raney Nickel (5 g) to give the product (0.079 g); m.p. 142–144° C.

Calculated for $C_{23}H_{21}F_3N_2O_2$: C, 66.66; H, 5.11; N, 6.76. Found: C, 66.55; H, 5.03; N, 6.62.

Example 254

4-Methoxy-3-[3-(3-nitro-phenyl)-thioureido]-N-phenyl-benzamide

The title compound has been made using the procedure of Example 60, but using 3-amino-4-methoxy-N-phenyl benzamide and benzoyl isothiocyanate as starting materials, which are commercially available from Aldrich; m.p. 217–219° C.

Example 255

3-[(3,5-Dichlorobenzoyl)amino]-4-methyl-N-phenyl-benzamide

The title compound has been made using the procedure of Example 252, but using 3-amino-4-methoxy-N-phenyl benzamide and 3,5-dichlorobenzoyl chloride as starting materials, which are commercially available from Aldrich; m.p. 202–205° C.

Example 256

3-[[(Cyanoimino)[(3,5-dichlorophenyl)amino]methyl]amino]-4-methoxy-N-phenyl-benzamide Step A 3-[3-(3,5-dichlorophenyl)-thioureido]-4-methoxy-N-phenyl-benzamide from Example 60 (1.83 g, 4.1 mmol) was stirred with methyl iodide (2 mL, 32 mmol) in tetrahydrofuran (50 mL) for 2 hours then allowed to stand overnight at room temperature. The precipitate was collected, washed with tetrahydrofuran and ether and air-dried to give the crude product (2.007 g), suitable for use in the next step.

Step B

A mixture of the product from Step A (1.87 g, 4.1 mmol) and cyanamide (Aldrich) (0.199 g, 4.7 mmol) was heated at just below reflux in acetonitrile (50 mL) under nitrogen. After about 18 hours additional cyanamide (0.23 g) was added. Two hours later more cyanamide (0.39 g) was added followed by isopropanol (60 mL), and the mixture was heated to reflux. After 18 hours additional cyanamide (0.59 g) was added, and another portion (0.88 g) 18 hours later. About 18 hours after that the mixture was allowed to cool, and the precipitate was filtered off to afford the product (0.361 g); m.p. 225–227° C.

Calculated for $C_{22}H_{17}Cl_2N_5O_2$: C, 58.16; H, 3.77; N, 15.42. Found: C, 57.92; H, 3.84; N, 15.36.

Example 257

3-(2-Hydroxy-2-phenyl-acetylamino)-4-methoxy-N-phenyl-benzamide

1N Sodium hydroxide (3 mL) was added to (2-methoxy-5-phenylcarbamoyl-phenylcarbamoyl)-acetic acid phenylmethyl ester from Example 252 (1.29 g, 3.1 mmol) in methanol (80 mL) and the reaction mixture boiled until most of the solvent was gone. Additional 1N sodium hydroxide (4 mL) and methanol (80 mL) were added and the mixture again concentrated to near dryness. Ethyl acetate (100 mL), water (100 mL), and 1N HCl (10 mL) were added, the layers separated, the organic layer washed with brine (50 mL), dried over magnesium sulfate, and concentrated to an oil. Trituration in hexanes/ethyl acetate (4:1) afforded the product (0.826 g); m.p. 173–175° C.

Calculated for $C_{22}H_{20}N_2O_4$: C, 70.20; H, 5.36; N, 7.44. Found: C, 69.78; H, 5.12; N, 7.15.

Example 258

4-Methoxy-3-[(thiophen-2-ylmethyl)-amino]-N-(3,4-difluoro-phenyl)-benzamide

The title compound has been made using the procedure of Example 50, but using the title compound of Example 15 as a starting material; m.p. 172–174° C.

Example 259

4-Methoxy-3-[(thiophen-2-ylmethyl)-amino]-N-phenyl-benzamide

The title compound has been made using the procedure of Example 50, but using 3-amino-4-methoxy-N-phenyl benzamide and 2-thiophenecarboxaldehyde as starting materials, which are commercially available from Aldrich; m.p. 195–197° C.

Example 260

4-Methoxy-3-[(thiophen-2-ylmethyl)-amino]-N-(4-fluoro-phenyl)-benzamide

The title compound has been made using the procedure of Example 50, but using the title compound of Example 8 as a starting material; m.p. 179–181° C.

Example 261

4-Methoxy-3-[(thiophen-2-ylmethyl)-amino]-N-(3,4-dichloro-phenyl)-benzamide

The title compound has been made using the procedure of Example 50, but using the title compound of Example 4 as a starting material; m.p. 178–180° C.

Example 262

4-Methoxy-3-[(thiophen-2-ylmethyl)-amino]-N-pyridin-3-yl-benzamide

The title compound has been made using the procedure of Example 50, but using the title compound of Example 5 as a starting material; m.p. 154–155° C.

Example 263

3-{4-Methoxy-3-[(thiophen-2-ylmethyl)-amino]-benzoylamino}-benzoic acid ethyl ester The title compound has been made using the procedure of Example 50, but using the title compound of Example 148 as a starting material; m.p. 153–155° C.

Example 264

3,4-Dichloro-N-{4-methoxy-3-[(thiophen-2-ylmethyl)-amino]-phenyl}-benzamide

The title compound has been made using the procedure of Example 50, but using the title compound of Example 23 as a starting material; m.p. 185–188° C.

Example 265

3,4-Difluoro-N-{4-methoxy-3-[(thiophen-2-ylmethyl)-amino]-phenyl}-benzamide

The title compound has been made using the procedure of Example 50, but using the title compound of Example 150 as a starting material; m.p. 187–189° C.

Example 266

3-[(Benzo[1,3]dioxol-5-ylmethyl)-amino]-4-methoxy-N-phenyl-benzamide

The title compound has been made using the procedure of Example 50, but using 3-amino-4-methoxy-N-phenyl benzamide and 3,4-methylenedioxybenzaldehyde as starting materials, which can be purchased from Aldrich; m.p. 185–187° C.

Example 267

4-Methoxy-3-(3,5-difluoro-benzylamino)-N-phenyl-benzamide

The title compound has been made using the procedure of Example 50, but using 3-amino-4-methoxy-N-phenyl benzamide and 3,5-difluorobenzaldehyde as starting materials, which can be purchased from Aldrich; m.p. 175–177° C.

Example 268

3-(4-Dimethylamino-benzylamino)-4-methoxy-N-phenyl-benzamide

The title compound has been made using the procedure of Example 50, but using 3-amino-4-methoxy-N-phenyl benzamide and 4-dimethylaminobenzaldehyde as starting materials, which can be purchased from Aldrich; m.p. 195–197° C.

Example 269

4-Methoxy-3-(3-trifluoromethyl-benzylamino)-N-phenyl-benzamide

The title compound has been made using the procedure of Example 50, but using 3-amino-4-methoxy-N-phenyl benzamide and 3-trifluoromethylbenzaldehyde as starting materials, which can be purchased from Aldrich; m.p. 167–171° C.

Example 270

4-Methoxy-3-(2-fluoro-benzylamino)-N-phenyl-benzamide

The title compound has been made using the procedure of Example 50, but using 3-amino-4-methoxy-N-phenyl benzamide and 2-fluorobenzaldehyde as starting materials, which can be purchased from Aldrich; m.p 142–144° C.

Example 271

N-{3-[(2,3-Dihydro-benzo[1,4]dioxin-6-ylmethyl)-amino]-4-methoxy-phenyl}-benzamide The title compound has been made using the procedure of Example 50, but using 3-amino-4-methoxy-N-phenyl benzamide and 3,4-ethylenedioxybenzaldehyde as starting materials, which can be purchased from Aldrich; m.p. 174–175° C.

Example 272

3-(4-Hydroxy-benzylamino)-4-methoxy-N-phenyl-benzamide

The title compound has been made using the procedure of Example 50, but using 3-amino-4-methoxy-N-phenyl benzamide and 4-hydroxybenzaldehyde as starting materials, which can be purchased from Aldrich; m.p. 188–190° C.

Example 273

4-Methoxy-3-(3-methyl-benzylamino)-N-phenyl-benzamide

The title compound has been made using the procedure of Example 50, but using 3-amino-4-methoxy-N-phenyl benzamide and 3-methylbenzaldehyde as starting materials, which can be purchased from Aldrich; m.p. 184–185° C.

Example 274

3-(3,4-Difluoro-benzylamino)-4-methoxy-N-phenyl-benzamide

The title compound has been made using the procedure of Example 50, but using 3-amino-4-methoxy-N-phenyl benzamide and 3,4-difluorobenzaldehyde as starting materials, which can be purchased from Aldrich; m.p. 150–152° C.

The commercial suppliers of the starting materials used to make compounds of the present invention are shown below in Table A.

Example 275

3-[(Pyridin-3-ylmethyl)-amino]-4-methoxy-N-(3,4-difluoro-phenyl)-benzamide

The title compound has been made using the procedure of Example 50, but using the title compound of Example 15 and pyridine-3-carboxaldehyde, which is available from Aldrich, as starting materials; mp 148–149° C.

Example 276

3-[(Pyridin-3-ylmethyl)-amino]-4-methoxy-N-(3,4-dichloro-phenyl)-benzamide

The title compound has been made using the procedure of Example 50, but using the title compound of Example 4 and pyridine-3-carboxaldehyde, which is available from Aldrich, as starting materials; mp 145–147° C.

Example 277

3-[(Pyridin-3-ylmethyl)-amino]-4-methoxy-N-phenyl-3-benzamide

The title compound has been made using the procedure of Example 50, but using 3-amino-4-methoxy-benzanilide and pyridine-3-carboxaldehyde, which are available from Aldrich, as starting materials; mp 178–180° C.

Example 278

4-[(2-Methoxy-5-phenylcarbamoyl-phenylamino)-methyl]-benzoic acid

The title compound has been made using the procedure of Example 50, but using 3-amino-4-methoxy-benzanilide and 4carboxybenzaldehyde, which are available from Aldrich, as starting materials; mp >240° C.

Example 279

3,4-Difluoro-N-{[3-(pyridin-3-ylmethyl)-amino]-4-methoxy-phenyl}-benzamide

The title compound has been made using the procedure of Example 50, but using the title compound of Example 150 and pyridine-3-carboxyaldehyde, which is available from Aldrich, as starting materials; mp 177–179° C.

Example 280

3-(3-Acetylamino-phenylamino)-4-methoxy-N-phenyl-benzamide

The title compound has been made using the procedure of Example 154, but using 3-amino-4-methoxy-benzanilide, which is available from Aldrich, and 3-acetamidobenzeneboronic acid, which is available from Lancaster, as starting materials; mp 202–203° C.

TABLE A

| Example | Starting Material | Supplier | Starting Material | Supplier |
|---|---|---|---|---|
| 146 | 4-trifluoromethoxybenzoic acid | TCI | 4-fluoroaniline | Aldrich |
| 147 | 4-trifluoromethoxybenzoic acid | TCI | aniline | Aldrich |
| 148 | 3-amino-4-methoxybenzoic acid | Aldrich | ethyl 3-aminobenzoate | Aldrich |
| 149 | 3-amino-4-methoxybenzoic acid | Aldrich | methyl 3-aminobenzoate | Aldrich |
| 150 | * | | 3,4-difluorobenzoyl chloride | Aldrich |
| 151 | 4-fluoro-3-nitroaniline | Aldrich | 3,4-difluorobenzoyl chloride | Aldrich |
| 152 | * | | 3,4-dichlorophenyl isocyanate | Aldrich |
| 153 | 3-amino-4-methoxy-N-phenyl benzamide | Aldrich | tris(4-fluorophenyl)bismuthane | lit prep |
| 154 | * | | 3,5-dichlorbenzeneboronic acid | Lancaster |
| 155 | * | | tris(4-fluorophenyl)bismuthane | lit prep |
| 156 | * | | tris(3-trifluoromethylphenyl) bismuthane | lit prep |
| 157 | * | | tris(3-trifluoromethylphenyl) bismuthane | lit prep |
| 158 | * | | tris(3-trifluoromethylphenyl) bismuthane | lit prep |
| 159 | * | | tris(3-trifluoromethylphenyl) bismuthane | lit prep |
| 160 | * | | 3,4-dichlorobenzoyl chloride | Aldrich |
| 161 | 3-amino-4-methoxy-N-phenyl benzamide | Aldrich | 3-carbomethoxyphenyl isothiocyanate | TransWorld |
| 162 | * | | 3-carboxyphenyl isothiocyanate | TransWorld |
| 163 | * | | 3,5-dichlorophenyl isothiocyanate | Lancaster |
| 164 | * | | 3-trifluoromethylphenyl isothiocyanate | TransWorld |
| 165 | * | | 4-sulfophenyl isothiocyanate sodium salt | Aldrich |
| 166 | * | | 4-carboxyphenyl isothiocyanate | TransWorld |
| 167 | * | | 3-carboxyphenyl isothiocyanate | TransWorld |
| 168 | * | | 4-carboxyphenyl isothiocyanate | TransWorld |
| 169 | * | | 3-carboxyphenyl isothiocyanate | TransWorld |
| 170 | * | | 3,5-dichlorophenyl isothiocyanate | Lancaster |

TABLE A-continued

| Example | Starting Material | Supplier | Starting Material | Supplier |
|---|---|---|---|---|
| 171 | * | | 3,5-dichlorophenyl isothiocyanate | Lancaster |
| 172 | * | | 3-methoxycarbonylphenyl isothiocyanate | Lancaster |
| 173 | * | | 3-carboxyphenyl isothiocyanate | TransWorld |
| 174 | * | | 3,5-bis(trifluoromethyl)phenyl isothiocyanate | Aldrich |
| 175 | * | | 4-chloro-3-nitrophenyl isothiocyanate | Lancaster |
| 176 | 4-methoxy-3-nitrobenzoic acid | Aldrich | 3,5-dichlorophenyl isothiocyanate | Lancaster |
| 177 | 3-amino-4-methoxy-N-phenyl benzamide | Aldrich | 1-dodecanesulfonyl chloride | Alfa |
| 178 | 3-amino-4-methoxy-N-phenyl benzamide | Aldrich | 1-octanesulfonyl chloride | Lancaster |
| 179 | 3-amino-4-methoxy-N-phenyl benzamide | Aldrich | 1-decanesulfonyl chloride | Lancaster |
| 180 | * | | 3-nitrobenzenesulfonyl chloride | Aldrich |
| 181 | * | | 3,5-dichlorobenzenesulfonyl chloride | Lancaster |
| 182 | 3-amino-4-methoxy-N-phenyl benzamide | Aldrich | isopropylsulfonyl chloride | Aldrich |
| 183 | 3-amino-4-methoxy-N-phenyl benzamide | Aldrich | 4-carboxybenzenesulfonyl chloride | Aldrich |
| 184 | 3-amino-4-methoxy-N-phenyl benzamide | Aldrich | 1-octadecanesulfonyl chloride | Lancaster |
| 185 | * | | | |
| 186 | * | | 4-nitrobenzenesulfonyl chloride | Aldrich |
| 187 | * | | 4-cyanobenzenesulfonyl chloride | Maybridge |
| 188 | 3-amino-4-methoxy-N-phenyl benzamide | Aldrich | 4-nitrobenzenesulfonyl chloride | Aldrich |
| 189 | * | | 3-cyanobenzenesulfonyl chloride | Maybridge |
| 190 | * | | 3-nitrobenzenesulfonyl chloride | Aldrich |
| 191 | * | | 4-nitrobenzenesulfonyl chloride | Aldrich |
| 192 | 3-amino-4-methoxy-N-phenyl benzamide | Aldrich | 4-cyanobenzenesulfonyl chloride | Maybridge |
| 193 | * | | 4-cyanobenzenesulfonyl chloride | Maybridge |
| 194 | * | | 1-dodecanesulfonyl chloride | Maybridge |
| 195 | 3-amino-4-methoxy-N-phenyl benzamide | Aldrich | 3-cyanobenzenesulfonyl chloride | Maybridge |
| 196 | * | | 4-methoxybenzenesulfonyl chloride | Aldrich |
| 197 | * | | 4-methylbenzenesulfonyl chloride | Aldrich |
| 198 | * | | * | |
| 199 | * | | * | |
| 200 | * | | 1-dodecanesulfonyl chloride | Alfa |
| 201 | * | | chloromethylsulfonyl chloride | Alfa |
| 202 | * | | 4-nitrobenzenesulfonyl chloride | Aldrich |
| 203 | * | | 3-nitrobenzenesulfonyl chloride | Aldrich |
| 204 | * | | 4-cyanobenzenesulfonyl chloride | Maybridge |
| 205 | * | | 3-cyanobenzenesulfonyl chloride | Maybridge |
| 206 | * | | 2-thienylsulfonyl chloride | Aldrich |
| 207 | * | | 2-thienylsulfonyl chloride | Aldrich |
| 208 | * | | 3,4-dichlorobenzenesulfonyl chloride | Lancaster |
| 209 | * | | 3,4-dichlorobenzenesulfonyl chloride | Lancaster |
| 210 | * | | 3-hydroxybenzaldehyde | Aldrich |
| 211 | 3-amino-4-methoxy-N-phenyl benzamide | Aldrich | 4-diethylaminobenzaldehyde | Aldrich |
| 212 | * | | 3-fluorobenzaldehyde | Aldrich |
| 213 | 3-amino-4-methoxy-N-phenyl benzamide | Aldrich | 3-hydroxybenzaldehyde | Aldrich |
| 214 | 3-amino-4-methoxy-N-phenyl benzamide | Aldrich | 3-fluorobenzaldehyde | Aldrich |
| 215 | 3-amino-4-methoxy-N-phenyl benzamide | Aldrich | 3-nitrobenzaldehyde | Aldrich |
| 216 | 3-amino-4-methoxy-N-phenyl benzamide | Aldrich | 4-methoxybenzaldehyde | Aldrich |
| 217 | 3-amino-4-methoxy-N-phenyl benzamide | Aldrich | 1-naphthaldehyde | Aldrich |
| 218 | 3-amino-4-methoxy-N-phenyl benzamide | Aldrich | 3,5-dimethylbenzaldehyde | Lancaster |
| 219 | 3-amino-4-methoxy-N-phenyl benzamide | Aldrich | 2,3-difluorobenzaldehyde | Aldrich |
| 220 | 3-amino-4-methoxy-N-phenyl benzamide | Aldrich | 4-acetoxybenzaldehyde | Aldrich |
| 221 | 3-amino-4-methoxy-N-phenyl benzamide | Aldrich | 4-carbomethoxybenzaldehyde | Aldrich |
| 222 | 3-amino-4-methoxy-N-phenyl benzamide | Aldrich | 2-furaldehyde | Aldrich |
| 223 | 3-amino-4-methoxy-N-phenyl benzamide | Aldrich | 2-methylbenzaldehyde | Aldrich |
| 224 | 3-amino-4-methoxy-N-phenyl benzamide | Aldrich | 4-fluorobenzaldehyde | Aldrich |
| 225 | 3-amino-4-methoxy-N-phenyl benzamide | Aldrich | 3-nitro-4-hydroxybenzaldehyde | Aldrich |
| 226 | * | | 4-diethylaminobenzaldehyde | Aldrich |
| 227 | * | | benzaldehyde | Aldrich |
| 228 | * | | 3-hydroxy-4-nitrobenzaldehyde | Aldrich |
| 229 | 3-amino-4-methoxy-N-phenyl benzamide | Aldrich | 3-cyanobenzaldehyde | Aldrich |

TABLE A-continued

| Example | Starting Material | Supplier | Starting Material | Supplier |
|---|---|---|---|---|
| 230 | * | | 3-carboxybenzaldehyde | Aldrich |
| 231 | 3-amino-4-methoxy-N-phenyl benzamide | Aldrich | 3-chlorobenzaldehyde | Aldrich |
| 232 | 3-amino-4-methoxy-N-phenyl benzamide | Aldrich | 4-tert-butylbenzaldehyde | Aldrich |
| 233 | 3-amino-4-methoxy-N-phenyl benzamide | Aldrich | 4-cyanobenzaldehyde | Aldrich |
| 234 | * | | 4-carboxybenzaldehyde | Aldrich |
| 235 | 3-amino-4-methoxy-N-phenyl benzamide | Aldrich | 4-n-propoxybenzaldehyde | Aldrich |
| 236 | 3-amino-4-methoxy-N-phenyl benzamide | Aldrich | 4-phenylbenzaldehyde | Aldrich |
| 237 | 3-amino-4-methoxy-N-phenyl benzamide | Aldrich | 4-methylbenzaldehyde | Aldrich |
| 238 | 3-amino-4-methoxy-N-phenyl benzamide | Aldrich | 2-methoxybenzaldehyde | Aldrich |
| 239 | 3-amino-4-methoxy-N-phenyl benzamide | Aldrich | 4-n-butylbenzaldehyde | Aldrich |
| 240 | * | | 3-fluorobenzaldehyde | Aldrich |
| 241 | 3-amino-4-methoxy-N-phenyl benzamide | Aldrich | 3-carboxybenzaldehyde | Aldrich |
| 242 | 3-amino-4-methoxy-N-phenyl benzamide | Aldrich | 3,4-dimethylbenzaldehyde | Maybridge |
| 243 | 3-amino-4-methoxy-N-phenyl benzamide | Aldrich | 4-isopropylbenzaldehyde | Aldrich |
| 244 | * | | 3-fluorobenzaldehyde | Aldrich |
| 245 | * | | 3-hydroxybenzaldehyde | Aldrich |
| 246 | * | | 3-carboxybenzaldehyde | Aldrich |
| 247 | methyl 4-methoxy-3-cyanomethyl benzoate | Maybridge | 3,5-dichlorophenyl isothiocyanate | Lancaster |
| 248 | 3-amino-4-methoxy-N-phenyl benzamide | Aldrich | 3,5-dichlorophenylsulfonyl chloride | Lancaster |
| 249 | * | | 3,5-dichlorophenylsulfonyl chloride | Lancaster |
| 250 | 3-amino-4-methoxy-N-phenyl benzamide | Aldrich | 3,5-dichlorobenzylsulfonyl chloride | Lancaster |
| 251 | 3-amino-4-methoxy-N-phenyl benzamide | Aldrich | 3,5-dichlorophenylsulfonyl chloride | Lancaster |
| 252 | 3-amino-4-methoxy-N-phenyl benzamide | Aldrich | O-acetyl mandelic acid chloride | Aldrich |
| 253 | 3-amino-4-methoxy-N-phenyl benzamide | Aldrich | 3-trifluoromethylphenyl acetic acid | Aldrich |
| 254 | 3-amino-4-methoxy-N-phenyl benzamide | Aldrich | benzoyl isothiocyanate | Aldrich |
| 255 | 3-amino-4-methoxy-N-phenyl benzamide | Aldrich | 3,5-dichlorobenzoyl chloride | Aldrich |
| 256 | * | | cyanamide | Aldrich |
| 257 | * | | * | |
| 258 | * | | 2-thiophenecarboxaldehyde | Aldrich |
| 259 | 3-amino-4-methoxy-N-phenyl benzamide | Aldrich | 2-thiophenecarboxaldehyde | Aldrich |
| 260 | * | | 2-thiophenecarboxaldehyde | Aldrich |
| 261 | * | | 2-thiophenecarboxaldehyde | Aldrich |
| 262 | * | | 2-thiophenecarboxaldehyde | Aldrich |
| 263 | * | | 2-thiophenecarboxaldehyde | Aldrich |
| 264 | * | | 2-thiophenecarboxaldehyde | Aldrich |
| 265 | * | | 2-thiophenecarboxaldehyde | Aldrich |
| 266 | 3-amino-4-methoxy-N-phenyl benzamide | Aldrich | 3,4-methylenedioxybenzaldehyde | Aldrich |
| 267 | 3-amino-4-methoxy-N-phenyl benzamide | Aldrich | 3,5-difluorobenzaldehyde | Aldrich |
| 268 | 3-amino-4-methoxy-N-phenyl benzamide | Aldrich | 4-dimethylaminobenzaldehyde | Aldrich |
| 269 | 3-amino-4-methoxy-N-phenyl benzamide | Aldrich | 3-trifluoromethlybenzaldehyde | Aldrich |
| 270 | 3-amino-4-methoxy-N-phenyl benzamide | Aldrich | 2-fluorobenzaldehyde | Aldrich |
| 271 | 3-amino-4-methoxy-N-phenyl benzamide | Aldrich | 3,4-ethylenedioxybenzaldehyde | Aldrich |
| 272 | 3-amino-4-methoxy-N-phenyl benzamide | Aldrich | 4-hydroxybenzaldehyde | Aldrich |
| 273 | 3-amino-4-methoxy-N-phenyl benzamide | Aldrich | 3-methylbenzaldehyde | Aldrich |
| 274 | 3-amino-4-methoxy-N-phenyl benzamide | Aldrich | 3,4-difluorobenzaldehyde | Aldrich |

*Synthesis described in the Examples herein

Aldrich Chemical Company Inc
1001 West Saint Paul Avenue
Milwaukee, WI 53233
USA Trans World Chemicals, Inc.
14650 Southlawn Lane
Rockville, MD 20850
USA Maybridge Chemical Company Ltd.
Trevillett
Tintagel
Cornwall PL34 OHW
UK TCI America
9211 North Harborgate Street
Portland, OR 97203
USA Lancaster Synthesis Ltd.
Eastgate, White Lund
Morecambe
Lancashire LA3 3DY
UK.

The results of the assays described above are shown below in Tables 1, 2, and 3.

TABLE 1

| Example | h15LO (IC$_{50}$ nM) or % Inhibition at 10 $\mu$M |
|---|---|
| 2 | 290 |
| 4 | 10 |
| 5 | 38 |
| 6 | 79% |
| 7 | 67% |
| 8 | 157 |
| 9 | 38% |
| 10 | 42% |
| 11 | 390 |
| 12 | 73 |
| 14 | 68% |
| 15 | 9 |
| 16 | 79 |
| 17 | 65% |
| 18 | 2510 |
| 19 | 1100 |
| 20 | 203 |
| 21 | 2130 |
| 23 | 26 |

TABLE 2

| Example | h15LO (IC$_{50}$ nM) |
|---|---|
| 25 | 6430 |
| 26 | 1600 |
| 27 | 48% |
| 28 | 39 |
| 29 | >3000 |
| 30 | 10 |
| 31 | 10 |
| 32 | 23 |
| 33 | 12 |
| 34 | 29 |
| 35 | 7 |
| 36 | 11 |
| 37 | 2940 |
| 38 | >3000 |
| 39 | 50 |
| 40 | 17 |
| 41 | 65% |
| 42 | 410 |
| 43 | 73 |
| 44 | 25 |
| 45 | 440 |
| 46 | 20 |
| 47 | 100 |
| 48 | 28 |
| 50 | 846 |
| 51 | 69% |
| 52 | 62% |
| 53 | 57% |
| 54 | 60% |
| 55 | 54% |
| 56 | 18 |
| 57 | 165 |
| 58 | 80 |
| 59 | 1460 |
| 60 | 8.6 |
| 61 | 11 |
| 62 | 70 |
| 63 | 49 |
| 64 | 41 |
| 65 | 42 |
| 66 | 7 |
| 67 | 10000 |
| 68 | 42 |
| 69 | 32 |

TABLE 2-continued

| Example | h15LO (IC$_{50}$ nM) |
|---|---|
| 70 | 500 |
| 71 | 526 |
| 72 | 56 |
| 73 | 16 |
| 74 | 14.9 |
| 75 | 104 |
| 76 | 48 |
| 77 | 11 |
| 78 | 390 |
| 79 | 127 |
| 80 | 39 |
| 81 | 19 |
| 82 | 124 |
| 83 | 81 |
| 84 | 20 |
| 85 | 20 |
| 86 | 260 |
| 87 | 102 |
| 88 | 33 |
| 89 | 35 |
| 90 | 24 |
| 91 | 8 |
| 92 | 17 |
| 93 | 82 |
| 94 | 42 |
| 95 | 11 |
| 96 | 46 |
| 97 | 19 |
| 98 | 1000 |
| 99 | 11 |
| 100 | 19 |
| 101 | 66% |
| 102 | 170 |
| 104 | 13 |
| 105 | 14 |
| 106 | 11 |
| 107 | 9 |
| 108 | 34 |
| 109 | 26% |
| 110 | 290 |
| 111 | 79 |
| 112 | 26 |
| 113 | 52 |
| 114 | 120 |
| 115 | 44 |
| 116 | 20 |
| 118 | 49 |
| 119 | 90 |
| 120 | 40 |
| 121 | 25 |
| 122 | 187 |
| 123 | 31 |
| 124 | 48 |
| 125 | 28 |
| 126 | 48 |
| 127 | 167 |
| 128 | 54 |
| 129 | 79 |
| 130 | 402 |
| 131 | 609 |
| 132 | 115 |
| 133 | 58 |
| 134 | 137 |
| 135 | 63 |
| 136 | 48 |
| 137 | 151 |
| 138 | 28 |
| 139 | 104 |
| 140 | 39 |
| 141 | 582 |
| 142 | 12 |
| 143 | 25 |
| 144 | 1190 |
| 145 | 180 |
| 146 | 35.29% |
| 147 | 37.05% |

TABLE 2-continued

| Example | h15LO (IC$_{50}$ nM) |
|---|---|
| 148 | 613 |
| 149 | 330 |
| 150 | 205 |
| 151 | 82.66% |
| 152 | 57.49% |
| 153 | 54 |
| 154 | 97.66% |
| 155 | 94.44% |
| 156 | 90.33% |
| 157 | 78.83% |
| 158 | 48.28% |
| 159 | 44.58% |
| 160 | 119 |
| 161 | 22 |
| 162 | 55 |
| 163 | 629 |
| 164 | 1590 |
| 165 | 98.51% |
| 166 | 98.11% |
| 167 | 96.22% |
| 168 | 109 |
| 169 | 246 |
| 170 | 99.53% |
| 171 | 275 |
| 172 | 89.03% |
| 173 | 55% |
| 174 | 53% |
| 175 | 52% |
| 176 | 800 |
| 177 | 2 |
| 178 | 4 |
| 179 | 7 |
| 180 | 36 |
| 181 | 68 |
| 182 | 232 |
| 183 | 293 |
| 184 | 732 |
| 185 | 99.71% |
| 186 | 99.35% |
| 187 | 98.38% |
| 188 | 97.24% |
| 189 | 97.17% |
| 190 | 97.05% |
| 191 | 96.99% |
| 192 | 95.56% |
| 193 | 94.51% |
| 194 | 93.61% |
| 195 | 93.07% |
| 196 | 33 |
| 197 | 36 |
| 198 | 97.77% |
| 199 | 97.68% |
| 200 | 96.92% |
| 201 | 93.97% |
| 202 | 93.85% |
| 203 | 92.01% |
| 204 | 89.54% |
| 205 | 86.96% |
| 206 | 45.56% |
| 207 | 41.59% |
| 208 | 98.52% |
| 209 | 80.94% |
| 210 | 24 |
| 211 | 69 |
| 212 | 69 |
| 213 | 79 |
| 214 | 89 |
| 215 | 110 |
| 216 | 118.2 |
| 217 | 129 |
| 218 | 161 |
| 219 | 166 |
| 220 | 509 |
| 221 | 551 |
| 222 | 591 |
| 223 | 892 |
| 224 | 982 |
| 225 | 97.88% |
| 226 | 96.21% |
| 227 | 95.74% |
| 228 | 92.92% |
| 229 | 92.70% |
| 230 | 92.57% |
| 231 | 224 |
| 232 | 80.36% |
| 233 | 73.46% |
| 234 | 71.56% |
| 235 | 67.26% |
| 236 | 64.09% |
| 237 | 64% |
| 238 | 60% |
| 239 | 58.44% |
| 240 | 58.09% |
| 241 | 56.33% |
| 242 | 50% |
| 243 | 49.19% |
| 244 | 86 |
| 245 | 98.02% |
| 246 | 59.75% |
| 247 | 40 |
| 248 | 46 |
| 249 | 58 |
| 250 | 63 |
| 251 | 62.01% |
| 252 | 43% |
| 253 | 60.56% |
| 254 | 51% |
| 255 | 47% |
| 256 | 45% |
| 257 | 61% |
| 258 | 35 |
| 259 | 137 |
| 260 | 186 |
| 261 | 98.57% |
| 262 | 67.58% |
| 263 | 53.51% |
| 264 | 37 |
| 265 | 98.89% |
| 266 | 197 |
| 267 | 198 |
| 268 | 213 |
| 269 | 221 |
| 270 | 241 |
| 271 | 302 |
| 272 | 304 |
| 273 | 385 |
| 274 | 391 |
| 275 | 28 |
| 276 | 52 |
| 277 | 93 |
| 278 | 36% |
| 279 | 69 |
| 280 | 99% |

TABLE 3

Monocyte Recruitment Assay

| Example | ED$_{50}$ μM |
|---|---|
| 28 | 25% @ 30 μM |
| 35 | 26.3 |
| 51 | 20 |
| 56 | 2.6 |
| 60 | 17.6 |
| 65 | 22.7 |
| 66 | 38% @ 30 μM |

TABLE 3-continued

Monocyte Recruitment Assay

| Example | $ED_{50}$ μM |
|---|---|
| 67 | 24.1 |
| 68 | 2.3 |
| 69 | 13% @ 30 μM |

In Vivo Tests-Methods

Biochemical Methods

The entire descending thoracic aorta was assayed for its cholesteryl ester (CE), free cholesterol, and total phospholipid content. The lipids were extracted in chloroform:methanol (2:1) by the procedure of Folch, et al. Folch J., Lees M., Sloane-Stanley G. H., A simple method for the isolation and purification of total lipids from animal tissue, *J. Biol. Chem.*, 1957;226:497–509) and 300–500 μL of an internal standard, i.e., 200 mg/ml solution of 4-hydroxycholesterol in ethyl acetate:acetone (2:1), was added to the extracts of the thoracic aortic samples. After extraction, the organic phase was dried under nitrogen and redissolved in isooctane/tetrahydrofuran (97:3). The lipid content and composition of the thoracic aorta were measured using an HPLC method.

Cytochemical Methods

For histologic evaluation of the aortic arch lesions and for quantification of aortic arch cross-sectional lesion area, a 1 cm segment of the ascending aorta distal to the aortic valves was fixed in 10% neutral buffered formalin for 24 hours. The vessels were dehydrated, cleared in xylene, and infiltrated with molten paraffin (<60° C.) using a Tissue Tek VIP autoprocessor (Miles Scientific, Elkhart, Ind.). The tissue segments were embedded in paraffin and sectioned at 5 μm with a Reichert-Jung microtome (Baxter, McGraw Park, Ill.). In order to obtain a thorough representation of the histologic appearance of the aortic arch lesions, 3 ribbons of 20 sections each were cut. Each ribbon of sections was spaced approximately 100 μm apart. Three pairs of sections, i.e., 1 pair from each ribbon, were affixed to cleaned 3-aminopropyltriethoxy-silane coated glass slides and stored until stained. The general histologic character was evaluated in Verhoeff's elastica stained sections.

Morphometric Methods

The gross extent of atherosclerosis within the aortic arch was measured. In addition, sections of the aortic arch, a site of hypercholesterolemia-induced lesions, stained using the Verhoeff's elastica procedure were used for quantification of lesion cross-sectional. The internal elastic lamina (IEL) was indentified as a blue-black ring and images of that region were collected using a digital camera. The area within the IEL was quantified using the Image Pro Plus image analysis software. The area of the lumen of the aortic arch was also quantified in a similar fashion. Lesion area was defined as the difference between the area circumscribed by the internal elastic lamina and the lumen area.

Aortic arch lesion extent was also measured. The area distal to the 1 cm segment taken for histologic evaluation to the first intercostal ostia was removed from the animal, opened longitudinally and images of the surface of the vessel was collected using a digital camera. The lesions were identified as raised, opaque areas and their area was determined using the Image Pro Plus image analysis software. The area of the entire aortic arch was also determined. The percentage of aortic arch covered by atherosclerotic lesions was calculated.

In Vivo Tests - Results

| Example No. (10 mg/kg as diet admix) | Aortic Arch Lesion Extent (% Δ from Control) | Aortic Cholesteryl Ester Content (% Δ from Control) | Aortic Arch Cross-Sectional Lesion Area (% Δ from Control) |
|---|---|---|---|
| 75 | −49 | −28 | −90 |
| 60 | +40 | +59 | +84 |
| 4 | +20 | −7 | −94 |
| 91 | −12 | +50 | −11 |
| 100 | −2 | +11 | +2 |
| 40 | +35 | +5 | −6 |
| 119 | +46 | +46 | −50 |

NOTE: All vascular efficacy changes are observed in the absence of changes in plasma cholesterol levels.

Experimental Design: Rabbits were fed a 0.25% cholesterol, 3% peanut oil, 3% coconut oil diet with or without 10 mg/kg of the compounds noted above for 12 weeks.

What is claimed is:

1. Compounds having the Formula III

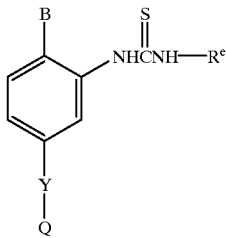

III wherein $R^e$ is pyridyl, or phenyl that is substituted with from 1 to 5 substituents selected from halogen, —$CF_3$, —$NO_2$, benzoyl, —$SO_3$ alkali metal, $C_1$–$C_6$ alkyl, —$OC_1$–$C_6$ alkyl, —CN,

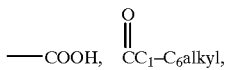

—$SO_3H$, —$OCF_3$,

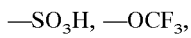

—$SO_2NH_2$, N($C_1$–$C_6$ alkyl)$_2$, or —$SONH_2$;

B is $OC_1$–$C_6$ alkyl, hydrogen, halogen, or $C_1$–$C_6$ alkyl;

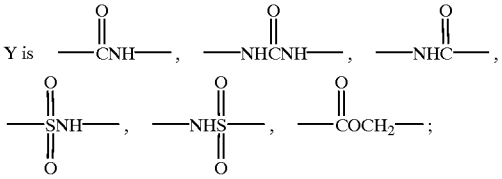

and

Q is phenyl, pyridyl, or phenyl substituted with 1 to 5 substituents selected from halogen, —$OC_1$–$C_6$ alkyl, halogen, or $C_1$–$C_6$ alkyl, or the pharmaceutically acceptable salts thereof.

2. A compound in accordance with claim 1 wherein $R^e$ is substituted phenyl.

3. A compound in accordance with claim 1 wherein B is —$OCH_3$ or —$OCF_3$, or fluorine.

4. A compound in accordance with claim 1 wherein

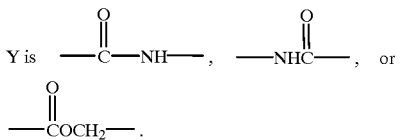

5. A compound in accordance with claim 1 wherein $R^e$ is substituted phenyl, B is —$OCH_3$, —$OCF_3$, and Y is

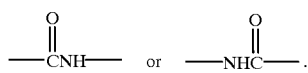

6. A method of treating or preventing atherosclerosis, the method comprising administering to a patient having atherosclerosis or at risk of having atherosclerosis a therapeutically effective amount of a compound of claim 1.

7. A method of treating or preventing inflammation, the method comprising administering to a patient having inflammation or at risk of having inflammation a therapeutically effective amount of a compound of claim 1.

8. A method of inhibiting 15-lipoxygenase, the method comprising administering to a patient in need of 15-lipoxygenase inhibition a 15-lipoxygenase inhibiting amount of a compound of claim 1.

9. A method of inhibiting the chemotaxis of monocytes, the method comprising administering to a patient in need of inhibition of chemotaxis of monocytes a chemotaxis inhibiting amount of a compound of claim 1.

10. A pharmaceutically acceptable composition comprising a compound of claim 1.

11. The compounds:
3-[3-(3,5-Dichlorophenyl)-thioureido]-4-methoxy-N-phenyl-benzamide;
4-[3-(2-Methoxy-5-phenylcarbamoyl-phenyl)-thioureido]-benzoic acid;
4-Methoxy-N-phenyl-3-(3-pyridin-3-yl-thioureido)-benzamide; or
3-[3-(3,5-Dichlorophenyl)-thioureido]-N-(4-flourophenyl)-4-methoxy-benzamide.

12. The compounds:
3-[3-(3-Chlorophenyl)-thioureido]-4-methoxy-N-phenyl-benzamide;
4-Methoxy-N-phenyl-3-(3-phenyl-thioureido)-benzamide;
4-Methoxy-N-phenyl-3-[3-(4-trifluoromethyl-phenyl)-thioureido]-benzamide;
3-[3-(4-tert-Butyl-phenyl)-thioureido]-4-methoxy-N-phenyl-benzamide;
3-[3-(4-Chlorophenyl)-thioureido]-4-methoxy-N-phenyl-benzamide;
3-[3-(3-Nitrophenyl)-thioureido]-4-methoxy-N-phenyl-benzamide;
4-Methoxy-N-phenyl-3-(3-benzoyl-thioureido)-benzamide;
4-Methoxy-N-phenyl-3-[3-(2,3,5,6-tetrafluoro-phenyl)-thioureido]-benzamide;
4-Methoxy-N-phenyl-3-(-3-p-tolyl-thioureido)-benzamide; or
3-[3-(3,5-Dichlorophenyl)-thioureido]-N-phenyl-benzamide.

13. The compounds:
3-[3-(3,5-Dichlorophenyl)-thioureido]-4-methyl-N-phenyl-benzamide;
3-[3-(3,4-Dimethoxyphenyl)-thioureido]-4-methoxy-N-phenyl-benzamide;
3-[3-(4-Chloro-3-trifluoromethylphenyl)-thioureido]-4-methoxy-N-phenyl-benzamide;
3-[3-(3-Cyanophenyl)-thioureido]-4-methoxy-N-phenyl-benzamide;
3-[3-(3-Acetyl-phenyl)-thioureido]-4-methoxy-N-phenyl-benzamide;
3-[3-(4-Chloro-3-nitrophenyl)-thioureido]-4-methoxy-N-phenyl-benzamide;
3-[3-(4-Fluorophenyl)-thioureido]-4-methoxy-N-phenyl-benzamide;
3-[3-(3,5-Dichlorophenyl)-thioureido]-4-methoxy-N-(4-methoxy-phenyl)-benzamide; or
3-[3-(3,5-Dichlorophenyl)-thioureido]-4-ethoxy-N-phenyl-benzamide.

14. The compounds:
4-[3-(2-Methoxy-5-phenylcarbamoyl-phenyl)-thioureido]-benzenesulfonic acid;
4-Methoxy-3-[3-(4-methoxy-phenyl)-thioureido]-N-phenyl-benzamide;
4-Methoxy-N-phenyl-3-[3-(3-trifluoromethyl-phenyl)-thioureido]-benzamide;
3-[3-(3,4-Dichlorophenyl)-thioureido]-4-methoxy-N-phenyl-benzamide;
1-{3-[3-(3,5-Dichlorophenyl)-thioureido]-4-methoxyphenyl}-3-phenyl-urea;
N-{3-[3-(3,5-Dichlorophenyl)-thioureido]-4-methoxy-phenyl}-benzamide;
4-Methoxy-3-[3-(4-nitrophenyl)-thioureido]-N-phenyl-benzamide;
3-[3-(3,5-Bis-trifluoromethylphenyl)-thioureido]-4-methoxy-N-phenyl-benzamide; or
4-Methoxy-N-phenyl-3-[3-(4-sulfamoyl-phenyl)-thioureido]-benzamide.

15. The compounds:
N-(4-Chlorophenyl)-3-[3-(3,5-dichlorophenyl)-thioureido]-4-methoxy-benzamide;
3-[3-(4-Dimethylaminophenyl)-thioureido]-4-methoxy-N-phenyl-benzamide;
3-[3-(3,5-Dichlorophenyl)-thioureido]-4-methoxy-N-p-tolyl-benzamide;
4-Methoxy-N-phenyl-3-(3-m-tolyl-thioureido)-benzamide;
3-[3-(3,5-Dichlorophenyl)-thioureido]-4-fluoro-N-phenyl-benzamide;
N-(3,4-Dichlorophenyl)-3-[3-(3,5-dichlorophenyl)-thioureido]-4-methoxy-benzamide;
4-Methoxy-N-phenyl-3-(3-o-tolyl-thioureido)-benzamide;
3-[3-(3,5-Dimethylphenyl)-thioureido]-4-methoxy-N-phenyl-benzamide; or
3-[3-(3,4-Dichlorophenyl)-thioureido]-4-methoxy-N-pyridin-3-yl-benzamide.

16. The compounds:
5-[3-(3,5-Dichlorophenyl)-thioureido]-2-fluoro-N-phenyl-benzamide;
N-(3,4-Dimethylphenyl)-4-methoxy-3-(3-m-tolyl-thioureido)-benzamide;
N-(3,5-Dimethylphenyl)-4-methoxy-3-(3-m-tolyl-thioureido)-benzamide;
N-(3-Chloro-4-methylphenyl)-3-[3-(3,5-dichlorophenyl)-thioureido]-4-methoxy-benzamide;
N-(3,4-Dichlorophenyl)-4-methoxy-3-[3-(4-sulfamoyl-phenyl)-thioureido]-benzamide;
3-[3-(3,5-Dichlorophenyl)-thioureido]-4-methylsulfanyl-N-phenyl-benzamide;

3-[3-(3,5-Dichlorophenyl)-thioureido]-N-(3,4-difluoro-phenyl)-4-methoxy-benzamide;
N-(3-Chlorophenyl)-3-[3-(4-fluorophenyl)-thioureido]-4-methoxy-benzamide;
3-[3-(3,5-Dichlorophenyl)-thioureido]-4-methoxy-N-phenyl-benzenesulfonamide; or
4-Ethyl-N-phenyl-3-[3-(3-trifluoromethylphenyl)-thioureido]-benzamide.

17. The compounds:
4-Ethyl-N-(3,4-difluorophenyl)-3-[3-(3-trifluoromethyl-phenyl)-thioureido]-benzamide;
3-{3-[2-Methoxy-5-(pyridin-3-ylcarbamoyl)-phenyl]-thioureido}-benzoic acid;
3-[3-(2-Methoxy-5-phenylcarbamoyl-phenyl)-thioureido]-benzoic acid;
3,4-Dichloro-N-{4-fluoro-3-[3-(3-trifluoromethylphenyl)-thioureido]-phenyl}-benzamide; or
3,4-Dichloro-N-{3-[3-(3,5-dichlorophenyl)-thioureido]-4-methoxyphenyl}-benzamide.

18. The compounds:
3-[3-(2-Methoxy-5-phenylcarbamoyl-phenyl)-thioureido]-benzoic acid methyl ester;
3-{3-[5-(3,4-Difluoro-phenylcarbamoyl)-2-methoxy-phenyl]-thioureido}-benzoic acid;
3-[3-(3,5-Dichloro-phenyl)-thioureido]-4-trifluoromethoxy-N-(4-fluoro-phenyl)-benzamide; or
3-[3-(3-trifluoromethyl-phenyl)-thioureido]-4-trifluoromethoxy-N-(4-fluoro-phenyl)-benzamide.

19. The compounds:
4-{3-[5-(3,4-Difluoro-phenylcarbamoyl)-2-methoxy-phenyl]-thioureido}-benzenesulfonic acid;
4-{3-[5-(4-Fluoro-phenylcarbamoyl)-2-methoxy-phenyl]-thioureido}-benzoic acid;
3-{3-[5-(4-Fluoro-phenylcarbamoyl)-2-methoxy-phenyl]-thioureido}-benzoic acid;
4-{3-[5-(3,4-Difluoro-benzoylamino)-2-methoxy-phenyl]-thioureido}-benzoic acid;
3-{3-[5-(3,4-Difluoro-benzoylamino)-2-methoxy-phenyl]-thioureido}-benzoic acid;
N-{3-[3-(3,5-Dichloro-phenyl)-thioureido]-4-fluoro-phenyl}-3,4-difluoro-benzamide;
1-(3,4-Dichloro-phenyl)-3-{3-[3-(3,5-dichloro-phenyl)-thioureido]-4-methoxy-phenyl}-urea; or
1-{3-[3-(3,5-Bis-trifluoromethyl-phenyl)-thioureido]-4-methoxy-phenyl}-3-(3,4-dichloro-phenyl)-urea.

20. The compounds:
1-{3-[3-(4-Chloro-3-nitro-phenyl)-thioureido]-4-methoxy-phenyl}-3-(3,4-dichloro-phenyl)-urea; or
3-[3-(3,5-Dichloro-phenyl)-thioureido]-4-methoxy-benzoic acid benzyl ester.

21. The compound which is
3-[3-(3,5-Dichloro-phenyl)-thioureidomethyl]-4-methoxy-N-phenyl-benzamide; or
4-Methoxy-3-[3-(3-nitro-phenyl)-thioureido]-N-phenyl-benzamide.

\* \* \* \* \*